US008470339B2

(12) United States Patent
Leroy et al.

(10) Patent No.: US 8,470,339 B2
(45) Date of Patent: Jun. 25, 2013

(54) ANTIGENS FOR PARATUBERCULOSIS DIAGNOSIS AND VACCINATION

(75) Inventors: Baptiste Leroy, Pipaix (BE); Ruddy Wattiez, Sirault (BE); Christiane A. J. Huygen, Brussels (BE); Virginie Roupie, Court-Saint-Etienne (BE); Marc Govaert, Brussels (BE); Isabelle Georis, Erpent (BE)

(73) Assignees: Universite de Mons, Mons (BE); Cerva-Coda, Brussels (BE); Institut Scientifique de Sante Publique, Brussels (BE)

( * ) Notice: Subject to any disclaimer, the term of this patent is extended or adjusted under 35 U.S.C. 154(b) by 243 days.

(21) Appl. No.: 12/513,802

(22) PCT Filed: Nov. 6, 2007

(86) PCT No.: PCT/EP2007/061954
§ 371 (c)(1),
(2), (4) Date: Dec. 21, 2009

(87) PCT Pub. No.: WO2008/055916
PCT Pub. Date: May 15, 2008

(65) Prior Publication Data
US 2011/0200603 A1     Aug. 18, 2011

Related U.S. Application Data

(60) Provisional application No. 60/857,664, filed on Nov. 6, 2006.

(51) Int. Cl.
*A61K 39/04* (2006.01)
*A61K 39/395* (2006.01)
*C07H 21/02* (2006.01)

(52) U.S. Cl.
USPC ............... 424/248.1; 424/184.1; 424/185.1; 424/190.1; 424/234.1; 424/130.1; 424/139.1; 424/150.1; 424/164.1; 536/23.1; 536/23.7

(58) Field of Classification Search
USPC .......... 424/184.1, 185.1, 190.1, 234.1, 248.1, 424/130.1, 139.1, 150.1, 164.1; 536/23.1, 536/23.7
See application file for complete search history.

(56) References Cited

U.S. PATENT DOCUMENTS

2003/0119018 A1* 6/2003 Omura et al. ............... 435/6

FOREIGN PATENT DOCUMENTS

| JP | 2006 514551 | 5/2006 |
|---|---|---|
| WO | WO 99/49054 | 9/1999 |
| WO | WO 00/34517 | 6/2000 |
| WO | WO 03/058248 A2 | 7/2003 |
| WO | WO 03/076898 | 9/2003 |
| WO | WO 2004/074310 A2 | 9/2004 |
| WO | WO 2006/089043 A3 | 8/2006 |

OTHER PUBLICATIONS

Eda et al., "A highly sensitive and subspecies-specific surface antigen enzyme-linked immunosorbent assay for diagnosis of Johne's Disease," *Clinical and Vaccine Immunology* (2006) 13 (8): 837-844.
Cho et al., "Identification of proteins of potential diagnostic value for bovine paratuberculosis," *Proteomics* (2006) 6: 5785-5794.
Paustian et al., "Characterization of novel coding sequences specific to *Mycobacterium avium* subsp. *paratuberculosis*: Implications for diagnosis of Johne's Disease," *Journal of Clinical Microbiology* (2004) 42 (6): 2675-2681.
Walravens et al., "IFN-γ diagnostic tests in the context of bovine mycobacterial infections in Belgium," *Veterinary Immunology and Immunopathology* (2002) 87: 401-406.
Tanghe et al., "Protective efficacy of a DNA vaccine encoding antigen 85A from *Mycobacterium bovis* BCG against Buruli Ulcer," *Infection and Immunity* (2001) 69 (9): 5403-5411.
Vordermeier et al., "Use of synthetic peptides derived from the antigens of ESAT-6 and CFP-10 for differential diagnosis of Bovine Tuberculosis in cattle," *Clinical and Diagnostic Laboratory Immunology* (2001) 8 (3): 571-578.
Walravens et al., "Analysis of the antigen-specific IFN-γ producing T-cell subsets in cattle experimentally infected by *Mycobacterium bovis*," *Veterinary Immunology and Immunopathology* (2002) 84: 29-41.
Rosseels et al., "Development of luminescent *Mycobacterium avium* subsp. *paratuberculosis* for rapid screening of vaccine candidates in mice," *Infection and Immunity* (2006) 74 (6): 3684-3686.
Noël-Georis et al., "Database of bronchoalveolar lavage fluid proteins," *Journal of Chromatography B* (2002) 771: 221-236.
Rosseels et al., "Members of the 30- to 32-Kilodalton mycolyl transferase family (Ag85) from culture filtrate *Mycobacterium avium* subsp. *paratuberculosis* are immunodominant Th1-type antigens recognized early upon infection in mice and cattle," *Infection and Immunity* (2006) 74 (1): 202-212.
Magnusson et al., "Preparation of purified tuberculin RT 23," *Bull. Wld Hlth Org.* (1958) 19: 829-843.
Moss et al., "Specific detection of *Mycobacterium paratuberculosis* by DNA hybridization with a fragment of the insertion element IS900," *Gut* (1991) 32: 395-398.
Sugden et al., "A comparison of lipoarabinomannan with other antigens used in absorbed enzyme immunoassays for the serological detection of cattle infected with *Mycobacterium paratuberculosis*," *J. Vet. Diagn. Invest.* (1997) 9: 413-417.

* cited by examiner

*Primary Examiner* — Rodney P. Swartz
(74) *Attorney, Agent, or Firm* — Merchant & Gould P.C.

(57) ABSTRACT

The present invention discloses new antigens of *Mycobacterium avium* subsp. *paratuberculosis*, antigenic compositions comprising at least two of said antigens, as well as epitopes, ant

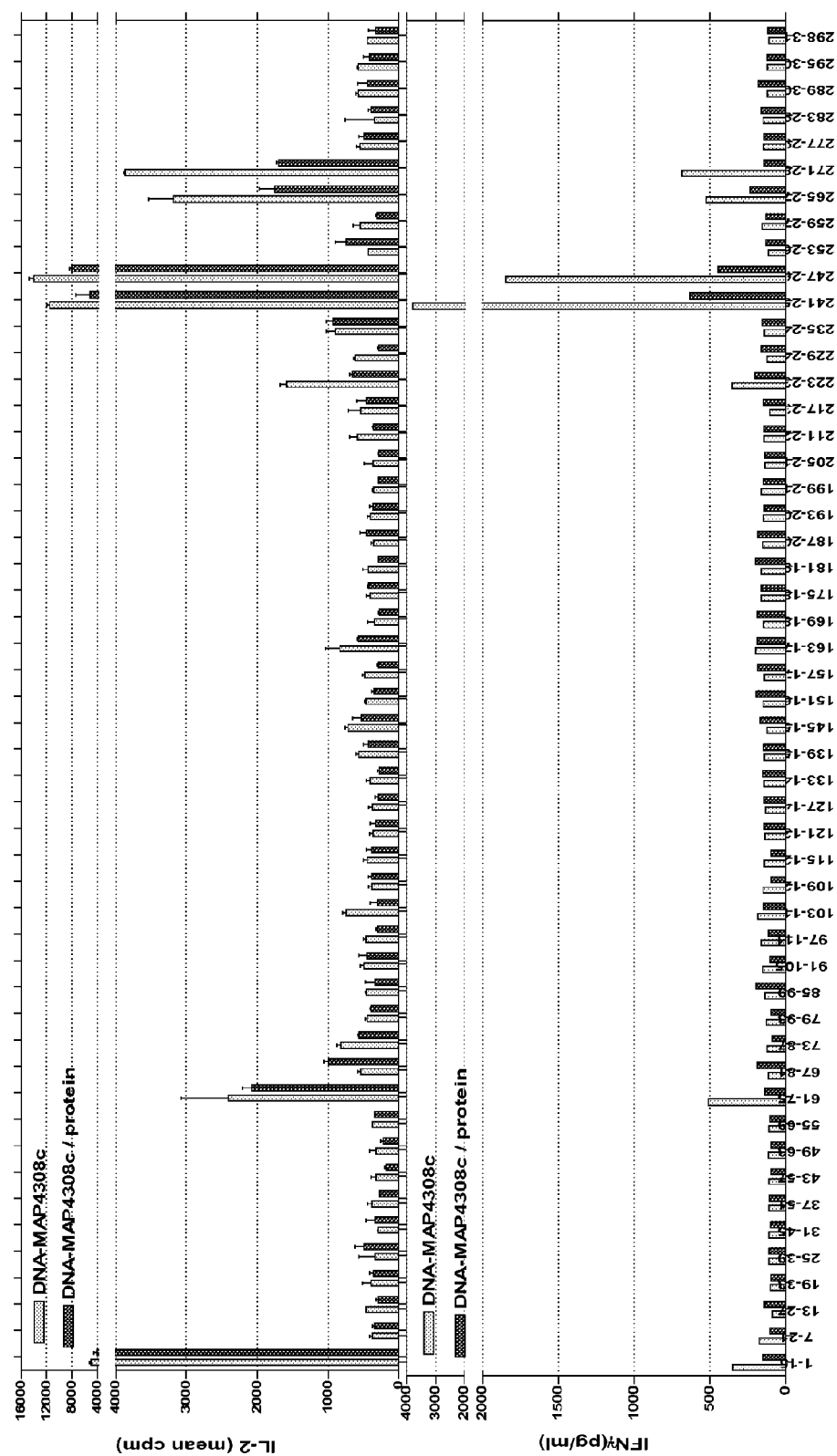

ANTIGENS FOR PARATUBERCULOSIS DIAGNOSIS AND VACCINATION

FIELD OF THE INVENTION

The present invention covers the medical field and more particularly the field of diagnosis and vaccination.

The present invention is more particularly related to proteins able to be used in the diagnosis and vaccination against *Mycobacterium avium* subsp. *paratuberculosis*, also known as Johne's disease, in cattle, but also in sheep and caprines.

These proteins could also be used in the diagnosis and vaccination against Crohn's disease in human.

BACKGROUND OF THE INVENTION

Bovine paratuberculosis, also called Johne's disease, is a chronic granulomatous enteritis caused by *Mycobacterium avium* subsp. *paratuberculosis* (MAP). Infected cattle develop diarrhea resulting in reduced milk production, severe emaciation and substantial financial losses to the farming industry. Not only cattle are receptive, but also most other domestic and wild ruminant species, making Johne's disease a growing issue to face the agricultural industry.

To date, no effective therapeutic nor vaccine agent is available, and early detection along with good management practices are the only ways to control paratuberculosis.

Most of the diagnostic tests available are limited by their relative lack of sensitivity and/or specificity.

For example, cultivation of bacteria excreted by animals at the clinical stage is highly specific, but only applicable to the latest stage of infection. Moreover, the slow growth of MAP translates into a 3-month waiting time to define individual infection status. Additionally, bacteria's shedding is clearly an inconstant phenomenon in this disease.

PCR detection of MAP on feces is rapid, but also applicable only to the late stage of infection, when animals start shedding bacteria.

Cell-mediated immunity (CMI) and serological assays remain the most promising ones, but so far remain hampered by the lack of specific immunodominant antigens.

Several antibody detection ELISA kits are commercially available, and are claimed to be highly specific. Most of them use crude cellular extracts and are based on preadsorption of the test sera on *Mycobacterium phlei*, to limit cross-reactivity due to sensitisation to environmental mycobacteria. However, this preadsorption step is responsible for a considerable decrease in sensitivity, particularly among animals shedding low numbers of bacilli. Moreover, it is not specified whether these tests are able to discriminate paratuberculosis from bovine tuberculosis caused by *M. bovis*.

Genomic screening of the fully sequenced MAP genome has allowed to identify prospectively MAP-specific immune targets. Antigenicity of these proteins has been evaluated by Western blot using sera from a small number of cattle naturally infected with MAP. To date, a number of antigens have been identified using this genomic approach but data about their reactivity in ELISA using larger panels of sera are still lacking.

MAP specific vaccines currently available in some countries are composed of whole bacteria (killed or attenuated) formulated in mineral oil adjuvants. These vaccines confer a partial protection against MAP, reducing the levels of excretion of bacteria in feces and the productivity losses.

However, these vaccines do not protect against the infection and moreover, they interfere with the skin test used in the official control programs for bovine tuberculosis, and with the indirect diagnostic tests for paratuberculosis (antibody ELISA and IFN-γ assay).

They can also induce an undesirable, granulomatous reaction at the injection site and finally their use is not without danger for the veterinary practitioner.

AIMS OF THE INVENTION

The present invention aims to provide new tools for the diagnosis of bovine paratuberculosis which do not present the drawbacks of the prior art cited hereabove.

The present invention also aims to provide new tools for the vaccination against bovine paratuberculosis.

In particular, the present invention aims to provide new tools which offer a reliable sensitivity and specificity.

The present invention also aims to provide new tools for the diagnosis of bovine paratuberculosis which are relatively easy and relatively rapid to perform.

The present invention further aims to provide new tools for the diagnosis of bovine paratuberculosis that are less expensive in terms of production and do not require qualified staff.

The present invention finally aims to provide new tools for the diagnosis of bovine paratuberculosis that could be directly used in the field.

DEFINITIONS AND ABBREVIATIONS

The <<specificity>> of a test, is defined by the proportion of known uninfected reference animals that test negative in the assay; uninfected reference animals that test positive are considered to have false-positive results. A test is said to present a high specificity when said test leads to a low rate of false positives.

The <<sensitivity>> of a test, is defined by the proportion of known infected reference animals that test positive in the assay; infected animals that test negative are considered to have false-negative results. A test is said to present a high sensitivity when said test leads to a low rate of false negatives.

The following abbreviations are used hereafter: 2-DE, two dimensional gel electrophoresis; CE, crude extract; CF, culture filtrate; CFU, colony forming units; IB, immunoblot buffer; MAP, *Mycobacterium avium* subsp. *paratuberculosis*; MS/MS, tandem mass spectrometry; RLU, relative light units; ROC, Receiver operating curve; Se, sensitivity; Sp, specificity.

It is meant by <<pharmaceutical active portion" of an antigen a portion of said antigen able to induce an immunogenic and/or antigenic response in a mammalian host, and preferably in cattle.

It is meant by "immunogenic response" an humoral and cellular response in a mammalian host, and preferably in cattle.

It is meant by "antigenic response" that the antigen is recognized by an antibody in a mammalian host, and preferably in cattle.

SUMMARY OF THE INVENTION

Reference is made to the set of claims which summarizes the present invention.

The present invention is related to an antigen of *Mycobacterium avium* subsp. *paratuberculosis*, said antigen comprising the amino acid sequence SEQ.ID.NO.2 (or a pharmaceutical active portion thereof).

The present invention is also related to an antigenic composition of *Mycobacterium avium* subsp. *paratuberculosis* comprising said antigen and at least an antigen comprising the amino acid sequence SEQ.ID.NO.1 (or a pharmaceutical active portion thereof).

Preferably, said antigenic composition further comprises an antigen comprising the amino acid sequence SEQ.ID.NO.3 (or a pharmaceutical active portion thereof).

Preferably, said antigenic composition further comprises an antigen comprising the amino acid sequence SEQ.ID.NO.4 (or a pharmaceutical active portion thereof).

Preferably, said antigenic composition further comprises an antigen comprising the amino acid sequence SEQ.ID.NO.5 (or a pharmaceutical active portion thereof).

Preferably, said antigenic composition further comprises at least an antigen comprising the amino acid sequence SEQ.ID.NO.6 (or a pharmaceutical active portion thereof).

Preferably, said antigenic composition further comprises an antigen comprising the amino acid sequence SEQ.ID.NO.7 (or a pharmaceutical active portion thereof).

The present invention also concerns an antigenic composition of *Mycobacterium avium* subsp. *paratuberculosis* comprising the antigen antigen comprising the amino acid sequence SEQ.ID.NO.2 (or a pharmaceutical active portion thereof), and at least one, at least two, at least three, at least four, at least five, at least six antigens comprising an amino acid sequence selected from the group consisting of SEQ.ID.NO.1, SEQ.ID.NO.3, SEQ.ID.NO.4, SEQ.ID.NO.5, SEQ.ID.NO.6 and SEQ.ID.NO.7 and a pharmaceutical active portions thereof.

Preferably, said antigenic composition further comprises at least one antigen comprising an amino acid sequence selected from the group consisting of SEQ.ID.NO.8 to SEQ.ID.NO.25 (and pharmaceutical active portions thereof).

The present invention also concerns an antigenic composition of *Mycobacterium avium* subsp. *paratuberculosis* comprising the antigen comprising the amino acid sequence SEQ.ID.NO.2 (or a pharmaceutical active portion thereof), and at least an antigen comprising the amino acid sequence SEQ.ID.NO.3 (or a pharmaceutical active portion thereof).

The present invention also concerns an antigenic composition of *Mycobacterium avium* subsp. *paratuberculosis* comprising the antigen comprising the amino acid sequence SEQ.ID.NO.2 (or a pharmaceutical active portion thereof), and at least an antigen comprising the amino acid sequence SEQ.ID.NO.4 (or a pharmaceutical active portion thereof).

The present invention also concerns an antigenic composition of *Mycobacterium avium* subsp. *paratuberculosis* comprising the antigen comprising the amino acid sequence SEQ.ID.NO.2 (or a pharmaceutical active portion thereof), and at least an antigen comprising the amino acid sequence SEQ.ID.NO.5 a pharmaceutical active portion thereof.

The present invention also concerns an antigenic composition of *Mycobacterium avium* subsp. *paratuberculosis* comprising the antigen comprising the amino acid sequence SEQ.ID.NO.2 (or a pharmaceutical active portion thereof), and at least an antigen comprising the amino acid sequence SEQ.ID.NO.6 (or a pharmaceutical active portion thereof).

The present invention also concerns an antigenic composition of *Mycobacterium avium* subsp. *paratuberculosis* comprising the antigen comprising the amino acid sequence SEQ.ID.NO.2 (or a pharmaceutical active portion thereof) and at least an antigen comprising the amino acid sequence SEQ.ID.NO.7 (or a pharmaceutical active portion thereof).

The present invention also concerns an antigenic composition of *Mycobacterium avium* subsp. *paratuberculosis* comprising the antigen comprising the amino acid sequence SEQ.ID.NO.2 (or a pharmaceutical active portion thereof) and at least an antigen comprising the amino acid sequence SEQ.ID.NO.3 (or a pharmaceutical active portion thereof) and an antigen comprising the amino acid sequence SEQ.ID.NO.4 (or a pharmaceutical active portion thereof).

The present invention also concerns an antigenic composition of *Mycobacterium avium* subsp. *paratuberculosis* comprising the antigen comprising the amino acid sequence SEQ.ID.NO.2 (or a pharmaceutical active portion thereof), and at least an antigen comprising the amino acid sequence SEQ.ID.NO.3 (or a pharmaceutical active portion thereof), an antigen comprising the amino acid sequence SEQ.ID.NO.4 (or a pharmaceutical active portion thereof), an antigen comprising the amino acid sequence SEQ.ID.NO.6 (or a pharmaceutical active portion thereof) and an antigen comprising the amino acid sequence SEQ.ID.NO.7 (or a pharmaceutical active portion thereof).

The present invention also concerns an antigen of *Mycobacterium avium* subsp. *paratuberculosis*, said antigen comprising the amino acid sequence SEQ.ID.NO.1 (or a pharmaceutical active portion thereof).

The present invention also concerns an antigenic composition of *Mycobacterium avium* subsp. *paratuberculosis* comprising the antigen comprising the amino acid sequence SEQ.ID.NO.1 (or a pharmaceutical active portion thereof) and at least an antigen comprising the amino acid sequence SEQ.ID.NO.2 (or a pharmaceutical active portion thereof).

Preferably, said antigenic composition further comprises an antigen comprising the amino acid sequence SEQ.ID.NO.3 (or a pharmaceutical active portion thereof).

Preferably, said antigenic composition further comprises an antigen comprising the amino acid sequence SEQ.ID.NO.4 (or a pharmaceutical active portion thereof).

Preferably, said antigenic composition further comprises an antigen comprising the amino acid sequence SEQ.ID.NO.5 (or a pharmaceutical active portion thereof).

Preferably, said antigenic composition further comprises at least an antigen comprising the amino acid sequence SEQ.ID.NO.6 (or a pharmaceutical active portion thereof).

Preferably, said antigenic composition further comprises an antigen comprising the amino acid sequence SEQ.ID.NO.7 (or a pharmaceutical active portion thereof).

The present invention also concerns an antigenic composition of *Mycobacterium avium* subsp. *paratuberculosis* comprising the antigen comprising the amino acid sequence SEQ.ID.NO.1 (or a pharmaceutical active portion thereof) and at least an antigen comprising the amino acid sequence SEQ.ID.NO.3 (or a pharmaceutical active portion thereof) and an antigen comprising the amino acid sequence SEQ.ID.NO.4 (or a pharmaceutical active portion thereof).

The present invention also concerns an antigenic composition of *Mycobacterium avium* subsp. *paratuberculosis* comprising the antigen comprising the amino acid sequence SEQ.ID.NO.1 (or a pharmaceutical active portion thereof) and at least one antigen comprising the amino acid sequence SEQ.ID.NO.3 (or a pharmaceutical active portion thereof).

The present invention also concerns an antigenic composition of *Mycobacterium avium* subsp. *paratuberculosis* comprising the antigen comprising the amino acid sequence SEQ.ID.NO.1 (or a pharmaceutical active portion thereof) and at least one antigen comprising the amino acid sequence SEQ.ID.NO.4 (or a pharmaceutical active portion thereof).

The present invention also concerns an antigenic composition of *Mycobacterium avium* subsp. *paratuberculosis* comprising the antigen comprising the amino acid sequence SEQ.ID.NO.1 (or a pharmaceutical active portion thereof) and at least one, at least two, at least three, at least four, at least five, at least six antigens comprising an amino acid sequence selected from the group consisting of SEQ.ID.NO.2, SEQ.ID.NO.3, SEQ.ID.NO.4, SEQ.ID.NO.5, SEQ.ID.NO.6 and SEQ.ID.NO.7, and pharmaceutical active portions thereof.

Preferably, said antigenic composition further comprises at least one antigen comprising an amino acid sequence selected from the group consisting of SEQ.ID.NO.8 to SEQ.ID.NO.25 (and pharmaceutical active portions thereof).

The present invention also concerns an antigen of *Mycobacterium avium* subsp. *paratuberculosis*, said antigen comprising the amino acid sequence SEQ.ID.NO.5 (or a pharmaceutical active portion thereof).

The present invention also concerns an antigen of *Mycobacterium avium* subsp. *paratuberculosis*, said antigen comprising the amino acid sequence SEQ.ID.NO.6 (or a pharmaceutical active portion thereof).

The present invention also concerns an antigen of *Mycobacterium avium* subsp. *paratuberculosis*, said antigen comprising the amino acid sequence SEQ.ID.NO.7 (or a pharmaceutical active portion thereof).

The present invention also concerns an antigen of *Mycobacterium avium* subsp. *paratuberculosis*, said antigen comprising an amino acid sequence selected from the group consisting of SEQ.ID.NO.8 to SEQ.ID.NO.25 (or a pharmaceutical active portion thereof).

The present invention is also related to an (conformational or linear) epitope of an antigen according the invention or any fragment thereof. Said epitope is possibly linked to a carrier molecule such as BSA or hemocyanin.

The present invention is also related to an antibody or a hypervariable fragment thereof directed against an antigen according the invention or an epitope thereof, and to the hybridoma cell producing the antibody or its hypervariable fragment.

The present invention is also related to a nucleotidic sequence (polynucleotide) coding for an antigen or for an epitope according to the invention.

The present invention is also related to the use of an antigen, an epitope, or an antibody, or a hypervariable fragment of said antibody, or a nucleotidic sequence or a antigenic composition according to the invention or a combination thereof as diagnostic composition for the serological diagnosis of *Paratuberculosis* in mammals, and in particular in cattle.

The present invention is also related to the use of the antigen comprising the amino acid sequence SEQ.ID.NO.2 as diagnostic composition for the serological diagnosis of *Paratuberculosis* in mammals, and in particular in cattle.

The present invention is also related to the use of an antigenic composition comprising an antigen comprising the amino acid sequence SEQ.ID.NO.2, an antigen comprising the amino acid sequence SEQ.ID.NO.3, and an antigen comprising the amino acid sequence SEQ.ID.NO.4 as diagnostic composition for the serological diagnosis of *Paratuberculosis* in mammals, and in particular in cattle.

The present invention is also related to the use of an antigenic composition comprising an antigen comprising the amino acid sequence SEQ.ID.NO.2, an antigen comprising the amino acid sequence SEQ.ID.NO.3, an antigen comprising the amino acid sequence SEQ.ID.NO.4, an antigen comprising the amino acid sequence SEQ.ID.NO.6, and an antigen comprising the amino acid sequence SEQ.ID.NO.7, as diagnostic composition for the serological diagnosis of *Paratuberculosis* in mammals, and in particular in cattle.

The present invention is also related to the use of an antigen comprising the amino acid sequence SEQ.ID.NO.6 for the serological diagnosis of *Paratuberculosis* in mammals, and in particular in cattle.

The present invention is also related to the use of an antigen comprising the amino acid sequence SEQ.ID.NO.7 for the serological diagnosis of *Paratuberculosis* in mammals, and in particular in cattle.

The present invention is also related to the use of an antigen, an epitope, or an antibody, or a nucleotidic sequence or an antigenic composition according to the invention or a combination thereof as diagnostic composition for the cellular diagnosis of *Paratuberculosis* in mammals, and in particular in cattle.

The present invention is also related to the use of an antigen comprising the amino acid sequence SEQ.ID.NO.2 as diagnostic composition for the cellular diagnosis of *Paratuberculosis* in mammals, and in particular in cattle.

The present invention is also related to the use of an antigen comprising the amino acid sequence SEQ.ID.NO.1 as diagnostic composition for the cellular diagnosis of *Paratuberculosis* in mammals, and in particular in cattle.

The present invention is also related to the use of an antigen comprising the amino acid sequence SEQ.ID.NO.3 as diagnostic composition for the cellular diagnosis of *Paratuberculosis* in mammals, and in particular in cattle.

The present invention is also related to the use of an antigenic composition comprising an antigen comprising the amino acid sequence SEQ.ID.NO.1, an antigen comprising the amino acid sequence SEQ.ID.NO.2 and an antigen comprising the amino acid sequence SEQ.ID.NO.3 as diagnostic composition for the cellular diagnosis of *Paratuberculosis* in mammals, and in particular in cattle.

The present invention is also related to the use of at least one antigen, or at least one epitope or at least one antibody, or at least one nucleotidic sequence or at least one antigenic composition according to the invention or a combination thereof for use as a medicament.

The present invention is also related to the use of at least one antigen, or antibody, or nucleotidic sequence, or antigenic composition according to the invention or a combination thereof for use as a vaccine against *Paratuberculosis* in mammals, and in particular in cattle.

The present invention also concerns a vaccine directed against *Mycobacterium avium* subsp. *paratuberculosis* comprising an adequate pharmaceutical vehicle and an antigen, or antibody, or a nucleotidic sequence or a composition according to any one of the preceding claims.

The present invention also concerns a vaccine directed against *Mycobacterium avium* subsp. *paratuberculosis* comprising an adequate pharmaceutical vehicle and at least one antigen comprising the amino acid sequence SEQ.ID.NO.1 or an epitope or an antibody thereof, or a nucleotidic sequence coding for said antigen.

The present invention also concerns a vaccine directed against *Mycobacterium avium* subsp. *paratuberculosis* comprising an adequate pharmaceutical vehicle and at least one antigen comprising the amino acid sequence SEQ.ID.NO.2 or an epitope or an antibody thereof, or a nucleotidic sequence coding for said antigen.

The present invention also concerns a vaccine directed against *Mycobacterium avium* subsp. *paratuberculosis* comprising an adequate pharmaceutical vehicle and an antigen comprising the amino acid sequence SEQ.ID.NO.3 or an epitope or an antibody thereof, or a nucleotidic sequence coding for said antigen.

The present invention also concerns a vaccine directed against *Mycobacterium avium* subsp. *paratuberculosis* comprising an adequate pharmaceutical vehicle and an antigen comprising the amino acid sequence SEQ.ID.NO.4 or an epitope or an antibody thereof, or a nucleotidic sequence coding for said antigen. Preferably, said vaccine further comprises an antigen comprising the amino acid sequence SEQ.ID.NO.3 or an epitope or an antibody thereof, or a nucleotidic sequence coding for said antigen. Preferably, said vaccine also further comprises an antigen comprising the amino acid sequence SEQ.ID.NO.1 or an epitope or an antibody thereof, or a nucleotidic sequence coding for said antigen. Alternatively and/or in addition, said vaccine further comprises an antigen comprising the amino acid sequence SEQ.ID.NO.2 or an epitope or an antibody thereof, or a nucleotidic sequence coding for said antigen.

The present invention also concerns any vaccine as disclosed hereabove further comprising an antigen comprising the amino acid sequence SEQ.ID.NO.5.

The present invention also concerns any vaccine as disclosed hereabove further comprising an antigen comprising the amino acid sequence SEQ.ID.NO.6.

The present invention also concerns any vaccine as disclosed hereabove further comprising an antigen comprising the amino acid sequence SEQ.ID.NO.7.

The present invention also concerns a diagnostic kit for the serological diagnosis of *Paratuberculosis* in mammals, preferably in cattle, comprising an antigen, or an antibody, or a hypervariable fragment thereof, or a nucleotidic sequence or a composition according to the invention and the adequate diagnostic tools.

The present invention also concerns a diagnostic kit for the serological diagnosis of *Paratuberculosis* in mammals, preferably in cattle, comprising an antigen comprising the amino acid sequence SEQ.ID.NO.2 or an antibody, or a hypervariable fragment thereof, or a nucleotidic sequence thereof and the adequate diagnostic tools.

The present invention also concerns a diagnostic kit for the serological diagnosis of *Paratuberculosis* in mammals, preferably in cattle, comprising the antigenic composition comprising an antigen comprising the amino acid sequence SEQ.ID.NO.2 or an antibody, or a hypervariable fragment thereof, or a nucleotidic sequence thereof, an antigen comprising the amino acid sequence SEQ.ID.NO.3 or an antibody, or a hypervariable fragment thereof, or a nucleotidic sequence thereof, and an antigen comprising the amino acid sequence SEQ.ID.NO.4 or an antibody, or a hypervariable fragment thereof, or a nucleotidic sequence thereof, and the adequate diagnostic tools.

The present invention also concerns a diagnostic kit for the serological diagnosis of *Paratuberculosis* in mammals, preferably in cattle, comprising the antigenic composition comprising an antigen comprising the amino acid sequence SEQ.ID.NO.2 or an antibody, or a hypervariable fragment thereof, or a nucleotidic sequence thereof, an antigen comprising the amino acid sequence SEQ.ID.NO.3 or an antibody, or a hypervariable fragment thereof, or a nucleotidic sequence thereof, an antigen comprising the amino acid sequence SEQ.ID.NO.4 or an antibody, or a hypervariable fragment thereof, or a nucleotidic sequence thereof, an antigen comprising the amino acid sequence SEQ.ID.NO.6 or an antibody, or a hypervariable fragment thereof, or a nucleotidic sequence thereof, an antigen comprising the amino acid sequence SEQ.ID.NO.7 or an antibody, or a hypervariable fragment thereof, or a nucleotidic sequence thereof, and the adequate diagnostic tools.

The present invention also concerns a diagnostic kit for the serological diagnosis of *Paratuberculosis* in mammals, preferably in cattle, comprising an antigen comprising the amino acid sequence SEQ.ID.NO.6 or an antibody, or a hypervariable fragment thereof, or a nucleotidic sequence thereof and the adequate diagnostic tools.

The present invention also concerns a diagnostic kit for the cellular diagnosis of *Paratuberculosis* in mammals, preferably in cattle, comprising an antigen comprising the amino acid sequence SEQ.ID.NO.7, or an antibody, or a hypervariable fragment thereof, or a nucleotidic sequence or a composition according to any one of the preceding claims and the adequate diagnostic tools.

The present invention also concerns a diagnostic kit for the cellular diagnosis of *Paratuberculosis* in mammals, preferably in cattle, comprising the antigen comprising the amino acid sequence SEQ.ID.NO.2, or an antibody, or a hypervariable fragment thereof, or a nucleotidic sequence thereof, as diagnostic composition for the cellular diagnosis of *Paratuberculosis* in mammals, and in particular in cattle.

The present invention also concerns a diagnostic kit for the cellular diagnosis of *Paratuberculosis* in mammals, preferably in cattle, comprising an antigen comprising the amino acid sequence SEQ.ID.NO.1, or an antibody, or a hypervariable fragment thereof, or a nucleotidic sequence thereof, as diagnostic composition for the cellular diagnosis of *Paratuberculosis* in mammals, and in particular in cattle.

The present invention also concerns a diagnostic kit for the cellular diagnosis of *Paratuberculosis* in mammals, preferably in cattle, comprising an antigenic composition comprising an antigen comprising the amino acid sequence SEQ.ID.NO.1, or an antibody, or a hypervariable fragment thereof, or a nucleotidic sequence thereof, an antigen comprising the amino acid sequence SEQ.ID.NO.2, or an antibody, or a hypervariable fragment thereof, or a nucleotidic sequence thereof, an antigen comprising the amino acid sequence SEQ.ID.NO.3, or an antibody, or a hypervariable fragment thereof, or a nucleotidic sequence thereof, as diagnostic composition for the cellular diagnosis of *Paratuberculosis* in mammals, and in particular in cattle.

The present invention also concerns a diagnostic kit for the cellular diagnosis of *Paratuberculosis* in mammals, preferably in cattle, comprising the antigen comprising the amino acid sequence SEQ.ID.NO.3, or an antibody, or a hypervariable fragment thereof, or a nucleotidic sequence thereof, as diagnostic composition for the cellular diagnosis of *Paratuberculosis* in mammals, and in particular in cattle.

Another object of the present invention is a method for the manufacture of a medicament in the treatment and/or the prevention against *Paratuberculosis* in mammals using at least one (an) antigen, or at least one antigen (an) antibody, or at least one antigen (a) nucleotidic sequence or at least one antigen (an) antigenic composition according to the present invention or a combination thereof and the adequate pharmaceutical vehicle.

Another object of the present invention is a pharmaceutical composition comprising at least one (an) antigen, or at least one antigen (an) antibody, or at least one antigen (a) nucleotidic sequence or at least one antigen (an) antigenic composition according to the present invention or a combination thereof and the adequate pharmaceutical vehicle.

Another object of the present invention is a pharmaceutical composition comprising at least one vaccine according to the present invention and an adequate pharmaceutical vehicle.

The present invention is also related to the use of the above-mentioned antigens and/or antigenic composition and/or epitopes/ and/or antibodies and/or nucleotide sequences as diagnostic composition for the diagnosis (serological and/or cellular) against *Mycobacterium avium* subsp. *paratuberculosis* in caprines and/or in sheep.

The present invention is also related to the use of the above-mentioned antigens and/or fragments thereof and/or corresponding antigenic composition and/or epitopes/ and/or antibodies and/or hypervariable fragments thereof and/or nucleotide sequences as diagnostic composition for the diagnosis (serological and/or cellular) against Crohn's disease in human.

The present invention is also related to the use of the above-mentioned antigens and/or antigenic composition and/or epitopes/ and/or antibodies and/or hypervariable fragments thereof and/or nucleotide sequences as vaccine composition for the vaccination against *Mycobacterium avium* subsp. *paratuberculosis* in caprines and/or in sheep.

The present invention is also related to the use of the above-mentioned antigens and/or fragments thereof and/or corresponding antigenic composition and/or epitopes/ and/or antibodies and/or hypervariable fragments thereof and/or nucleotide sequences as vaccine composition for the vaccination against Crohn's disease in human.

The present invention also concerns antigens comprising an amino acid sequence presenting more than 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99% sequence identity with one of the sequences listed in Tables 3 and 20, and namely with SEQ ID.NO.1, and/or SEQ ID.NO.2, and/or SEQ ID.NO.3, and/or SEQ ID.NO.4, and/or SEQ ID.NO.5, and/or SEQ ID.NO.6, and/or SEQ ID.NO.7.

The antigen or the amino acid sequence(s) according to the invention may be modified by or linked to at least one substitution group preferably selected from the group consisting of amide, acetyl, phosphoryl and/or glycosyl groups. Moreover, this antigen(s) may take the form of a "mature" protein. They may also be part of larger protein(s) or part of a fusion protein.

Preferably, the amino acid sequence(s) of the present invention further include(s) at least one additional amino acid sequence which contains secretory or leader sequences, pro-sequences, sequences which help in purification such as multiple histidine residues, or additional sequences for stability during recombination protection.

Another object of the present invention concerns variant(s) of the antigen(s) of the present invention or the nucleotidic sequence(s) (polynucleotide(s)). Preferably, said variant(s) varies from the referent by conservative amino acid substitutions. Preferably, at least one residue is substituted in said variant with another residue of similar characteristics. Advantageously, the substitutions in said variant are among Ala, Val, Leu and Ile; among Ser and Thr, among the acidic residues Asp and Glu; among Asn and Gln; among the basic residues Lys and Arg; or among aromatic residues Phe and Tyr.

Preferably, in the variant(s) of the present invention, several amino acids are substituted, deleted or added in any combination. Preferably, 5 to 10, more preferably 1 to 5, more preferably 1 to 2 amino acids are substituted, deleted or added in any combination, in this variant(s).

This variant(s) may be a naturally or non naturally occurring allelic variant(s).

The present invention is also related to a vector comprising at least one element selected from the group consisting of the polynucleotide(s), the antigen(s), (the variant(s)), according to the present invention and active fragments thereof.

Another object of the present invention concerns a cell transfected by or comprising the recombinant vector according to the invention.

The present invention further concerns an inhibitor (anti-sense sequence, ribozyme, antibody, hypervariable portion thereof, nanobody, etc.) raised against the polypeptide(s) (amino acid sequence(s)) or the polynucleotide(s), or the portion(s), according to the present invention.

The present invention is also related to an hybridoma cell line expressing said antibody.

The pharmaceutical composition in the present invention (especially a vaccine) may comprise these various elements of the invention in addition with one or more pharmaceutical adequate carrier molecules or one or more adjuvant molecules, anti-oxidants, buffer, bacterio status, solutes thickening agents or ions. Examples of carrier molecules are vectors comprising the polynucleotide sequence according to the invention for a transfection transformation of a cell or a carrier molecule which could be complexed or bounded to one or more of this element.

For instance, the isolated protein or polypeptide according to the invention could be bounded to a carrier molecule, such as BSA or hemocyanine for improving its antigenic and immunogenic properties especially for obtaining an efficient vaccinal immune response (humoral and cellular immune response, especially a T-cell immune response).

Furthermore, the isolated nucleotide sequence according to the invention could be bounded to one or more promoter/activator sequence which allows a modulated expression of said nucleotide sequence into specific cells.

Vector comprising the isolated nucleotide sequence according to the invention could correspond to plasmids or viral vectors, to cationic vesicles or to other lipid membranes such as liposomes.

This carrier molecules or vectors could be also used as adjuvant for inducing an efficient immune response in a patient especially when the pharmaceutical composition is a vaccine.

The term "adjuvant" has its usual meaning in the art of vaccine technology, i.e. a substance or a composition of matter which is not in itself capable of mounting a specific immune response against the antigen of the vaccine, but which is nevertheless capable of enhancing the immune response against the antigen. In other words, the combination of vaccination with antigen and adjuvant induces an immune response against the antigen which is stronger than that induced by the antigen alone.

Suitable carriers for administration of vaccines are well known in the art and can include buffers, gels, microparticles, implantable solids, solvents, other adjuvants or any other means by which the antigen of the vaccine can be introduced into a subject and be made sufficiently available to produce an immune response to the antigen.

Examples of others adjuvant molecules are saponine or suitable fractions thereof and lipopolysaccharides as described in the document EP 671 948, saponine fractions with one or more sterols present in specific formulation are described in the document WO 2007/068907 in addition.

Other examples of adjuvants are metallic salts, oil in water emulsion, lipid and/or derivative thereof, aminoalkyl glucosaminide phosphate, immunostimulotary oligonucleotides QS21 or combination thereof possibly in association with liposome described in the document WO 2006/123155 or U.S. Pat. No. 6,544,518.

An adjuvant composition may also comprise proteins from the *yersinia* genus as described in document WO 02/304 58.

An adjuvant could comprise also one or more carrier molecule(s), such as metallic salt particles (aluminium phosphate, aluminium hydroxide, calcium phosphate, magnesium phosphate, iron phosphate, calcium carbonate, magnesium carbonate, calcium sulphate, magnesium hydroxide or double salt like ammonium-iron phosphate, potassium, iron phosphate, calcium iron phosphate, calcium magnesium carbonate or a mixture of these salts or polyporous polymeric particles (such as microbeads or nanoparticles (as described in document WO 02/30458)).

An adjuvant could correspond also to an immuno stimulatory CpG oligo nucleotide, preferably CpG oligo nucleotide having a length between 15 and 45 nucleotides.

The pharmaceutical composition (vaccine) may also comprise other compounds which are used for enhancing the antigenicity or immunogenicity of active compounds by addition of immuno modulators on immuno adjuvants such as a cytokines, interferons, tumor necrosis factors, transforming growth factors, or colony stimulating factors preferably interleukin-2. The immunogenicity of the pharmaceutical composition (vaccine) could be also induced by an adequate immuno adjuvant which is preferably selected from the group consisting of block copolymer, ethylene copolymer, acrylic acid copolymer, an acrylic acid copolymer emulsion, a mineral oil emulsion or a mixture thereof, (such as squalen or squalane).

The pharmaceutical composition (vaccine) of the invention is of any suitable pharmaceutical form. Suitable solid or liquid pharmaceutical forms are, for example, granules, powders, pill, tablets, capsules, suppositories, syrups, emulsions, suspensions, creams, aerosols, drops or injectable solution in ampoule form, in whose preparation excipients and additives such as disintegrants, binders, coating agents, swelling agents, lubricants, flavorings, sweeteners or solubilizers are customarily used. In the particular case of a slow-release composition, the pharmaceutical composition may comprise a biocompatible matrix suitable for slow-release.

Regarding the pharmaceutical carrier, in general, the nature of the carrier will depend on the particular mode of administration being employed. For instance, parenteral formulations usually comprise injectable fluids that include pharmaceutically and physiologically acceptable fluids such as water, physiological saline, balanced salt solutions, or the like as a vehicle. For solid compositions, conventional non-toxic solid carriers can include, for example, pharmaceutical grades of mannitol, lactose, or magnesium stearate. In addition to biologically-neutral carriers, pharmaceutical compositions to be administered can contain minor amounts of non-toxic additives, such as wetting or emulsifying agents, preservatives, and pH buffering agents and the like.

The route of administration of the vaccine or pharmaceutical composition according to the present invention can be any suitable route of administration. It can be topical, intradermal, subcutaneous, oral, intravenous, parenteral, intraperitoneal.

The medical regime is any suitable regime. Amounts and regimens for the administration of the vaccine or the pharmaceutical composition according to the present invention can be determined by those with ordinary skill in the clinical art of treating the described diseases.

BRIEF DESCRIPTION OF THE FIGURES

FIG. 2 corresponds to SDS-PAGE electrophoresis results illustrating antigen expression for candidate antigens cloned into *E. coli* and produced by IPTG-induced expression. C, non induced control; MW, molecular weight marker.

Figure 1A:
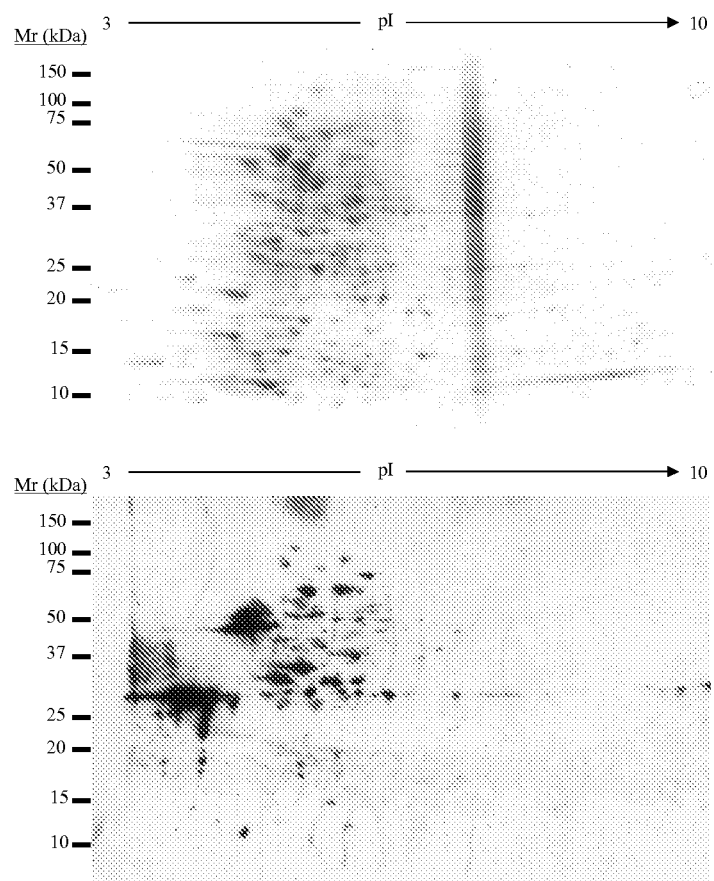
FIG. 1 presents the results for MAP CE and CF immunoproteomic analysis. MAP CE (FIG. 1A) and CF (FIG. 1B) were separated by 2DE (upper panel) and submitted to Western blot using sera of MAP infected cattle (lower panel). Specificity of antigenic protein was monitored by use of sera from *M. bovis* infected cattle.
Figure 1B:
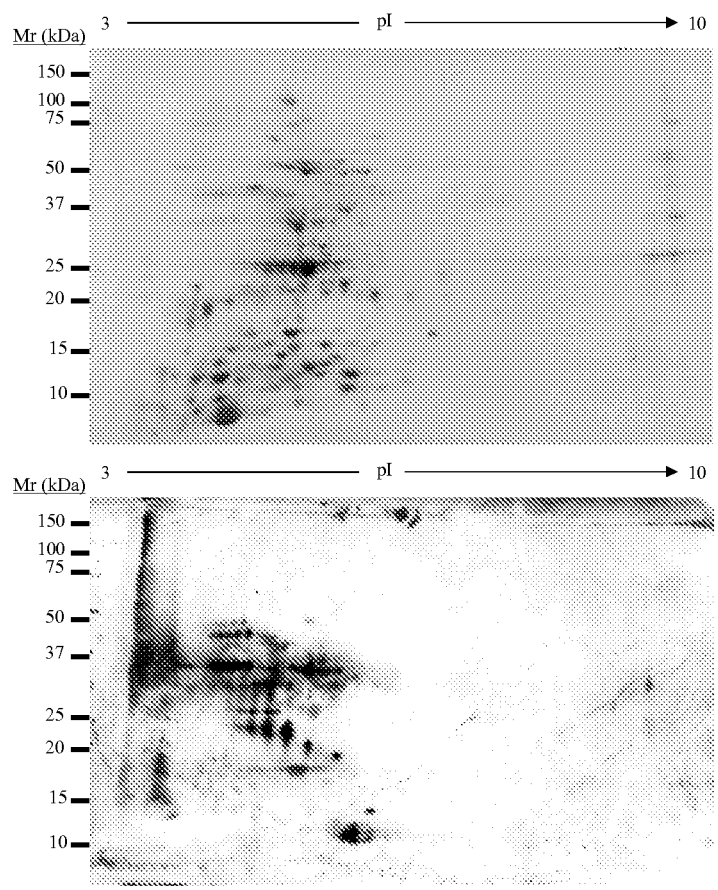
Figure 2A:
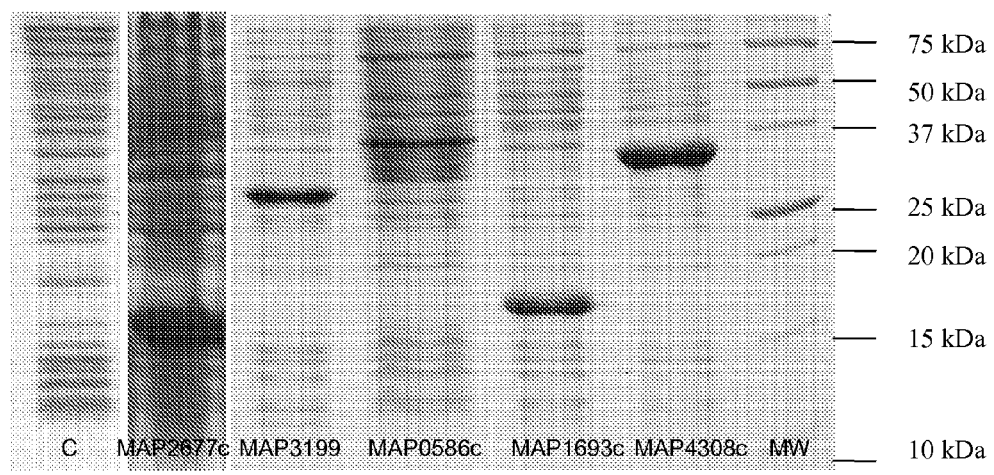
FIG. 2A correspond to the results obtained for MAP0586c, MAP1693c, MAP3199, MAP4308c, MAP2677c.
Figure 2B:
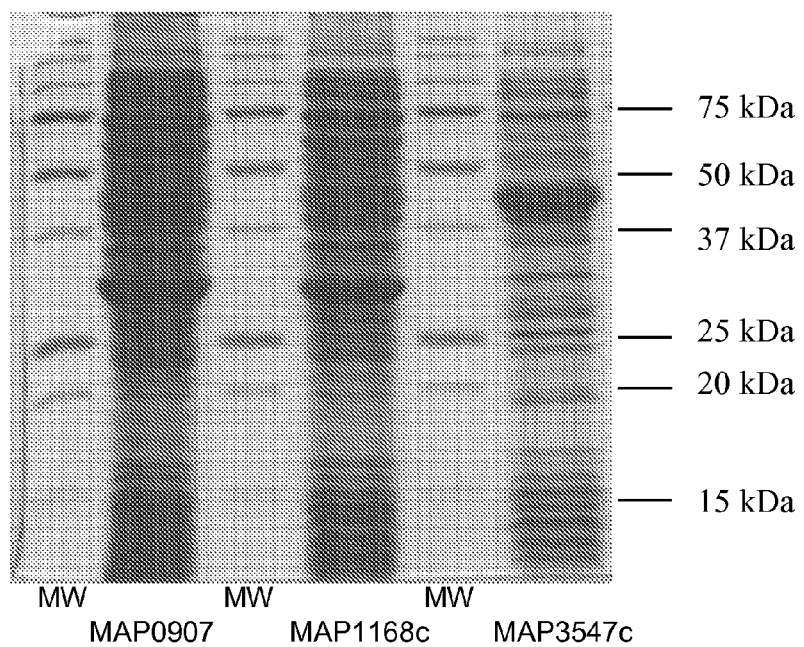
FIG. 2B the results for MAP0907, MAP1168c, MAP3547c.

Both FIG. 1 and FIG. 2 give the pI (scale from 3 to 10 and the molecular weights (in KDa) (scale indicating 150, 100, 75, 50, 37, 25, 20, 15 and 10).

Figure 3:
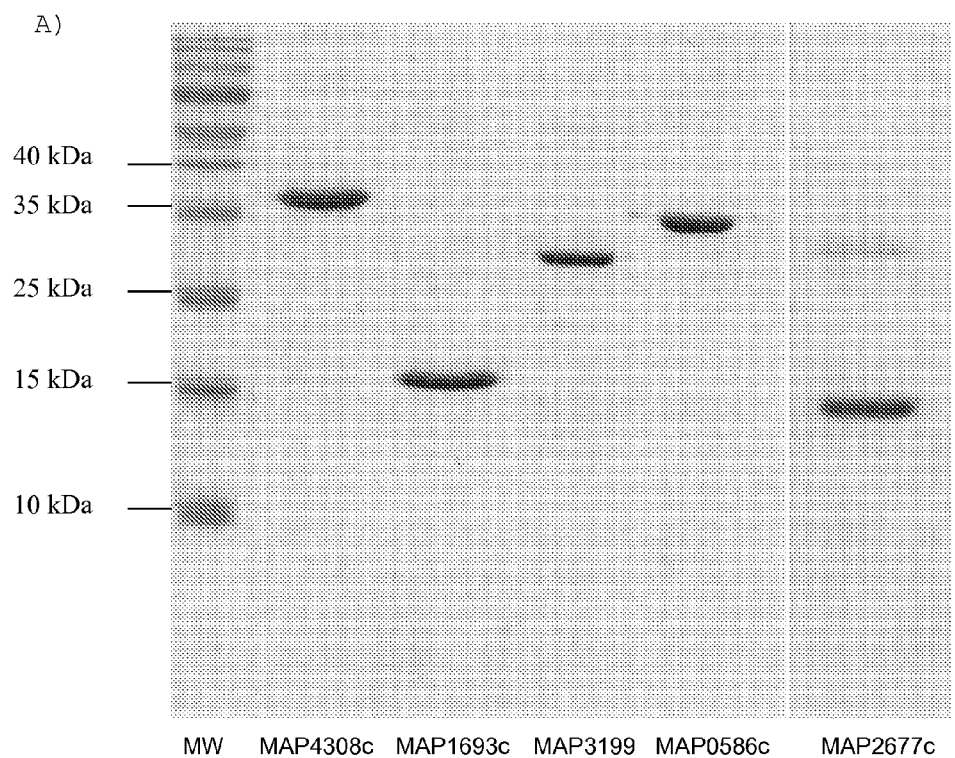
Figure 3:
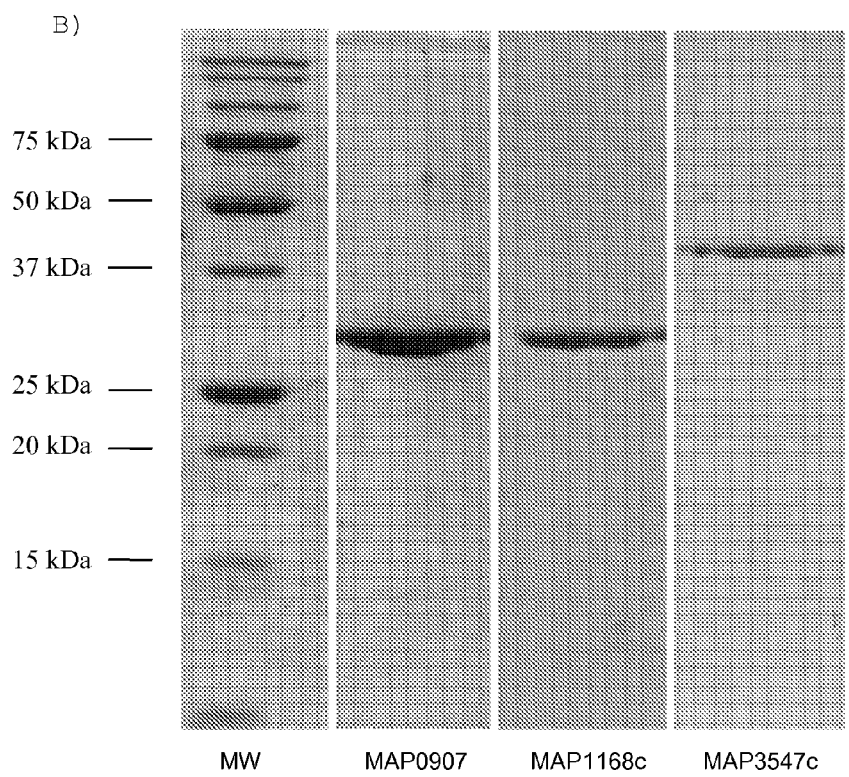

FIG. 3 presents SDS-PAGE electrophoresis results corresponding to candidate antigen purification. Candidate antigens have been purified by IMAC using linear gradient in elution step. MW, molecular weight marker. A) MAP0586c, MAP1693c, MAP3199, MAP4308c, MAP2677c; B) MAP0907, MAP1168c, MAP3547c.

Figure 4:
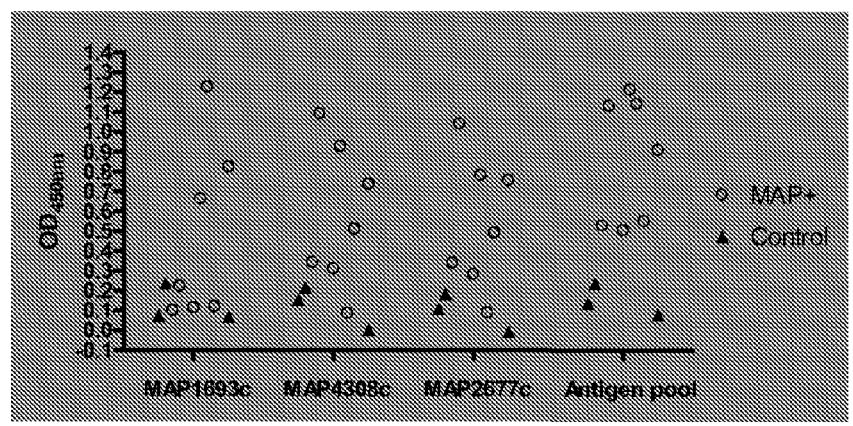

FIG. 4 presents results of ELISA tests for candidate antigens MAP1693c, MAP4308c and MAP2677c. Optical density signals at 450 nm are given for different sera from MAP infected cattle.

Figure 5:
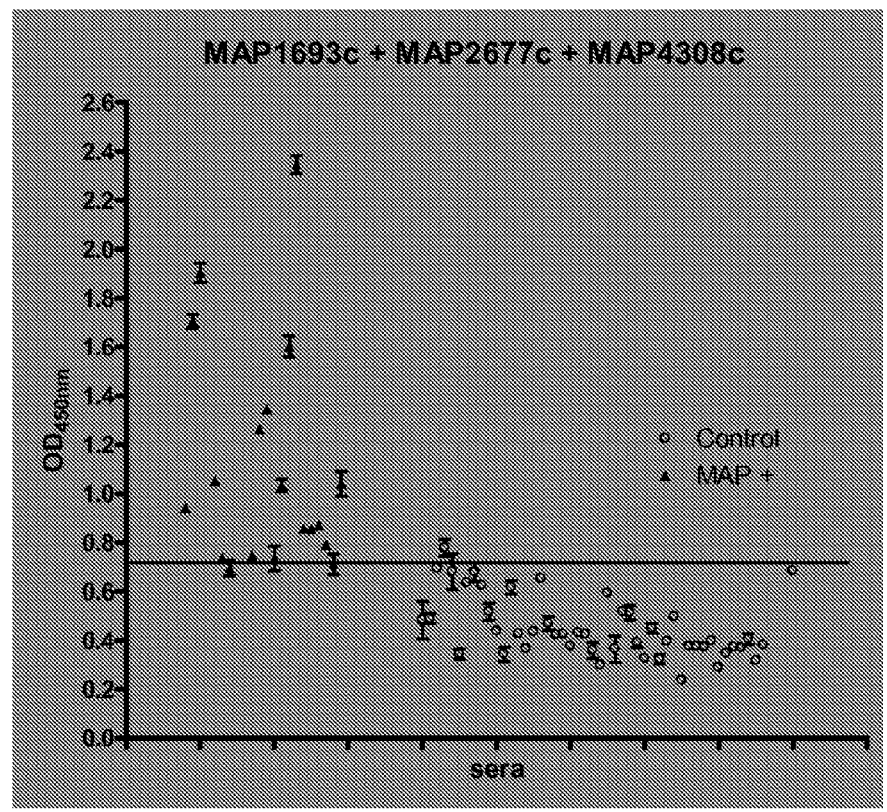
Figure 5:
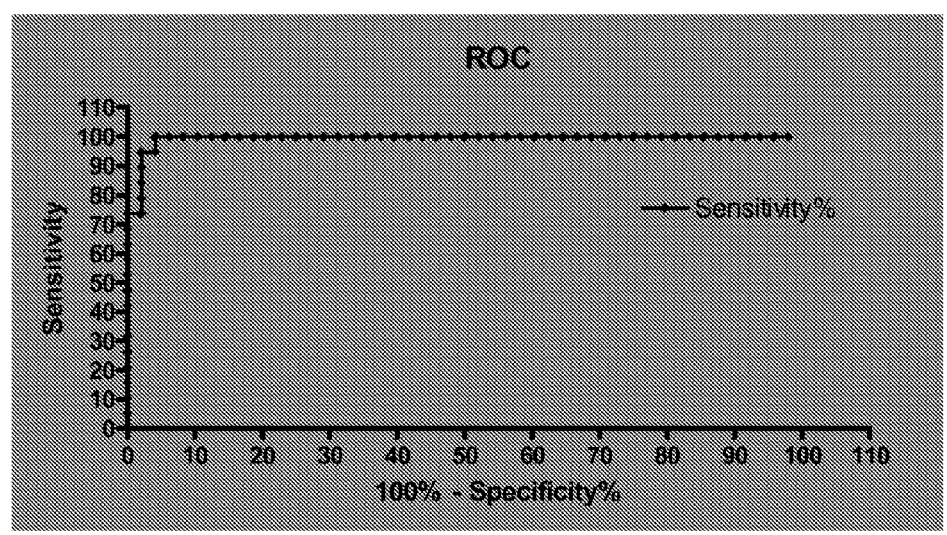
Figure 6A:
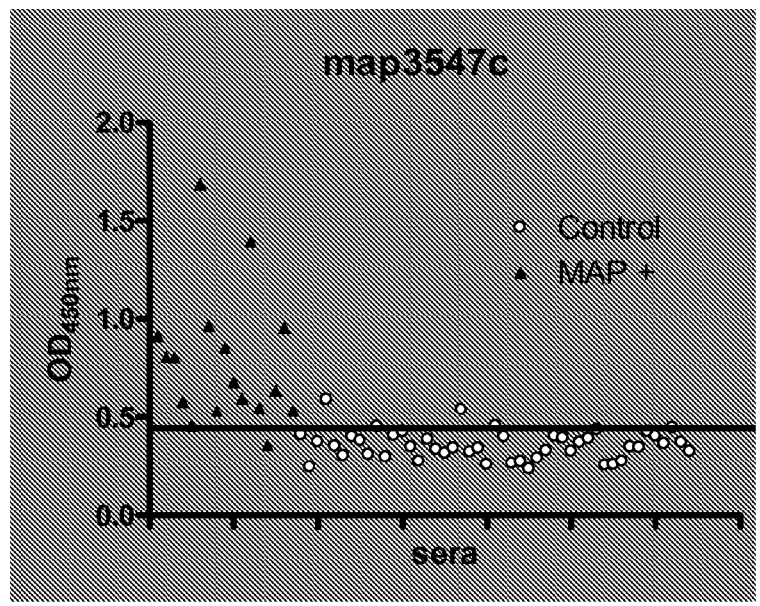
Figure 6A:
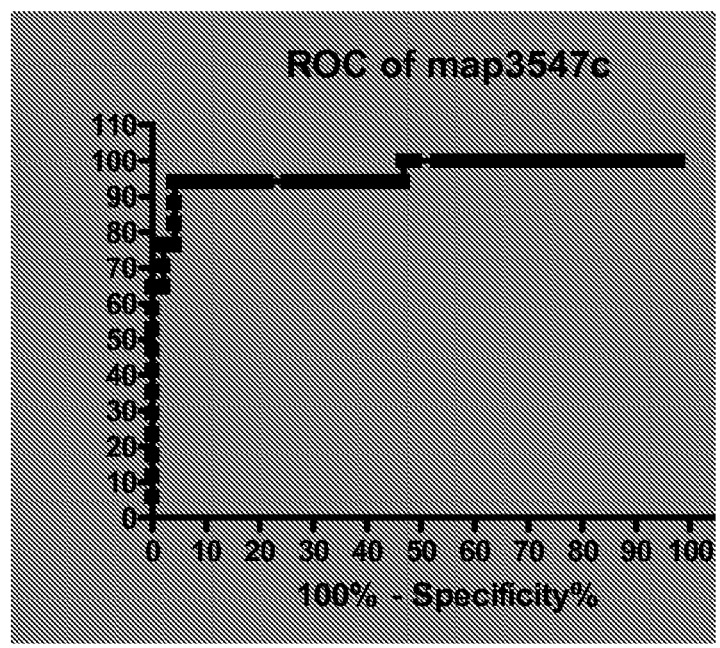
Figure 6B:
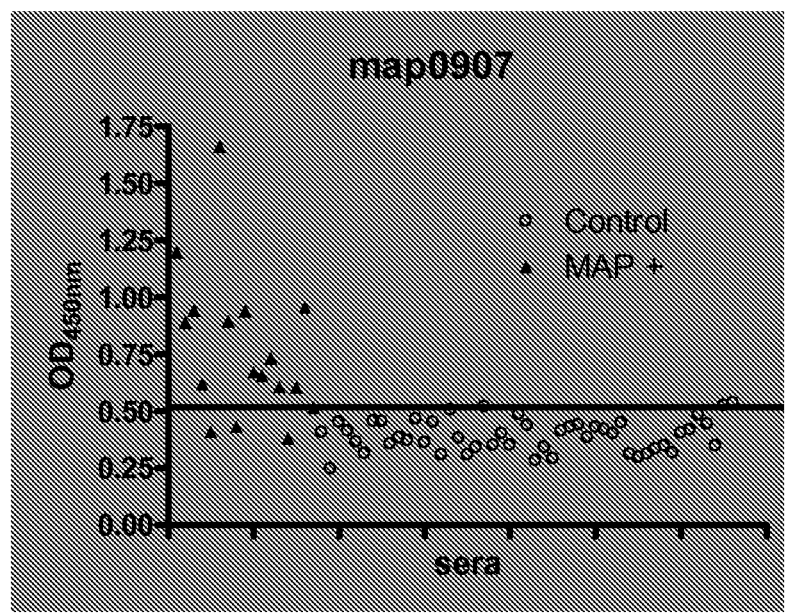
Figure 6B:
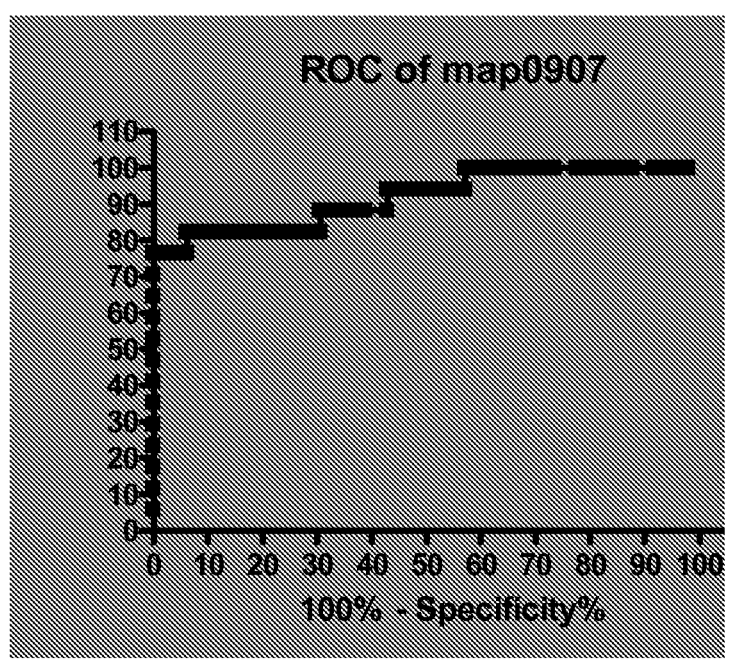

FIG. 5 shows ROC analysis of ELISA using MAP1693c, MAP4308c and MAP2677c in combination.

FIG. 6 shows ROC analysis of ELISA using MAP3547c (FIG. 6A) and MAP0907 (FIG. 6B) individually (separately).

Figure 7A:
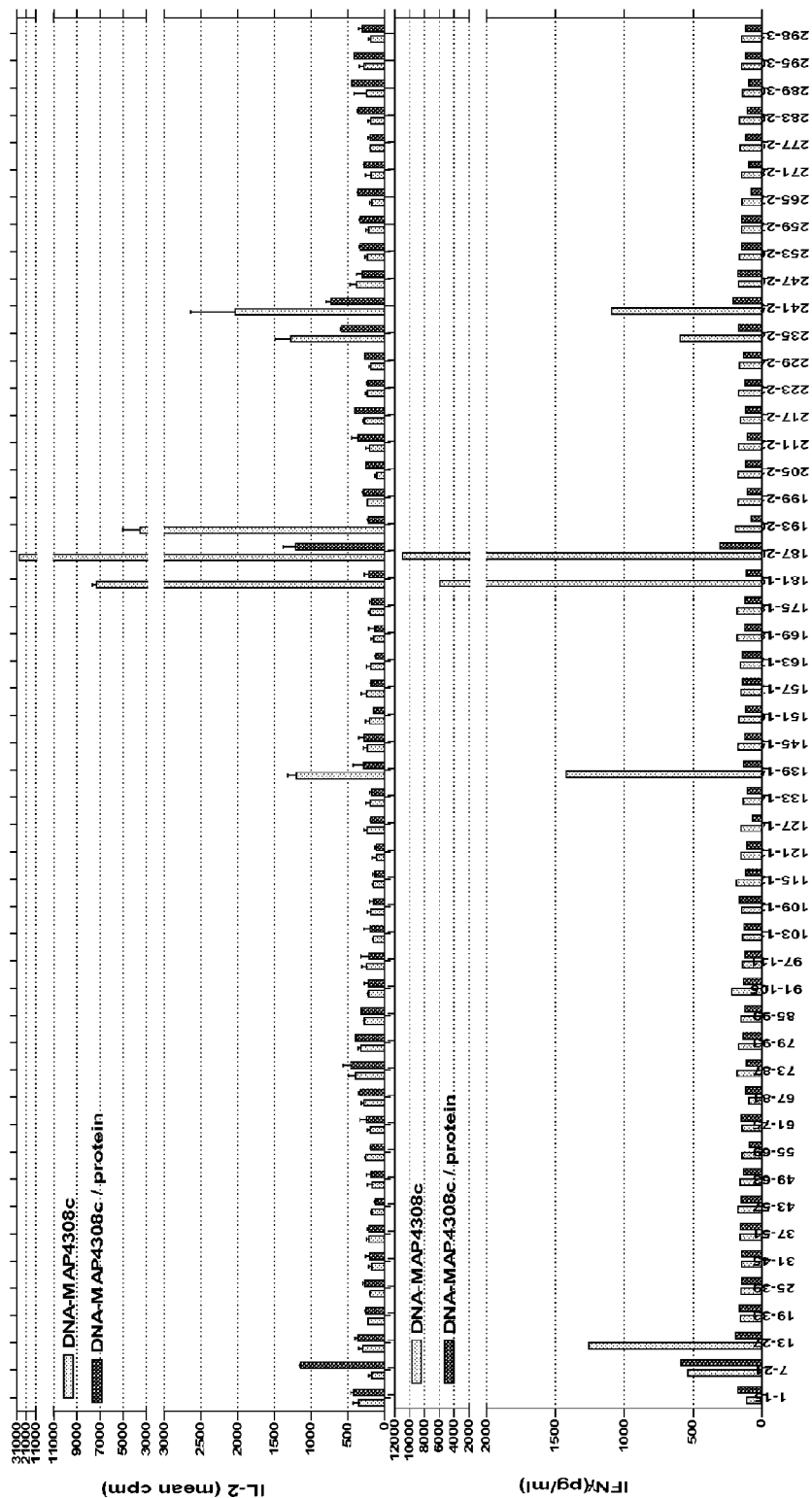

FIG. 7 corresponds to IL-2 and IFN-γ activities as measured in 24- and 72-h spleen cell culture supernatants, respectively, from C57BL/6 (FIG. 7A) or BALB/c (FIG. 7B) mice stimulated with one of the 51 synthetic MAP4308c peptides (10 μg/ml) 15mers with 9 amino acid overlap.

Figure 8A:
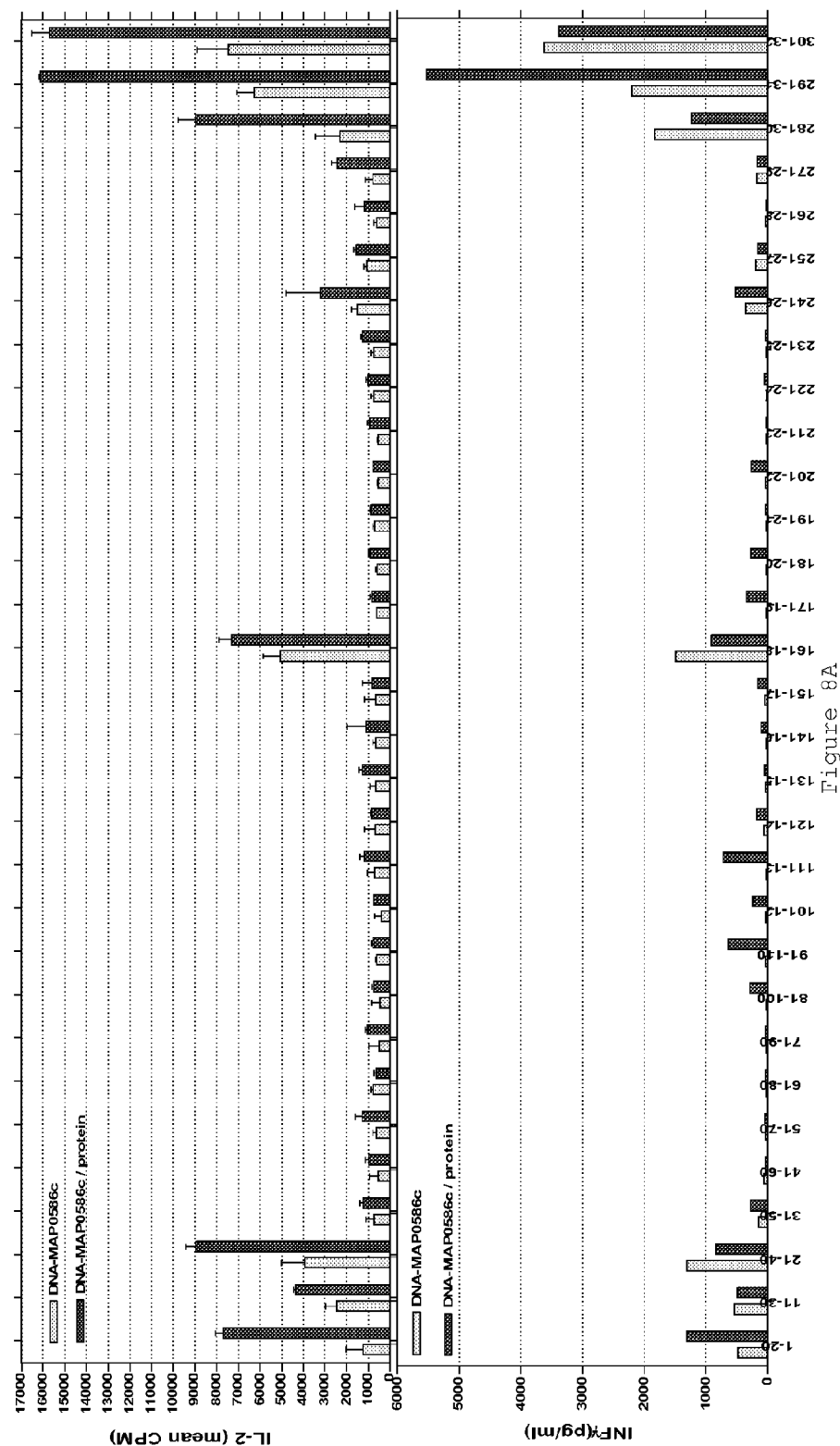
Figure 8B:
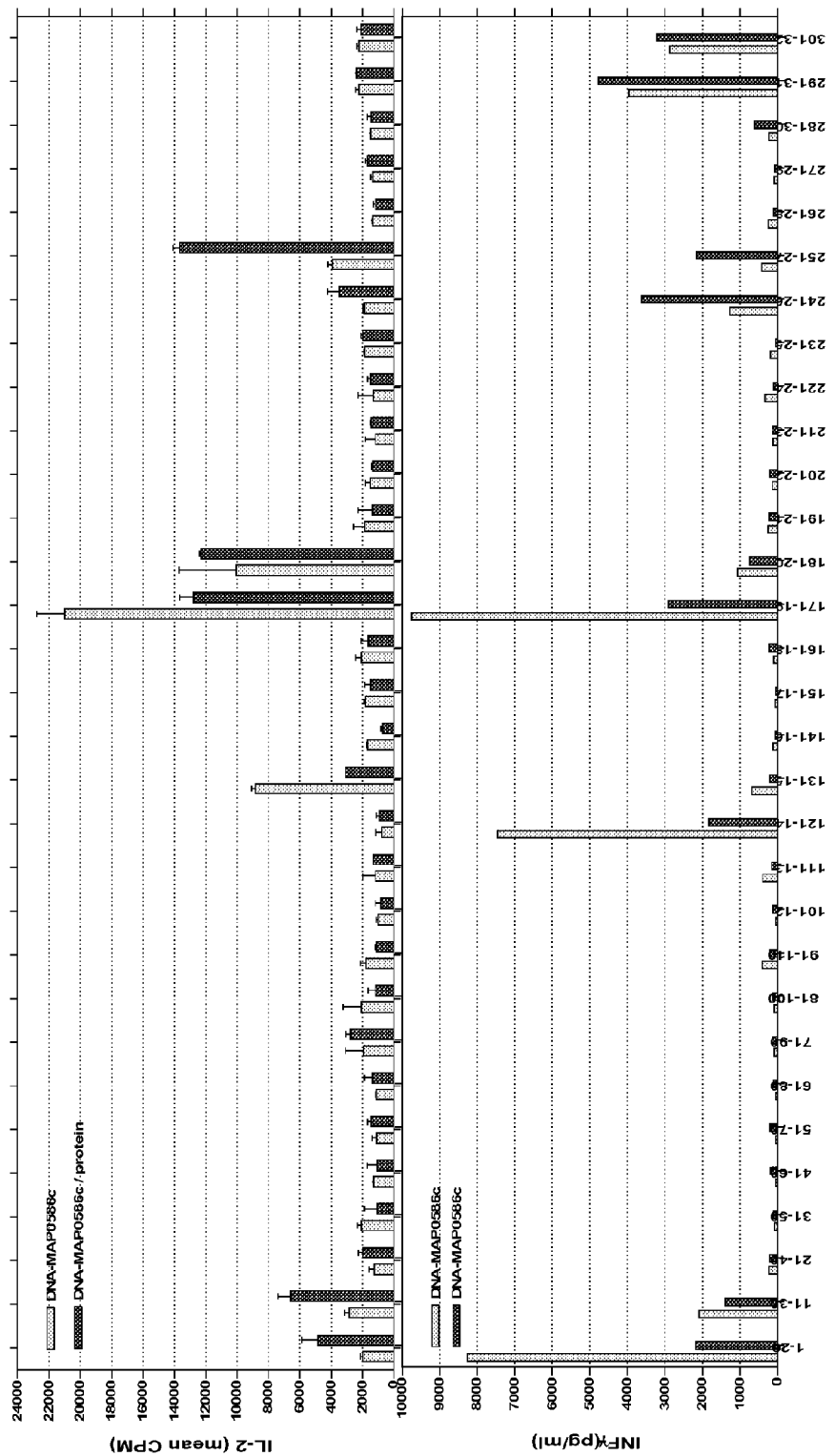

FIG. 8 corresponds to IL-2 and IFN-γ activities as measured in 24-h and 72-h spleen cell culture supernatants, respectively, from C57BL/6 (FIG. 8A) or BALB/c (FIG. 8B) mice stimulated with one of the 31 synthetic MAP0586c peptides (10 μg/ml) 20 mers with 10 amino acid overlap.

Figure 9:
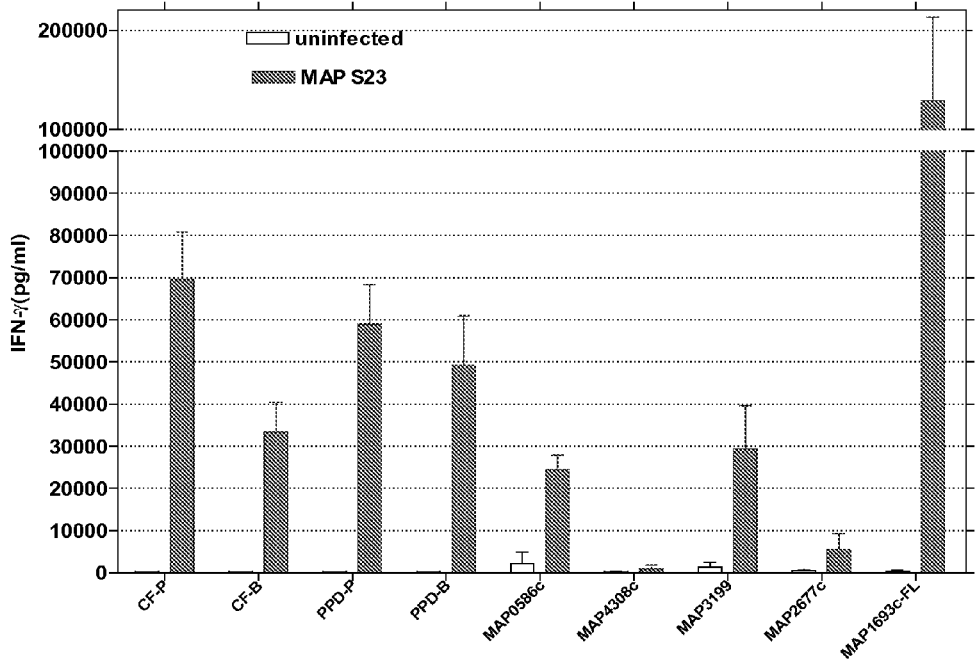

FIG. 9 presents IFN-γ activity as measured in 72-h spleen cell culture supernatants, from four C57BL/6 mice non infected or infected with MAP S23, and Cells were restimulated with CF-P, CF-B, PPD-P, PPD-B, MAP0586c, MAP4308c, MAP3199, MAP2677c and MAP1693c-FL (5 μg/ml) at 12 weeks after infection.

Figure 10:
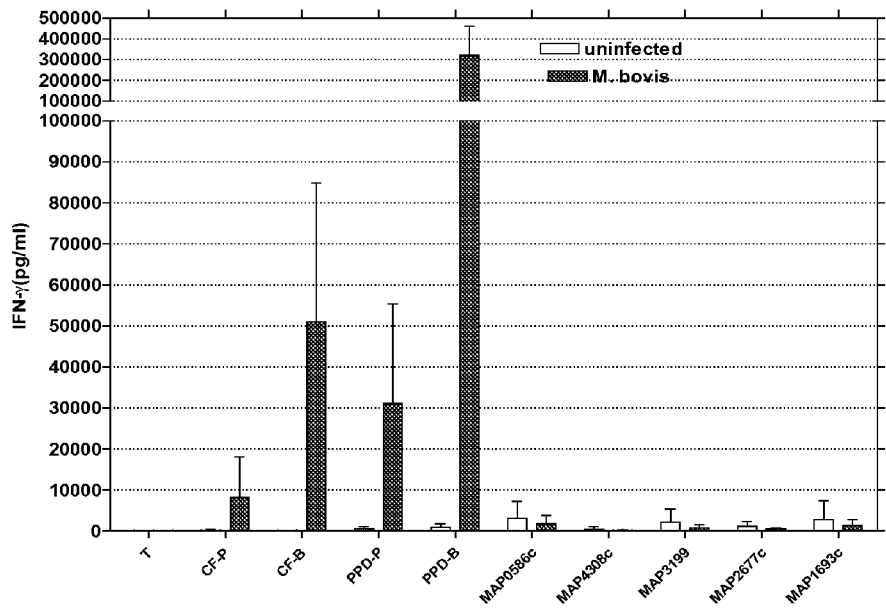

FIG. 10 shows IFN-γ activity as measured in 72-h spleen cell culture supernatants, from two C57BL/6 mice infected with *M. bovis*. Cells were restimulated with CF-P, CF-B, PPD-P, PPD-B, MAP0586c, MAP4308c, MAP3199, MAP2677c and MAP1693c (5 μg/ml) at 12 weeks after infection.

Figure 11:
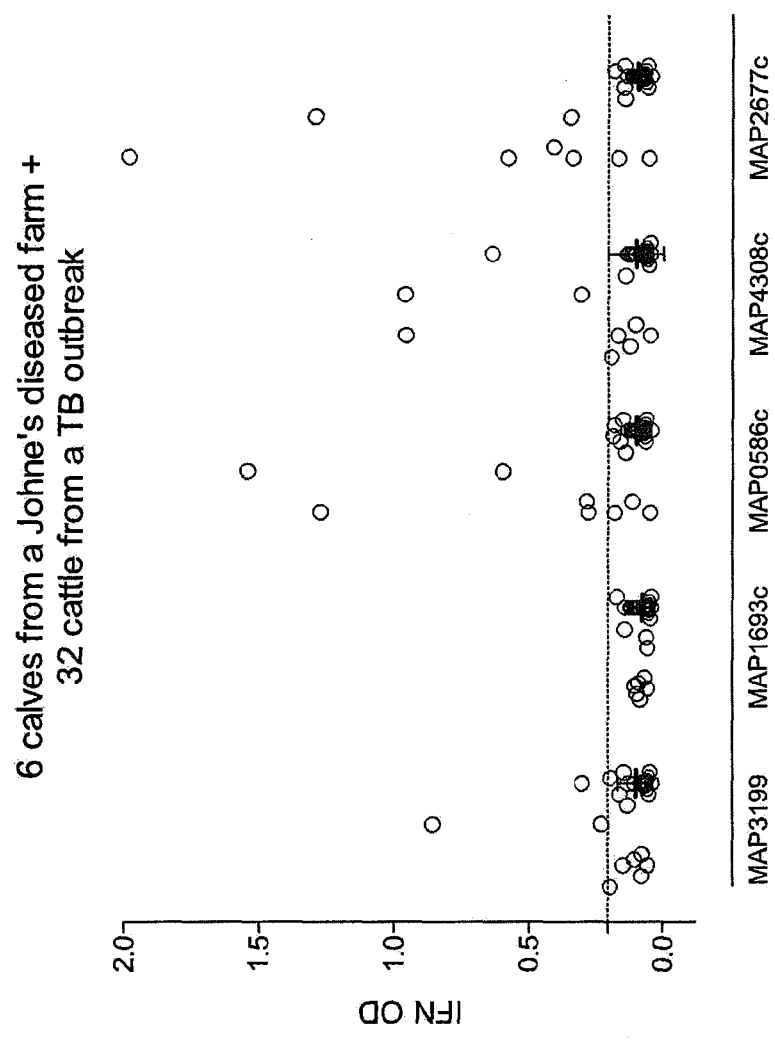

FIG. 11 presents results of ex vivo 20h-IFN gamma test in 32 out of 39 cattle from a culture-confirmed *M. bovis* outbreak (empty circles symbols) and in 6 out of calves from a culture-confirmed Johne's diseased farm (diamond symbols). Only cattle with no background responses (PBS OD<0,150) are shown. Two cattle within the TB outbreak farm classified as paratuberculosis reactors based on the avian and bovine PPDs interpretation criteria (3) are shown separately (black symbols). The positivity cutoff following the supplier's specifications is marked with a dotted line (OD=0,205).

Figure 12:
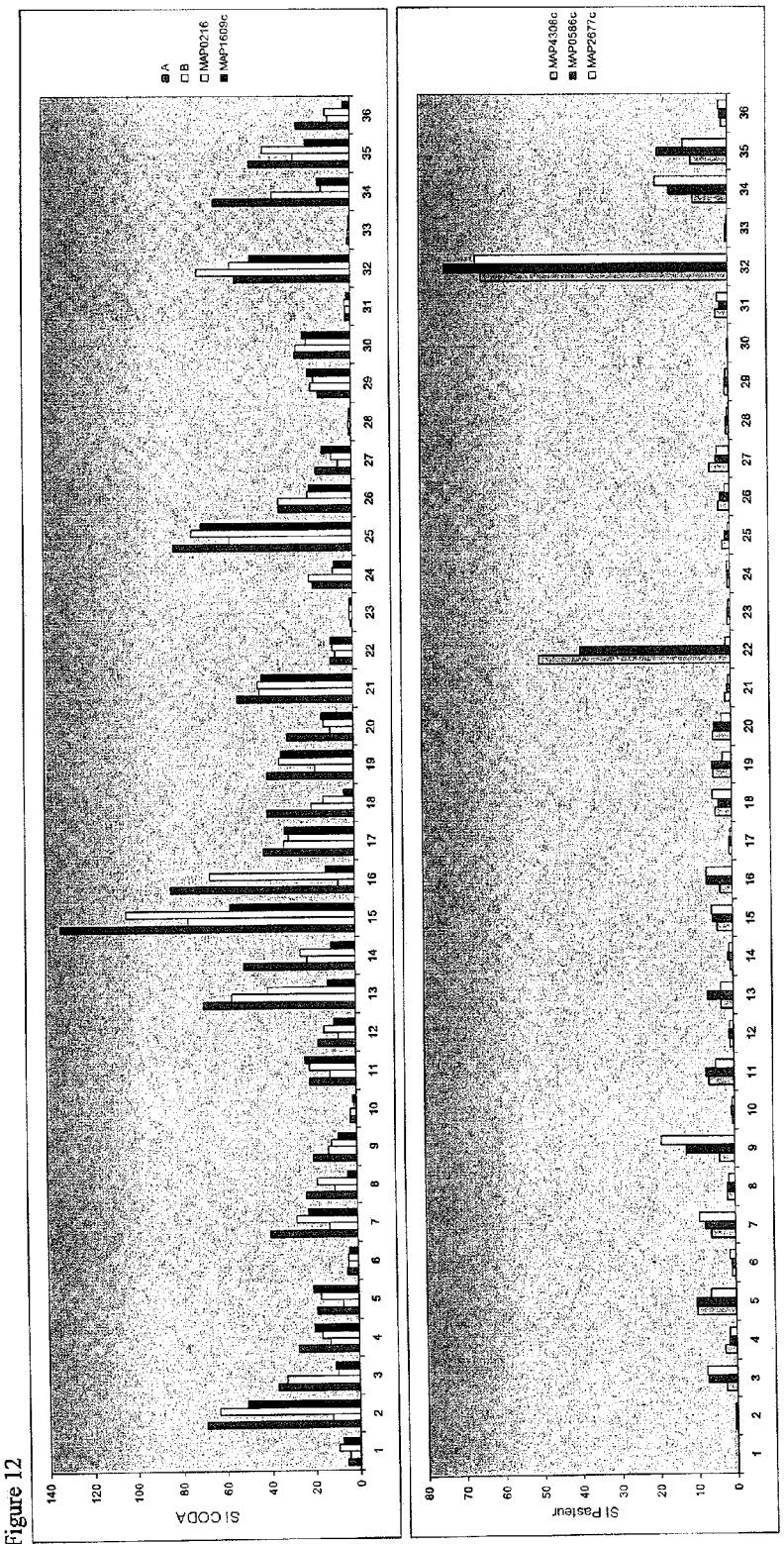

FIG. 12 shows the results of a proliferation assay performed on 36 animals from a paratuberculosis-infected herd. Tritiated thymidine incorporation in whole blood cultures antigen-stimulated for 7 days in vitro. Results expressed as stimulation indexes (SI). All antigens were tested at a 5 μg/ml final concentration except for avian (FIG. 12A, upper panel) and bovine (FIG. 12B, upper panel), PPDs tested at 20 μg/ml. On this FIG. 12, hatched squares correspond to MAP4308c, black squares correspond to MAP0586c, and white squares correspond to MAP2677c.

Figure 13:
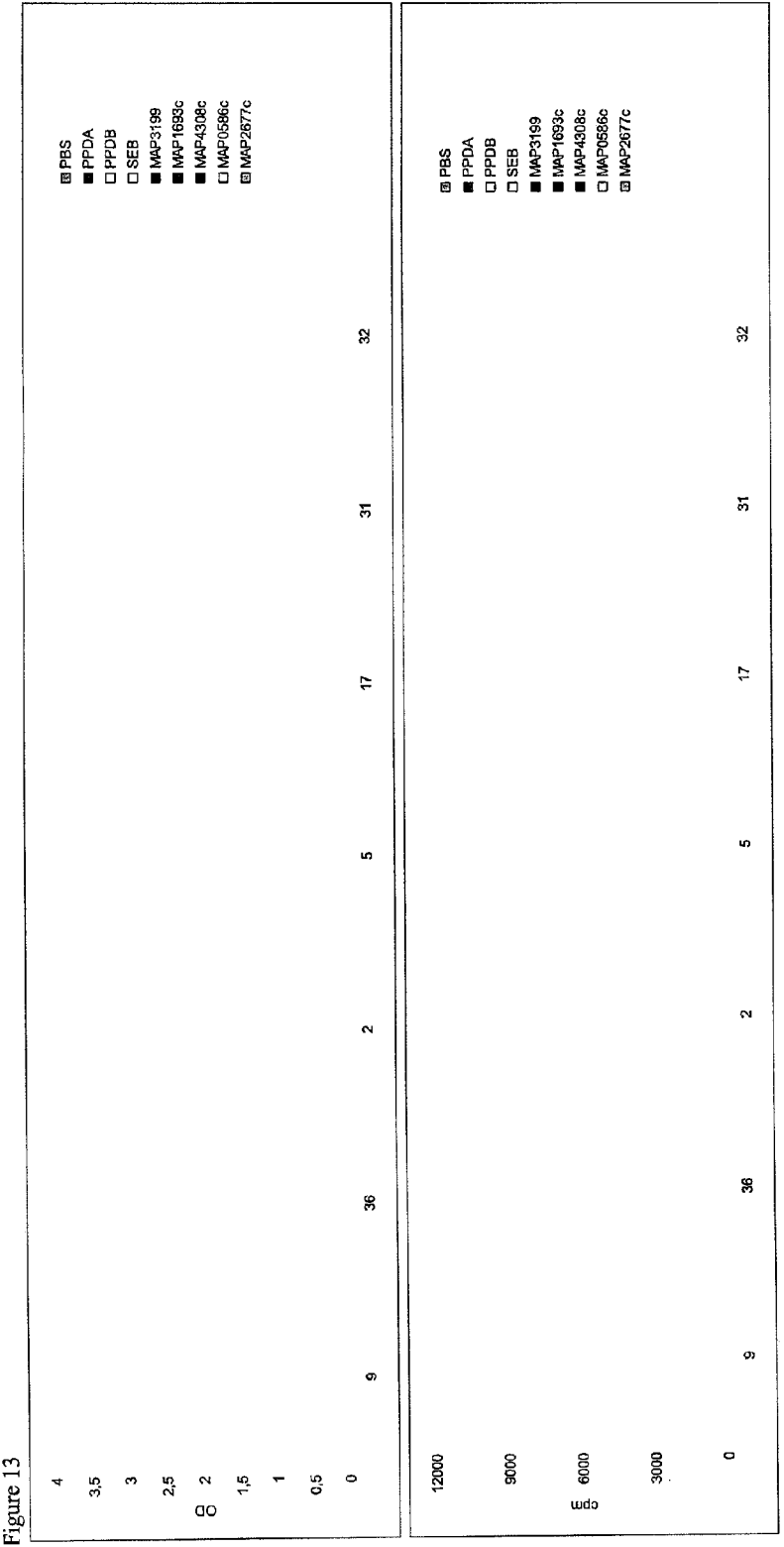

FIG. 13 shows (A) ex vivo 20h-IFNγ responses in seven 2 to 4-month old calves from a culture-confirmed Map herd. Results shown are OD readings in the IFN ELISA with a PBS negative control, avian (PPDA) and bovine PPDs, a staphylococcal enteroxin β (SEB) positive control and the tested antigens (B) Proliferation assay of the same animals. Tritiated thymidine incorporation in whole blood cultures antigen-stimulated for 7 days in vitro. Results are expressed as cpm±SD. All antigens were tested at a 5 μg/ml final concentration except for avian (PPDA) and bovine (PPDB) PPDs tested at 20 μg/ml.

Figure 14:
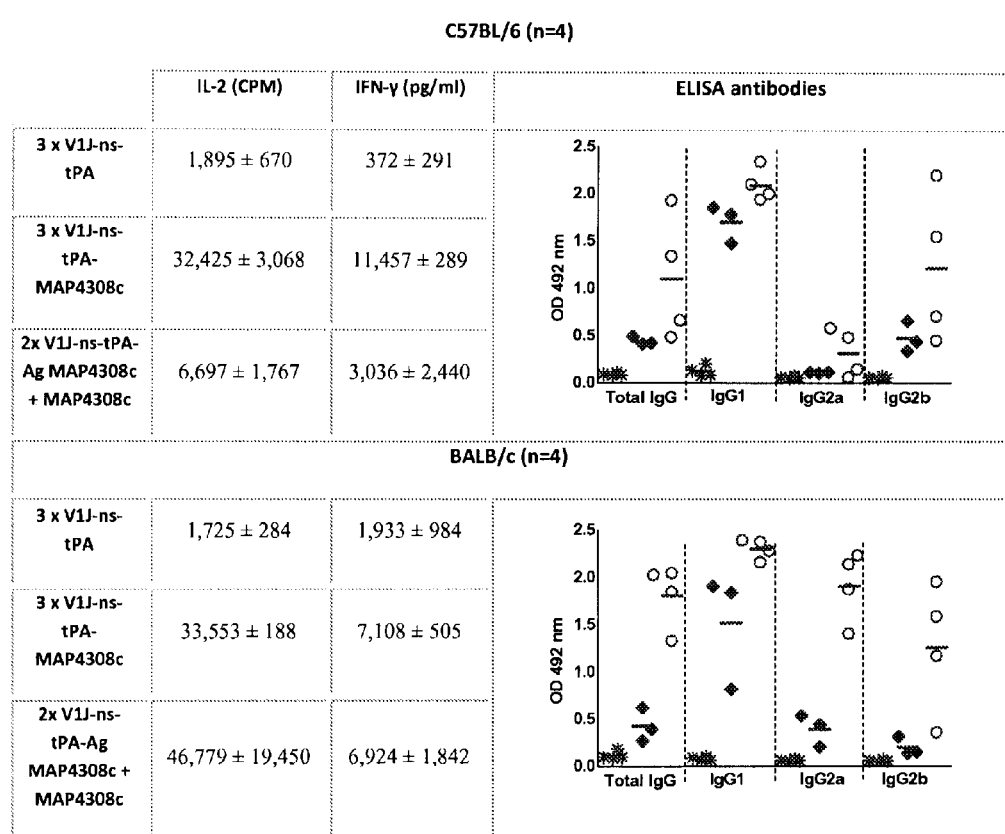

FIG. 14 shows IL-2 and IFN-γ activities as measured in 24- and 72-h spleen cell culture supernatants, respectively, from C57BL/6 or BALB/c mice stimulated with MAP4308c (5 μg/ml). ELISA antibodies: total IgG, IgG1, IgG2a and IgG2b antibody response against purified protein MAP4308c (500 ng/ml) in sera from C57BL/6 or Balb/c vaccinated with empty DNA (stars), DNA-MAP4308c (losange) and DNA-MAP4308c boosted with recombinant protein (circle). Sera were collected 3 weeks after the last immunization and tested at a 1:1600 dilution.

Figure 15:
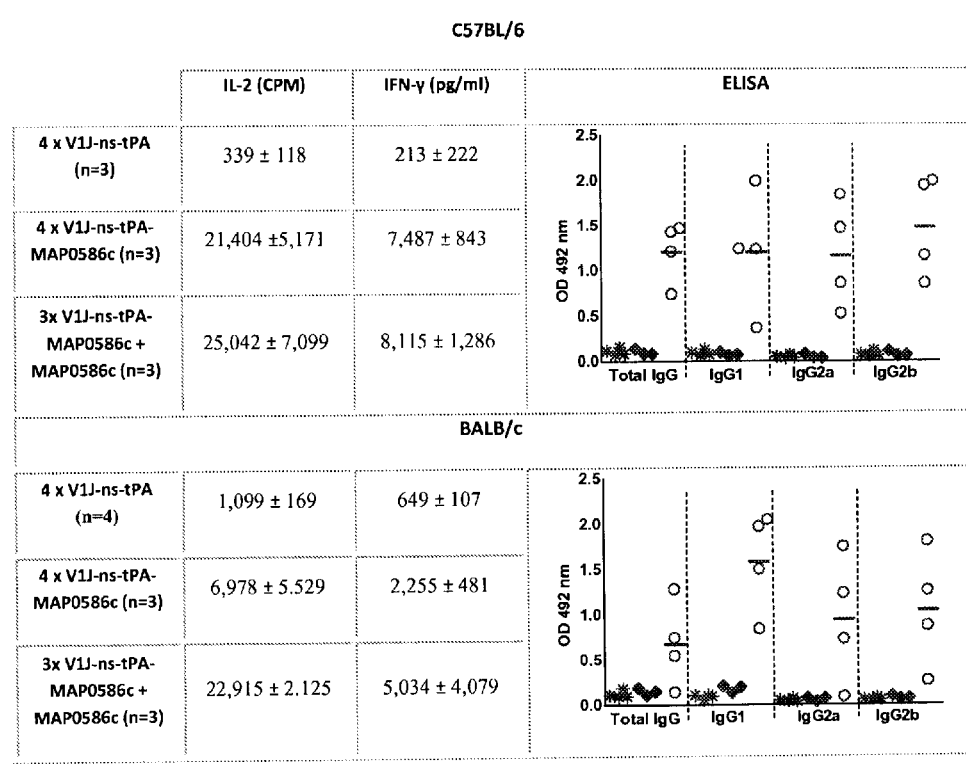

FIG. 15 shows IL-2 and IFN-γ activities as measured in 24- and 72-h spleen cell culture supernatants, respectively, from C57BL/6 or BALB/c mice stimulated with MAP4308c (5 μg/ml). ELISA antibodies: total IgG, IgG1, IgG2a and IgG2b antibody response against purified protein MAP4308c (500 ng/ml) in sera from C57BL/6 or Balb/c vaccinated with empty DNA (stars), DNA-MAP4308c (losange) and DNA-MAP4308c boosted with recombinant protein (circle). Sera were collected 3 weeks after the last immunization and tested at a 1:1600 dilution.

DETAILED DESCRIPTION OF THE INVENTION

1.—Materials and Methods:
Sample Preparation for Proteomic Analysis

Crude extract (CE): the MAP type strain ATCC19698 was grown as a surface pellicle at 39° C. in mycobactin J-supplemented synthetic Sauton medium to stationary phase as described previously (1). Cells were harvested by centrifugation were washed three times. An equivalent volume of 106 μm glass beads was then added and the sample homogenized for 2 minutes in a Mini-beadbeater (Biospec Product, Bartlesville, USA). After one freeze/thaw cycle and a 2 minute sonication, centrifugation was performed to recover the supernatant.

Culture filtrates (CF): MAP strain ATCC19698 was grown as a surface pellicle on mycobactin J-supplemented Sauton medium for 4 weeks at 39° C. Culture filtrates were separated from bacteria by filtration and proteins were recovered by ammonium sulphate precipitation.

Protein concentration in culture filtrates and extracts was determined using the Bio-Rad protein Assay Kit (Bio-Rad laboratories, USA).

Proteomic *Mycobacterium avium* subsp. *paratuberculosis* Secretome Analysis

The MAP secretome from CF was analysed by SDS-PAGE and by two-dimensional gel electrophoresis (2-DE), followed by the systematic identification of all Coomassie Blue-stained protein bands/spots by mass spectrometry.

For SDS-PAGE, CF samples were diluted in Laemmli sample buffer and 50 μg of proteins were electrophoretically separated on a 12% vertical acrylamide gel (Hoefer, Amersham Bioscience) at 250 V, 40 mA.

For 2-DE, MAP CF proteins were precipitated a second time using TCA, and pellets were solubilized in a minimal volume of sample buffer (7 M urea, 2 M thiourea, 4% (w/v) CHAPS and 50 mM DTT), and cleared by centrifugating at 18000×g. For the first dimension, 500 μg of proteins were subjected to isoelectric focusing on immobilized pH gradient (IPG) strips (pH 3-10; NL; 11 cm; Amersham Pharmacia Biotech, Sweden). The first-dimensional isoelectric focusing was carried out as previously described (2). The second dimension vertical slab SDS-PAGE was run about 4 hours at 30 mA/gel using the Criterion apparatus (Bio-Rad laboratories, USA) and pre-cast gradient gels (10-20%).

The SDS-PAGE and 2-DE gels were stained with Coomassie brilliant blue R-250 (Amresco, Solon, Ohio, USA).
Protein Identification by Mass Spectrometry Protein bands/spots were excised and submitted to trypsinolysis as described previously (2). For MALDI-TOF analysis, 1 μl of each sample was mixed with 1 μl of matrix (5 mg/ml α-cyano-4-hydroxycinnamic acid and 0.5 μmol/μl rennin as internal standard, in 25% (v/v) ethanol, 25% (v/v) acetonitrile, 0.05% (v/v) TFA), then spotted onto a MALDI sample plate and allowed to air dry. MALDI-TOF was performed using a MALDI™ mass spectrometer (Micromass, Manchester, UK) equipped with a 337 nm nitrogen laser.

The resulting peptide masses were automatically searched for in a local copy of the SWISS-PROT, TREMBL databases using the ProteinLynx global server and the Protein Probe (Micromass Ltd., Manchester, UK) and/or Mascot (http<:>//www<.>matrixscience<.>com) search engines.

For Electro-Spray Ionization Mass Spectrometry (ESI-MS) and collision-induced dissociation Mass Spectrometry (MS/MS) analysis, peptides were extracted from gel pieces in 25 mM $NH_3HCO_3$, 50% (v/v) $CH_3CN$, 5% (v/v) formic acid, and dried in a speed vacuum. After reconstitution in 5% (v/v) formic acid, ESI-MS and MS/MS were performed with a Q-TOF 2 mass spectrometer (Micromass, Manchester, UK) equipped with a Z-spray nanoflow electrospray ion (nanoESI) source and a high-pressure collision cell. Amino acid sequences were manually deduced with the assistance of Micromass' peptide sequencing program PepSeq (BioLynx, Micromass Ltd., Manchester, UK). Searches for protein identity from sequence data were performed using the BLASTP algorithm using the SWISSPROT or TREMBL databases. The search was carried out in all species.
Animal Sera Positive reference sera used in the ELISA and immunoproteomics tests were from 21 naturally infected cows shedding MAP at the time of sampling, as shown by faecal culture (see table 7).

Immunoproteomic analysis was performed with two of the 21 positive sera and one 11-month-old calf infected intravenously with $10^8$ CFU of MAP ATCC 19698 as described previously (1). All three animals tested at post-mortem, were positive in bacterial culture and presented strong seroconversions in *M. phlei*-adsorbed LAM-based (9), and commercial crude cell extract based, ELISAs (Pourquier, France). Three sera, originating from animals experimentally infected by *M. bovis*, were used for the specificity selection. These sera originated from cattle infected intra-tracheally with 106 CFU of a low passage field strain of *M. bovis*, sampled and confirmed infected at week 13 post-infection by post-mortem and bacterial culture, and presenting at that time strong serological responses in the LAM ELISA, as described previously.
Immunoproteomic Analysis of MAP Culture Filtrate 100 μg of MAP CF or CE were separated by 2-DE as described above and blotted on nitrocellulose membrane (Hybond ECL; AP biotech) After wash in PBS and saturation using BSA, membrane was incubated overnight with primary antiserum preabsorbed on MAP lipidoarabinomannan. Membrane was rinsed before incubation with the secondary antibody (rabbit anti-bovine, HRP-conjugated; PIERCE). Immunoreactive proteins were detected by a chemiluminescence detection kit (Lumi-light Western blotting substrate, ROCHE) following manufacturer's instructions and identified by mass spectrometry.

In this context, three positive sera were used: two came from naturally and one from experimentally MAP infected animals tested positive in faecal culture test and presenting a high respond in a commercial ELISA test (Pourquier, France). Negative sera used for specificity selection came from three animals experimentally infected intratracheally with $10^6$ cfu of a low passage field strain of M. bovis (3).

Candidate Antigen Cloning

Candidate antigens were selected based on two criteria: prospective specificity in BLAST searches, and antigenicity in immunoproteomic analysis. Specific proteins selected in the CF database were blasted against the complete M. bovis and the unfinished M. avium subsp. avium genomes (TIGR server). Antigenic proteins were selected by immunoproteomic approach in MAP CF and CE. Only proteins recognized by at least two of the three MAP-positive sera and by none of the three sera of M. bovis infected animals, were selected.

Genes encoding candidate antigenic proteins were amplified by PCR from MAP genomic DNA using primers derived from the MAP genomic sequence. Amplified fragments were purified by agarose gel separation followed by purification using a QIAkit PCR kit (QIAGEN). Purified amplicons were ligated into a pQE-80L (QIAGEN) expression vector.

Candidate Antigen Expression and Purification

Recombinant Protein Expression:

Culture of E. coli transformants containing the selected construct was grown to an optical density of 0.6. Recombinant protein expression was then induced by adding 1 mM IPTG in overnight culture at 37° C. Cells were harvested by centrifuging 15 minutes at 5000 g at 4° C.

Recombinant Protein Extraction:

Harvested cells were lysed in lysis buffer (50 mM Tris-HCl, pH 7.5, 500 mM NaCl, 8 M urea, 10 mM Imidazole), and lysozyme (Novagen) was added. Samples were sonicated and subsequently incubated for 15 minutes. Nucleic acids were digested by addition of 5 µl benzonase (25.0 U/µl, Novagen). Supernatants were finally clarified by ultracentrifugation at 110000×g at 4° C. for 40 min.

Recombinant Protein Purification:

A His-Select column (6.4 ml, Sigma) was used with a constant flow rate of 3 ml/min and a sample collector (FC250, Gilson) programmed to collect 3-ml fractions. Non-binding proteins were removed by washing with 45 ml of lysis buffer. A 10 to 300 mM linear gradient of imidazole in a total volume of 100 ml was used for protein elution. Contents of collected fractions were analyzed by SDS-PAGE followed by Coomassie brilliant blue staining. Fractions containing the recombinant protein were pooled and extensively dialysed against 10 mM PBS, pH7.2, containing 0.1 M urea. After concentration by ultrafiltration (Ultracel 5 kDa, Amicon, Millipore, USA) and protein quantification in an assay (Bio-Rad protein Assay Kit, Bio-Rad laboratories, USA), samples were stored at −80° C. until use.

ELISA

Flat-bottom 96-well plates (Maxisorp, Nunc) were coated overnight with 50 µl of each recombinant protein diluted to 5 µg/ml in 37% formaldehyde. After PBST wash (100 mM PBS, pH 7.2, 0.05% (v/v) Tween 20) and uncoated sites blocking with 5% (w/v) casein hydrolysate in PBST, 50 µl of primary antibodies (bovine sera diluted 250× in PBST, 1% (w/v) casein) were then added to the plate and incubated for 1 hour at 37° C. After wash with PBST, 50 µl of secondary antibody (HRP-conjugated goat anti-bovine immunoglobulin, Sigma, diluted 25000× in PBST, 1% (w/v) casein), were added to each well for 1 hour at 37° C. After wash with PBST, peroxidase activity was detected by adding 75 µl of TMB (3,3',5,5'-tetramethylbenzidine, liquid substrate system, Sigma). After 10 minutes, reaction was stopped by addition of 35 µl 1N $H_2SO_4$, and OD was read on a Bio-Tek plate reader at 450 nm.

Sample Preparation for Vaccination Purposes

M. avium subsp. paratuberculosis (MAP) ATCC 19698 was purchased from the American Tissue Culture Collection and was grown at 39° C. for 4 weeks as a surface pellicle on synthetic Sauton medium supplemented with mycobactin J (2 µg/ml) (Synbiotics Europe) as described previously (4). Culture filtrate (CF-P) was separated from the bacteria; CF proteins were precipitated by ammonium sulphate and extensively dialyzed against phosphate-buffered saline (PBS). CF-B of M. bovis (AN5) was obtained from M. bovis cultures grown as surface pellicle for 2 weeks at 37° on synthetic Sauton medium. PPD-B from M. bovis Vallée was kindly given to us by the late Dr. J. Nyabenda (WIV-Pasteur Institute Brussels). PPD-P was prepared from 6-8 week old cultures of M. avium subsp paratuberculosis strain ATCC 19698 as described before (8).

Preparation of Genomic DNA from M. avium subsp. paratuberculosis ATCC 19698.

Genomic DNA of M. avium subsp. paratuberculosis ATCC 19698 was prepared as described previously by Tanghe et al. for M. ulcerans (5).

Plasmid Constructions

Modification of V1J.ns-tPA into V1J.ns-tPA-his

A six histidine tag was inserted in 3' position of the BglII restriction site of the V1J.ns-tPA vector (Merck Research Laboratories, Pa., USA).

DNA Vaccines

After this modification, genes encoding 5 MAP proteins were amplified by PCR and cloned in directional sense BglII 5' and EcoRI 3'.

Primers used for PCR are disclosed in Table 4. Genes were amplified from M. avium subsp. paratuberculosis ATCC19698 genomic DNA using primers (Proligo) derived from sequences of MAP K-10.

PCR fragments were purified on column ("QIAquick PCR Purification", Qiagen), and ligated into a V1.Jns-tPA-his vector predigested with EcoRI/BglII and dephosphorylated with the Shrimp phosphatase (Roche). After ligation (T4 DNA ligase, Fermentas) and transformation into DH5-α chemically competent E. coli cells (Invitrogen), positive clones were selected on LB-kanamycin medium (50 µg/mL) and confirmed by restriction enzyme digestion.

The integrity of cloned sequences was checked by sequence analysis.

V1J.ns-tPA-his vectors encoding these proteins were purified with PureLink™ HiPure Plasmid DNA Gigaprep kit" (Invitrogen).

Recombinant Proteins.

Recombinant MAP proteins were expressed and purified using pQE-80L vector. Recombinant proteins were expressed as his-tagged proteins in Top-10F' E. coli after IPTG induction and purified by affinity chromatography on immobilized nickel-chelate (Ni-NTA) column as described before (4).

Coding sequences were subcloned by PCR amplification (Expand High Fidelity PCR System, Roche) from V1.Jns-tPA-his-MAP0586c, V1.Jns-tPA-his-MAP4308c, V1.Jns-tPA-his-MAP2677c, V1.Jns-tPA-his-MAP3199 and V1.Jns-tPA-his-MAP1693c vector using primers derived from sequences of MAP K-10.

Genes encoding for MAP0907 and MAP1168c were isolated by PCR from MAP genomic DNA or by PCR on colony for amplification of MAP3547c gene as described before (6). Primers Sequences are given in Table 5.

PCR fragments were purified on agarose gel (QTAkit PCR kit, Qiagen), and ligated into a pQE-80L (Qiagen) expression vector predigested with BamHI/HindIII. After ligation (T4 DNA ligase, Fermentas) and transformation into Top-10F' chemically competent *E. coli* cells (Invitrogen) for expression, positive clones were screened on LB-ampicillin medium (100 μg/mL) and confirmed by restriction enzyme digestion.

The integrity of cloned sequences was checked by sequence analysis.

Vaccination Protocols

Female BALB/c and C57BL/6 (B6) mice were bred in the Animal Facilities of the WIV-Pasteur Institute in Brussels, Belgium, from breeding couples originally obtained from Bantin & Kingman (United Kingdom). All animals were 6 to 8 weeks old at the start of the experiments.

Mice were anesthetized with ketamine/xylazine and injected intramuscularly in both quadriceps muscles with 2×50 μg of control V1J.ns-tPA (without histidine tag) or V1J.ns-tPA-his-Antigens.

For MAP4308c, MAP0586c and MAP1693c-FL, a combined DNA prime-protein boost protocol was compared to an exclusive DNA vaccination protocol. For the protein boost immunization, mice were injected at the last time point with 20 μg of purified protein emulsified in incomplete Freund adjuvant (IFA) in a volume of 100 μl subcutaneously (s.c.) in the back. Recombinant proteins used in protein boost were obtained as described under the subsection "candidate antigen expression and purification".

Antibody ELISA.

Sera from C57BL/6 and BALB/c mice vaccinated with V1J.ns-tPA control vector, V1.Jns-tPA-his-MAP0586c, V1.Jns-tPA-his-MAP4308c were collected by tail bleeding three weeks after the last immunization.

Levels of total immunoglobulin G (IgG) and IgG1, IgG2a and IgG2b specific antibodies were determined by an enzyme-linked immunosorbent assay (ELISA) on individual sera, using purified recombinant antigens (obtained as described under the subsection "candidate antigens expression and purification") for coating (500 ng/well), Peroxidase-labeled rat anti-mouse IgG, IgG1, IgG2a, IgG2b (Experimental Immunology Unit, Universite Catholique de Louvain, Brussels, Belgium) were used as secondary antibody and orthophenyldiamine (Sigma) for revelation. Data are presented as the optical density at 492 nm (OD492) for a serum dilution of 1:1600.

Cytokine Production.

Splenocytes was obtained as described before (4). Indomethacin (1 μg/ml; Sigma) was added to the medium only for infected mice. Cells were incubated with purified recombinant antigens (obtained as described under the subsection "candidate antigens expression and purification") (5 μg/ml) or synthetic peptides (10 μg/ml).

The LPS eventually contaminating recombinant proteins were eliminated using "endotrap" column (Cambrex) following manufacturer instructions.

Spleens from individual mice were tested for response against whole protein, and spleens were pooled for peptide testing.

Culture supernatants were harvested after 24 h for interleukin-2 (IL-2) assays and after 72 h for IFN-γ assays, when peak values of the respective cytokines can be measured. Supernatants were stored frozen at −20° C. until testing.

Peptide Synthesis (ProImmune).

Peptides spanning of the entire MAP0586c sequence were synthesized as 20-mer peptides overlapping by 10 residues.

Peptides spanning the entire MAP4308c sequence were synthesized as 15-mer peptides overlapping by 9 residues.

Murine IL-2 and IFN-γ Assays.

IL-2 and INF-γ were tested as described before (4).

*Mycobacterium avium* subsp. *paratuberculosis* Challenge

Vaccinated B6 and BALB/c mice were rested for weeks after the last immunization before challenge.

Luminescent MAP S-23 or ATCC 19698 (1) was grown in Middlebrook 7H9 medium supplemented with OADC, mycobactin J (Allied Laboratories Inc, Synbiotics Europe, 2 μg/ml) and hygromycin (100 μg/ml), to an O.D. between 0.6 and 0.8.

Bacteria were centrifuged for 30 minutes at 2000 rpm, suspended in PBS to a concentration of $8.5 \times 10^6$ RLU/ml (measured in LB 9507 Luminometer) and mice were infected intravenously in a lateral tail vein with 0.2 ml of bacteria.

The ratio CFU/RLU for exponentially growing axenic MAP cultures was determined to be 1.2 using Lumat LB 9507 luminometer (Berthold Technologies) and the ratio CFU/mRLU 2.5 using a Turner Design 20/20 luminometer.

The number of bioluminescent bacteria in spleen homogenates was determined using a bioluminescence assay with a Lumat LB 9507 luminometer (Berthold Technologies) or a Turner Design 20/20 luminometer and 1% n-decyl-aldehyde (Sigma) in ethanol as substrate.

In this assay, only live bacteria are enumerated, because emission of light is dependent on the presence of reduced flavin mononucleotide ($FMNH_2$), co-factor which is only found in living cells.

For statistical analysis (one way ANOVA, Tukey's Multiple Comparison Test), results obtained in Relative Light Units (RLU) were converted to log 10 values.

Counting the number of Colony Forming Units (CFU).

The number of CFU of MAP in spleen homogenates was determined by plating serial dilutions in PBS on Middlebrook 7H11-OADC agar supplemented with mycobactin J and with/without hygromycin.

*M. bovis* Infection.

Mice were inoculated intravenously with 0.05 mg of *M. bovis* AN5 from a stock kept frozen at −80° C.

Cattle

A first group of five 2-3 week old cattle were kept in isolation for 47 weeks. Two calves originating from a paratuberculosis free herd were kept as controls. A third calf from the same origin was vaccinated subcutaneously at 2 months of age with $2 \times 10^8$ CFU of irradiated *M. Paratuberculosis* (MAP) reference strain ATCC 19698 in an oil adjuvant (Montanide ISA 775; SEPPIC). Finally, two calves, born from cows suffering from clinical paratuberculosis (as confirmed by Pourquier serology and by positive fecal and post-mortem organ Map cultures) were kept from the age of 1 week and used as presumably infected animals.

A second group of 41 calves originating from a culture confirmed paratuberculosis herd, all aged 2 to 4 months, was blood sampled to assess antigen performance and sensitivity in the field conditions, and tested alongside Pourquier serology and fecal culture.

A third group of 39 calves originating from a culture confirmed natural bovine tuberculosis outbreak was used to assess antigen specificity in terms of *M. bovis*/MAP infection differentiation.

Proliferation Assays in Infected Cattle.

Blood was collected on heparin by venipuncture and proliferative responses were analyzed using a whole blood assay in 10% autologous plasma.

Briefly, heparinized blood was diluted 1:10 in RMPI-1640 medium supplemented with $5 \times 10^5$ M 2-mercapto-ethanol.

200 μl of cells were mixed with 25 μl of antigen in 96-well round-bottom microwell plates, and cultures were incubated in a humidified $CO_2$ incubator for 7 days.

Avian and bovine purified protein derivative (PPD) were tested at a 20 μg/ml, and recombinant MAP proteins at a 5 μg/ml final concentration.

Recombinant Ag85A (MAP0216) and Ag85B (MAP1609C) from MAP were included as controls, as described previously (4).

After 6 days, cells were pulsed overnight with tritiated thymidine (0.4 μCi/well) and collected on a Titertek Cell Harvester.

Radioactivity recovered on the filters was counted in a Betaplate Liquid Scintillation Counter and results expressed as mean cpm±SD, or mean stimulation index (SI)±SD, of triplicate cultures.

Bovine Ex Vivo 20h-IFN-γ Production and Interferon-Gamma Assay.

Tests were performed as previously described (3), with the following modifications: heparinized blood was collected from the jugular vein and 200 μl aliquots were incubated in duplicate without antigen, with avian and bovine PPD at a 20 μg/ml final concentration, with ESAT-6 and CFP-10 synthetic oligopeptide pools at a 5 μg/ml final concentration each peptide (7), or with purified recombinant MAP proteins at a 5 μg/ml final concentration. Cells were incubated for 20 hours at 37° C. in a humidified 5% $CO_2$ incubator. After centrifugation, plasma supernatants were collected and stored at −20° C. until testing.

Bovine IFN-γ was determined using a bovine IFN-γ ELISA (BioSource Europe S.A., Nivelles, Belgium).

Cultured In Vitro 6 Day IFN-γ Production in Infected Cattle.

Heparinized blood was diluted 1:8 in RMPI-1640 medium supplemented with 5×10-5 M 2-mercapto-ethanol. 200 μl of cells were mixed with 25 μl of antigen (concentrations as above) in 96-well round-bottom microwell plates, and cultures were incubated in a humidified CO2 incubator for 6 days. Supernatants were processed as above in the IFN-γ ELISA.

2.—Results:

Protein Identification:

In the present invention, a postgenomic approach was implemented in order to identify new antigens that could be used for the serological diagnosis of Johne's disease.

Two different and complementary approaches were used for antigen identification, the first approach being based on sequence comparison with *M. bovis* and *M. avium* subsp. *avium* genome, and the second approach being based on an immunoproteomic approach, using sera from MAP infected cattle.

In the first approach, a database of all proteins found in MAP CF (sub-proteome) has been established (125 proteins, not presented), considering that MAP CF (culture filtrate) was representative of the MAP secretome.

In the context of identifying non cross-reactive antigens, the most important characteristic of the proteins identified is their specificity. All proteins of the database have thus been compared to *M. bovis* complete and *M. avium* subsp. *avium* unfinished genome using BLAST at the TIGR server.

From this database, only 15 proteins out of the 125 CF proteins identified were found to be absent from the *M. bovis* genome. These proteins could be particularly useful to discriminate infections by MAP and *M. bovis*, in regions where they co-exist, and could thus represent valuable antigens for the diagnosis of paratuberculosis.

Table 1 presents the corresponding database of 15 proteins identified according to the first approach.

TABLE 1

| SEQUENCE REFERENCE | NAME | REFERENCE | SIMILARITY/PUTATIVE FUNCTION |
|---|---|---|---|
| SEQ. ID. NO. 1 | MAP0586c | CF027; CF274 | Possible transglycosylase SLT domain, *Prochlorococcus marinus* strain MIT 9313 |
| SEQ. ID. NO. 2 | MAP2677c | CF040; CF233 | Hypothetical protein SCO4486, *Streptomyces coelicolor* |
| SEQ. ID. NO. 3. | MAP4308c | CF281; CF282; CF283; CF028; Mptb0074; Mptb0097; Mptb0137; Mptb0141; Mptb0151 | Fructose-bisphosphate aldolase class I, *Synechocystis* sp. strain PCC 6803 |
| SEQ. ID. NO. 4 | MAP1693c | CF041; CF264; CF106, CF126, Mptb0136 | Peptidyl-prolyl cis-trans isomerase, *Streptomyces coelicolor* |
| SEQ. ID. NO. 5 | MAP3199 | CF036 | Alternative splicing variant of microtubule-associated protein tau, *Bos taurus* |
| SEQ. ID. NO. 7 | MAP3547c | Mptb0136; CF341 | Hypothetical protein, uncultured bacterium 581 |
| SEQ. ID. NO. 8 | MAP0139c | CF206 | Putative PadR-like family transcriptional regulator |
| SEQ. ID. NO. 10 | MAP0740c | CF458 | none |
| SEQ. ID. NO. 11 | MAP0796c | CF222 | none |
| SEQ. ID. NO. 14 | MAP1562c | CF201 | none |
| SEQ. ID. NO. 15 | MAP2411 | CF205 | Pyridoxamine 5'-phosphate oxidase |
| SEQ. ID. NO. 16 | MAP2746 | CF215 | none |
| SEQ. ID. NO. 20 | MAP3486 | CF352 | Possible L-lactate 2-monooxygenase ? |
| SEQ. ID. NO. 21 | MAP3680c | CF319 | Formate dehydrogenase |
| SEQ. ID. NO. 25 | MAP4096 | CF038 | Putative NADH dehydrogenase/NAD(P)H nitroreductase AF1167, *Archaeoglubus fulgidus* |

A genomic comparison with publicly accessible, complete or unfinished, mycobacterial genomes indicated that two of these identified proteins were completely specific of MAP. These two proteins specific of MAP are: MAP2746 (SEQ.ID.NO.16) and MAP3680c (SEQ.ID.NO.21).

In a further step, according to the second, immunoproteomic approach, proteins from CE and CF were resolved using both uni- and bidimensional electrophoresis so as to overcome the drawbacks related to the loss of information sometimes associated with 2DE due, for example, to solubility problems or the pI range used. These proteins were assessed for antigenicity by Western blot using sera of MAP infected cattle.

Results are presented on FIG. 1.

Three different positive reference sera were used in this approach and permitted detection of more than 40 proteins.

For this reason, only proteins reacting with at least two of the three positive reference sera were considered antigenic.

Additionally, antigenic proteins reacting with sera from *M. bovis* infected cattle were eliminated.

Finally, 14 antigenic proteins were selected using this procedure.

Table 2 presents the database with these 14 proteins identified following the second approach.

TABLE 2

| SEQUENCE REFERENCE | NAME | REFERENCE | SIMILARITY/PUTATIVE FUNCTION |
|---|---|---|---|
| SEQ. ID. NO. 1 | MAP0586c | CF027; CF274 | Possible transglycosylase SLT domain, *Prochlorococcus marinus* strain MIT 9313 |
| SEQ. ID. NO. 3. | MAP4308c | CF281; CF282; CF283; CF028; Mptb0074; Mptb0097; Mptb0137; Mptb0141; Mptb0151 | Fructose-bisphosphate aldolase class I, *Synechocystis* sp. strain PCC 6803 |
| SEQ. ID. NO. 4 | MAP1693c | CF041; CF264; CF106, CF126, Mptb0136 | Peptidyl-prolyl cis-trans isomerase, *Streptomyces coelicolor* |
| SEQ. ID. NO. 6 | MAP0907 | CF136; Mptb0099; Mptb0143; CF280 | Probable oxidoreductase, *Bordetella pertussis* |
| SEQ. ID. NO. 7 | MAP3547c | Mptb0136; CF341 | Hypothetical protein, uncultured bacterium 581 |
| SEQ. ID. NO. 9 | MAP0494 | Mptb0142; Mptb0156 | Putative oxidoreductase, *Streptomyces coelicolor* |
| SEQ. ID. NO. 12 | MAP1168c | Mptb0121 | Putative oxidoreductase SAV780, *Streptomyces avermitilis* |
| SEQ. ID. NO. 13 | MAP1438c | Mptb0048 | Bll4284 protein, *Bradyrhizobium japonicum* |
| SEQ. ID. NO. 17 | MAP2770 | CF107 | 27 kDa lipoprotein antigen Precursor, *Mycobacterium intracellulare* |
| SEQ. ID. NO. 18 | MAP2963c | Mptb0076 | Hypothetical protein, *Streptomyces avermitilis* |
| SEQ. ID. NO. 19 | MAP3385 | Mptb0094 | Conserved hypothetical protein, *Mycobacterium bovis* |
| SEQ. ID. NO. 22 | MAP3731c | Mptb0012 | ATP binding protein of ABC transporter, *Bifidobacterium longum* |
| SEQ. ID. NO. 23 | MAP3804 | CF118; Mptb0035; CF032 | Possible beta-1,3-glucanase, *Mycobacterium bovis* |
| SEQ. ID. NO. 24 | MAP4056c | CF128 | Possible conserved secreted protein, *Mycobacterium bovis* |

By combination of the data obtained in these complementary approaches, a database of 25 potential antigens candidates based on their specificity and/or antigenicity was finally established.

Tables 3 and 20 present the corresponding database of candidate antigens for paratuberculosis diagnosis and/or vaccination.

TABLE 3

| SEQUENCE REFERENCE | NAME | REFERENCE | SIMILARITY/PUTATIVE FUNCTION |
|---|---|---|---|
| SEQ. ID. NO. 1 | MAP0586c | CF027; CF274 | Possible transglycosylase SLT domain, *Prochlorococcus marinus* strain MIT 9313 |
| SEQ. ID. NO. 2 | MAP2677c | CF040; CF233 | Hypothetical protein SCO4486, *Streptomyces coelicolor* |
| SEQ. ID. NO. 3. | MAP4308c | CF281; CF282; CF283; CF028; Mptb0074; Mptb0097; Mptb0137; Mptb0141; Mptb0151 | Fructose-bisphosphate aldolase class I, *Synechocystis* sp. strain PCC 6803 |
| SEQ. ID. NO. 4 | MAP1693c | CF041; CF264; CF106, CF126, Mptb0136 | Peptidyl-prolyl cis-trans isomerase, *Streptomyces coelicolor* |
| SEQ. ID. NO. 5 | MAP3199 | CF036 | Alternative splicing variant of microtubule-associated protein tau, *Bos taurus* |
| SEQ. ID. NO. 6 | MAP0907 | CF136; Mptb0099; Mptb0143; CF280 | Probable oxidoreductase, *Bordetella pertussis* |
| SEQ. ID. NO. 7 | MAP3547c | Mptb0136; CF341 | Hypothetical protein, uncultured bacterium 581 |
| SEQ. ID. NO. 8 | MAP0139c | CF206 | Putative PadR-like family transcriptional regulator |

TABLE 3-continued

| SEQUENCE REFERENCE | NAME | REFERENCE | SIMILARITY/PUTATIVE FUNCTION |
|---|---|---|---|
| SEQ. ID. NO. 9 | MAP0494 | Mptb0142; Mptb0156 | Putative oxidoreductase, *Streptomyces coelicolor* |
| SEQ. ID. NO. 10 | MAP0740c | CF458 | none |
| SEQ. ID. NO. 11 | MAP0796c | CF222 | none |
| SEQ. ID. NO. 12 | MAP1168c | Mptb0121 | Putative oxidoreductase SAV780, *Streptomyces avermitilis* |
| SEQ. ID. NO. 13 | MAP1438c | Mptb0048 | Bll4284 protein, *Bradyrhizobium japonicum* |
| SEQ. ID. NO. 14 | MAP1562c | CF201 | none |
| SEQ. ID. NO. 15 | MAP2411 | CF205 | Pyridoxamine 5'-phosphate oxidase |
| SEQ. ID. NO. 16 | MAP2746 | CF215 | none |
| SEQ. ID. NO. 17 | MAP2770 | CF107 | 27 kDa lipoprotein antigen Precursor, *Mycobacterium intracellulare* |
| SEQ. ID. NO. 18 | MAP2963c | Mptb0076 | Hypothetical protein, *Streptomyces avermitilis* |
| SEQ. ID. NO. 19 | MAP3385 | Mptb0094 | Conserved hypothetical protein, *Mycobacterium bovis* |
| SEQ. ID. NO. 20 | MAP3486 | CF352 | Possible L-lactate 2-monooxygenase ? |
| SEQ. ID. NO. 21 | MAP3680c | CF319 | Formate dehydrogenase |
| SEQ. ID. NO. 22 | MAP3731c | Mptb0012 | ATP binding protein of ABC transporter, *Bifidobacterium longum* |
| SEQ. ID. NO. 23 | MAP3804 | CF118; Mptb0035; CF032 | Possible beta-1,3-glucanase, *Mycobacterium bovis* |
| SEQ. ID. NO. 24 | MAP4056c | CF128 | Possible conserved secreted protein, *Mycobacterium bovis* |
| SEQ. ID. NO. 25 | MAP4096 | CF038 | Putative NADH dehydrogenase/NAD(P)H nitroreductase AF1167, *Archaeoglubus fulgidus* |

From this database, three candidate proteins SEQ.ID.NO.4 (also referenced as MAP1693c), SEQ.ID.NO.3 (MAP4308c) and SEQ.ID.NO.1 (MAP0586c), were then selected because they were specific and antigenic. Two others candidate proteins, SEQ.ID.NO.5 (MAP3199) and SEQ.ID.NO.2 (MAP2677c), were chosen because of their specificity.

This means that these five candidate proteins could advantageously be used for Paratuberculosis serological diagnostic, and thereby Johne's disease control, either alone and/or in partial combinations (i.e. in combination with at least one of the other four proteins) and/or in total combination ("total" meaning with the other four proteins).

Other candidate proteins from the database could also advantageously be used for Paratuberculosis diagnosis and/or vaccination, such as for example SEQ.ID.NO.7 (MAP3547c), SEQ.ID.NO.9 (MAP0494), and/or SEQ.ID.NO.6 (MAP0907).

This means that these three candidate proteins could advantageously be used for *Paratuberculosis* diagnosis and/or vaccination, either alone and/or combined with each other, and/or in combination with at least one of the remaining 24 identified proteins, and particularly advantageously with at least one protein selected from the group consisting of SEQ.ID.NO.4 (MAP1693c), SEQ.ID.NO.3 (MAP4308c), SEQ.ID.NO.1 (MAP0586c), SEQ.ID.NO.5 (MAP3199) and SEQ.ID.NO.2 (MAP2677c).

These three candidate proteins could also advantageously be used for *Paratuberculosis* diagnosis and/or vaccination in combination with at least one, at least two, at least three, at least four, or with all the five candidate proteins mentioned hereabove (i.e. selected from the group consisting of SEQ.ID.NO.1 to SEQ.ID.NO.5).

Candidate proteins from the database presented in Tables 3 and 20 have been successfully cloned in *E. coli*, expressed, and efficiently purified by use of an IMAC strategy as illustrated on FIGS. 2 and 3.

Genes encoding candidate antigenic proteins were amplified by PCR from MAP genomic DNA using primers derived from the MAP genomic sequence as specified in Tables 4 and 5.

TABLE 4

| Antigen no | Restriction Enzymes | Primer sequences forward (Fw) and reverse (Rv) | |
|---|---|---|---|
| MAP4308c | BglII (Fw)/ | SEQ. ID. NO. 43: | GGAAGATCTTGTGCGGTGTGCCCGTGAGGG (Fw) |
| | EcoRI (Rv) | SEQ. ID. NO. 44: | ATAGAATTCGCCGGCGACCGAGGCGTCGTA (Rv) |
| MAP2677c | BglII (Fw)/ | SEQ. ID. NO. 45: | GGAAGATCTGCTTGGGCGACACCACA (Fw) |
| | EcoRI (Rv) | SEQ. ID. No. 46: | TATAGAATTCTACTTTGAACTTGGCCCGC (Rv) |
| MAP1693c | BglII (Fw)/ | SEQ. ID. NO. 47: | TATATAGATCTTGACGGCTGTGAACTCCGT (Fw) |
| | EcoRI (Rv) | FL | |
| | | SEQ. ID. NO. 48: | TATAGAATTCGGTCGTGGCGCCGAGGAT (Rv) |
| | | SEQ. ID. NO. 49: | TATATAGATCTTGGCCGACTCCTGCCCGACC (Fw) |
| | | mature | |
| MAP0586c | BglII (Fw)/ | SEQ. ID. NO. 50: | GGAAGATCTTGGTGAGCAATCGGCGCACC (Fw) |
| | EcoRI (Rv) | SEQ. ID. NO. 51: | TATAGAATTCCTGCGGGTGCGCCGCCACGTAGTCGG (Rv) |

TABLE 4-continued

| Antigen no | Restriction Enzymes | Primer sequences forward (Fw) and reverse (Rv) |
|---|---|---|
| MAP3199 | BglII (Fw)/ | SEQ. ID. NO. 52: GGAAGATCTTGGTGCCCGCATCACCCGTTC (Fw) |
|  | EcoRI (Rv) | SEQ. ID. NO. 53: TATAGAATTCGATTCGCCACGACAGTTGGG (Rv) |

TABLE 5

| Antigen no | Restriction Enzymes | Primer sequences forward (Fw) and reverse (Rv) |
|---|---|---|
| MAP4308c | BamHI (Fw)/ | SEQ. ID. NO. 26: TATAGGATCCTGCGGTGTGCCCGTGAGG (Fw) |
|  | HindIII (Rv) | SEQ. ID. NO. 27: TATAAAGCTTCAGCCGGCGACCGAGGCGTCGTA (Rv) |
| MAP2677c | BglII (Fw)/ | SEQ. ID. NO. 28: GGAAGATCTTGCTTGGGCGACACCACA (Fw) |
|  | HindIII (Rv) | SEQ. ID. NO. 29: TATAAAGCTTTTATACTTTGAACTTGGCCC (Rv) |
| MAP1693c | BglIII (Fw)/ | SEQ. ID. NO. 30: TATATAGATCTGTGACGGCTGTGAACTCCGTCCG (Fw, FL) |
|  | HindIII (Rv) | SEQ. ID. NO. 31: TATATAGATCTGCCGACTCCTGCCCGACC (Fw, mature) |
|  |  | SEQ. ID. NO. 32: TATAAAGCTTCTAGGTCGTGGCGCCGAGGAT (Rv) |
| MAP3199 | BglII (Fw)/ | SEQ. ID. NO. 35: GGAAGATCTGTGCCCGCATCACCC (Fw) |
|  | HindIII (Rv) | SEQ. ID. NO. 36: TATAAAGCTTCAGATTCGCCACGACAGTTGG (Rv) |
| MAP0907 | BamHI (Fw)/ | SEQ. ID. NO. 37: ATATGGATCCGTGAGCAAGGTTCCGACGATCGAA (Fw) |
|  | HindIII (Rv) | SEQ. ID. NO. 38: ATATAAGCTTTCAGCGCGGTATGTAGTCGAAGGTGTCC (Rv) |
| MAP1168c | BamHI (Fw)/ | SEQ. ID. NO. 39: ATATGGATCCGTGTCCGCCGGAATCATCCTCATGG (FW) |
|  | HindIII (Rv) | SEQ. ID. NO. 40: ATATAAGCTTTCACAGCGCGGCGGTGAGCCGCCAC (RV) |
| MAP3547c | BglII (Fw)/ | SEQ. ID. NO. 41: ATATAGATCTGTGACGCACGAATCGACCGCCGCATGGCGG (Fw) |
|  | HindIII (Rv) | SEQ. ID. NO. 42: ATATAAGCTTTCAGCGCACCGCCGTCGGGGCGTCGGC (Rv) |

High purity has been obtained by eluting the proteins with a linear gradient of competing agent rather than a stepwise elution. It was obviously critical in the present context to obtain high purity antigens.

Candidate proteins were tested for their applications in diagnosis and/or in vaccination. Non limiting examples of such applications are presented hereafter.

EXAMPLE 1

Serological ELISA Diagnosis—Antigenicity Results

In FIG. 4, the antigenicity of candidate antigens is shown. Antigenicity of these purified candidate antigens has been measured in ELISA. It appears clearly that MAP1693c, MAP4308c and MAP2677c produce a high signal with some sera of MAP infected cattle. However, none of this three antigens could be used alone to detect all the tested sera. Combinations of these three antigens increase the response and will so be used to investigate the sensitivity and specificity of the present assay with a larger panel of sera (21 MAP+, 48 control).

EXAMPLE 2

Serological ELISA Diagnosis—ROC Analysis

ROC analysis of ELISA tests (see FIGS. 5 and 6) showed the following interesting results concerning part of the proteins from the database as summarized in Table 6.

TABLE 6

| Protein | Sensitivity | Specificity | Antigenicity |
|---|---|---|---|
| MAP1693c + MAP4308c + MAP2677c (see page 38) | 94.7% | 97.9% | ++ |
| MAP0907c | 76.5% | 98% | ++ |
| MAP3547c | 94.1% | 95.7% | ++ |
| MAP1693c + MAP4308c + MAP2677c + MAP907c + MAP3547c | 76.4% | 97.9 | + |

At least three candidate proteins have been included in a very efficient ELISA-based diagnosis test. These proteins correspond to MAP1693c, MAP4308c and MAP2677c.

At least two other candidate proteins are very efficient in single antigne-based assays (i.e. when used alone). These are MAP0907c (SEQ.ID.NO.6) and MAP3547c (SEQ.ID.NO.7).

EXAMPLE 3

Comparison with Pourquier Test

The panel of positive and negative sera used to challenge the ELISA test using MAP1693c, MAP4308c and MAP2677c has also been tested with the commercially available Pourquier test. Results of this test are presented in table 7.

Positive reference sera used in the ELISA tests were from 21 naturally infected cows shedding MAP at the time of sampling, as shown by faecal culture.

As shown in Table 7, among these positive reference sera, five sera were tested negative in the commercial kit of Pourquier (France).

Control sera were from 48 cattle from two *M. bovis*-infected herds with no history of Paratuberculosis.

As shown in Table 7, six of these control sera were positive in the MAP Pourquier test. The Pourquier test obtained thus a sensitivity of 76.2% for a specificity of 87.5%.

These results confirm that the ELISA tests according to the present invention enhance the efficiency of the diagnosis comparatively to the commercial kit of Pourquier (France).

T cell epitope mapping, using synthetic overlapping peptides, demonstrated that sequence 187-201 (SEQ.ID.NO.54) LVPIIEPEVTISIAD encompassed an immunodominant H-$2^b$ restricted Th1 epitope (FIG. 1A) and sequence 241-255 (SEQ.ID.NO.55) PLIEHPKVMRVVALS and 247-261 (SEQ.ID.NO.56) KVMRVVALSGGYSRE an immunodominant H-$2^d$ restricted epitope (FIG. 7).

TABLE 7

| MAP + serum number | % of positive control in Pourquier test | | faecal culture | Control serum number | % of positive control in Pourquier test | serum number | % of positive control in Pourquier test |
|---|---|---|---|---|---|---|---|
| | test1 | test2 | | | | | |
| | | | + | 1677 6519 | 11% | 16192916 | 6% |
| 810[b] | 179% | 140% | + | 7058 5887 | 9% | 16905321 | 7% |
| 845[b] | 264% | 174% | + | 0153 | 23% | 16768339 | 46% |
| 863 | 177% | 129% | + | 0154 | 6% | 16856202 | 69% |
| 885[b] | 89% | 74% | + | 1676 6208 | 18% | 16768342 | 22% |
| 760[b] | 202% | 205% | + | 1627 6085 | 134% | 16856237 | 22% |
| 906[b] | 89% | 96% | + | 1679 4405 | 8% | 16661714 | 9% |
| 930 | 89% | 55% | + | 1688 4036 | 10% | 16856228 | 40% |
| 758 | 124% | 104% | + | 1692 4315 | 12% | 16768338 | 11% |
| 801 | 98% | 85% | + | 1689 0912 | 8% | 16042428 | 3% |
| 778 | 301% | 219% | + | 1642 5174 | 161% | 16984208 | 4% |
| 4415 | 15% | 3% | + | 1635 2022 | 11% | DE 1302415614 | 8% |
| 899 | 1% | 1% | + | 0155 | 18% | DE 1302415618 | 13% |
| 805 | 7% | 5% | + | 1634 9664 | 3% | DE 1302415607 | 169% |
| 887 | 6% | 4% | + | 1577 2493 | 3% | DE 1302415605 | 68% |
| 880 | 2% | 4% | + | 1616 0503 | 6% | DE 1302415630 | 93% |
| DK[ab] | 250% | | + | 1672 0600 | 12% | DE 1302415617 | 3% |
| 45[ab] | 210% | | + | 2006-04549-1 | 15% | DE 1302214318 | 20% |
| 7828[a] | 207% | | + | 2006-04549-2 | 8% | 16905344 | 4% |
| 3531[a] | 203% | | + | 2006-04549-3 | 12% | 16984210 | 2% |
| | | | | 2006-04549-4 | 9% | 16905347 | 2% |
| | | | | 2006-04549-5 | 7% | 16984215 | 2% |
| | | | | 16768320 | 30% | 17072808 | 4% |
| | | | | 16768322 | 2% | DE 1302578332 | 5% |

EXAMPLE 4

Vaccines

It is known that the initial stage of MAP infection is controlled by a Th1 type immune response (IL-2, IFN-γ) and that progression towards disease is accompanied by a loss of this Th1 response and the apparition of a Th2 type response as well as by the apparition of antibodies.

It is also known that IFN-γ is the pivotal cytokine involved in protection against mycobacterial diseases in general.

DNA vaccines encoding either MAP4308c (SEQ.ID.NO.3), or MAP0586c (SEQ.ID.NO.1), or MAP2977c (SEQ.ID.NO.2), or MAP3199 (SEQ.ID.NO.5) or MAP1693c (SEQ.ID.NO.4) were tested for their capacity to induce this Th-1 type immune response.

Protection could be partially obtained in a mouse model using DNA vaccines. The results are particularly interesting using MAP4308c and MAP0586c as illustrated hereafter.
Vaccination with MAP4308c (SEQ.ID.NO.3):

Vaccination with DNA encoding MAP4308c induced a strong antigen-specific cellular (IL-2 and IFN-γ) and humoral response in BALB/c and C57BL/6 mice (FIG. 14).

Vaccination with SEQ.ID.NO.3 (MAP4308c) DNA induced strong total IgG, IgG1, IgG2a and IgG2b antibodies in both mouse strains. Levels were higher in serum from protein boosted mice, and levels were higher in BALB/c (FIG. 14) than in B6 mice (FIG. 14). IgG2a and IgG2b antibodies were characteristics of Th-1 type immune response

TABLE 9

Table 9: Bacterial replication in spleen from C57BL/6 mice vaccinated with DNA control, DNA-MAP4308c and DNA-MAP4308c boosted with recombinant MAP4308c protein in IFA adjuvant and challenged of bioluminescent *M. avium* subsp. *paratuberculosis* S23 and analysed 8 weeks postinfection.

| | C57B/6 | |
|---|---|---|
| | $Log_{10}$ mRLU/ spleen | $Log_{10}$ CFU/ spleen |
| Empty DNA | 4.62 ± 0.17 (4) | 6.13 ± 0.14 (4)a |
| DNA-MAP4308c | 4.08 ± 0.36 (4)* | 5.57 ± 0.21 (4)** |
| DNA-MAP4308c - protein | 4.27 ± 0.16 (5)$^{ns}$ | 5.77 ± 0.26 (5)$^{ns}$ |

Table 9: Bacterial Replication in Spleen from C57BL/6 Mice Vaccinated with DNA Control, DNA-MAP4308c and DNA- MAP4308c Boosted with Recombinant MAP4308c Protein in IFA Adjuvant and Challenged of Bioluminescent *M. avium* subsp. *paratuberculosis* S23 and Analysed 8 Weeks Postinfection.

Vaccination with SEQ.ID.NO.1 (MAP0586c)

Vaccination with DNA encoding MAP0586c induced a strong, antigen-specific IL-2 and IFN-γ response in BALB/c and C57BL/6 mice as illustrated in FIG. 15.

Epitope mapping showed that peptides 291-310 LLPIGY-DASSPIPAADYVAA (SEQ.ID.NO.57) and 301-320 IGY-DASSPIPAADYVAAHPQ (SEQ.ID.NO.58) were very strong $H-2^b$ restricted IL-2 and IFN-γ epitopes (FIG. 8A) and peptides 121-140 ELIDVYDRNVDARRQLTALT (SEQ.ID.NO.59) and 171-190 SGVGWNYLAAINFIETRFGS (SEQ.ID.NO.60) very strong $H-2^d$ restricted epitopes (FIG. 8B).

Vaccination with plasmid DNA encoding MAP 0586c induced only weak total IgG, IgG1, IgG2a and IgG2b antibody levels in both mouse strains (FIG. 15). Such vaccinal response could be particularly interesting since it will not impair a subsequent serological detection of Jonhe's disease. Protein boosting induced significant antibody levels.

DNA encoding MAP0586c protected BALB/c mice partially against a challenge with luminescent MAP ATCC16968* at 8 weeks post infection (table 11).

TABLE 11

Table 11: Bacterial replication in spleen from BALB/c mice vaccinated with DNA control, DNA-MAP0586c and DNA-MAP0586c boosted with recombinant MAP0586c protein in IFA adjuvant and challenged with bioluminescent *M. avium* subsp. *paratuberculosis* ATCC 19698 and analysed 8 weeks postinfection[a]

| | BALB/c | |
|---|---|---|
| | $Log_{10}$ RLU/ spleen | $Log_{10}$ CFU/ spleen |
| Empty DNA | 5.30 ± 0.19 (5) | 5.94 ± 0.04 (5) |
| DNA-MAP0586c | 4.80 ± 0.27 (4)* | 5.56 ± 0.23 (4)* |
| DNA-MAP0586c - protein | 4.72 ± 0.19 (5)** | 5.38 ± 0.21 (5)*** |

Table 11: Bacterial Replication in Spleen from BALB/c Mice Vaccinated with DNA Control, DNA-MAP0586c and DNA-MAP0586c Boosted with Recombinant MAP0586c Protein in IFA Adjuvant and Challenged with Bioluminescent *M. avium* subsp. *paratuberculosis* ATCC 19698 and Analysed 8 Weeks postinfection[a]

Vaccination with SEQ.ID.NO.5 (MAP3199) and SEQ.ID.NO.2 (MAP2677c):

Vaccination with DNA encoding MAP3199 and MAP2677c induced a significant antigen-specific production of IL-2 and IFN-γ in C57BL/6 (Table 12).

TABLE 12

Table 12: IFN-γ and IL-2 activities as measured in 24- and 72-h spleen cell culture supernatants, from C57BL/6 mice vaccinated with V1J.ns-tPA, V1J.ns-tPA-his-MAP3199 or V1J.ns-tPA-his-MAP2677c. Cells were restimulated MAP3199 or MAP2677c (5 μg/ml)

| | C57BL/6 | |
|---|---|---|
| | IL-2 (CPM) | IFN-γ (pg/ml) |
| 4 × V1J-ns-tPA (n = 4) | 1,977 ± 427 | 116 ± 61 |
| 4 × V1J-ns-tPA-his-MAP2677c (n = 4) | 12,928 ± 9,539 | 17,298 ± 3,774 |

TABLE 12-continued

Table 12: IFN-γ and IL-2 activities as measured in 24- and 72-h spleen cell culture supernatants, from C57BL/6 mice vaccinated with V1J.ns-tPA, V1J.ns-tPA-his-MAP3199 or V1J.ns-tPA-his-MAP2677c. Cells were restimulated MAP3199 or MAP2677c (5 μg/ml)

| | C57BL/6 | |
|---|---|---|
| | IL-2 (CPM) | IFN-γ (pg/ml) |
| 4 × V1J-ns-tPA (n = 4) | 1,977 ± 427.5 | 298 ± 297 |
| 4 × V1J-ris-tPA-his-MAP3199 (n = 4) | 25,042 ± 7,099 | 6,801 ± 2,943 |

Vaccination with SEQ.ID.NO.4 (MAP1693):

Significant antigen-specific production of IFN-γ immune responses were obtained after vaccination of BALB/c and C57BL/6 mice with either full-length or the mature construct, both using the classical DNA vaccination regimen or the DNA prime-protein boost regimen (Table 13).

TABLE 13

Table 13: IFN-γ and IL-2 activities as measured in 72-h spleen cell culture supernatants, from C57BL/6 and BALB/c mice vaccinated with V1J.ns-tPA, V1J-ns-tPA-his-MAP1693c mature, V1J-ns-tPA-his-MAP1693c-FL and V1J-ns-tPA-his- MAP1693c-FL + MAP1693c. Cells were restimulated MAP1693c mature or full lenght (5 μg/ml)

| | Restimulated with MAP1693c mature | Restimulated with MAP1693c FL |
|---|---|---|
| C57BL/6 IFNγ (pg/ml) | | |
| 4 × V1J-ns-tPA (n = 4) | 69 ± 18 | 49 ± 5 |
| 4 × V1J-ns-tPA-his-MAP1693c mature (n = 3) | 20,273 ± 8,144 | 3,940 ± 3,814 |
| 4 × V1J-ns-tPA-his-MAP1693c-FL (n = 3) | 7,635 ± 4,066 | 5,562 ± 4,241 |
| 3 × V1J-ns-tPA-his-MAP1693c-FL + MAP1693c (n = 3) | 7,138 ± 1,859 | 7,161 ± 1,891 |
| BALB/c IFNγ (pg/ml) | | |
| 4 × V1J-ns-tPA (n = 4) | 209 ± 168 | 76 ± 30 |
| 4 × V1J-ns-tPA-his-MAP1693c mature (n = 3) | 8,843 ± 4,041 | 8,194 ± 9,569 |
| 4 × V1J-ns-tPA-his-MAP1693c-FL (n = 3) | 6,984 ± 7,042 | 1,520 ± 1,488 |
| 3 × V1J-ns-tPA-his-MAP1693c-FL + MAP1693c (n = 3) | 11,638 ± 7,339 | 1,621 ± 1,237 |

Infection with MAP S23 and *M. bovis:*

With the aim to confirm the specificity of the antigens, immune response against the different purified recombinant proteins was studied in spleen cell cultures from C57BL/6 mice infected with the intravenous route with either MAP-S23 or *M. bovis* (FIGS. 9 and 10).

As show in FIGS. 3 and 4, none of the proteins induce production of IFN-γ in B6 infected *M. bovis*, confirming the specificity of these antigens.

Responses against MAP0586c (SEQ.ID.NO.1), MAP3199 (SEQ.ID.NO.2) and MAP1693FL (SEQ.ID.NO.4) proteins induced strong IFN-gamma responses in MAP. MAP2977 (SEQ.ID.NO.2) induced a intermediary and MAP4308c (SEQ.ID.NO.3) a low IFN-γ responses.

These responses confirmed the immunogenicity of this five antigens in infection context in B6 mice.

EXAMPLE 5

Diagnosis Using Cellular Responses

At least three antigens have been shown to be efficient for cellular diagnosis of MAP. These three antigens are MAP2677c, MAP0586c and MAP4308c. This means that they could be exploited in an ex vivo IFN gamma-based diagnostic assay.

At least four antigens have been shown to have an interesting immunizing potential. These four antigens are MAP1693c, MAP2677c, MAP0586c and MAP4308c.

Antigen Specificity:

Four antigens, SEQ.ID.NO.1 (MAP0586C), SEQ.ID.NO.3 (MAP4308C), SEQ.ID.NO.2 (MAP2677C), and SEQ.ID.NO.5 (MAP3199) have been shown to be specific as follows.

Thirty-nine cattle from a culture-confirmed *M. bovis* outbreak were tested in ex vivo 20h-IFN. They were tested in the bovine TB IFN-gamma assay based on avian and bovine PPDs and results analysed using previously validated interpretation criteria (3). Two cattle were classified paratuberculosis reactors based on these criteria and the remaining yielded TB-specific, aspecific, non-interpretable (high background), or negative results.

All animals were simultaneously tested in the IFN-gamma assay using the *Mycobacterium tuberculosis* complex-specific ESAT-6 and CFP-10 synthetic oligopeptide pools. The *M. bovis* infected status was confirmed by culture in 26 of the 37 non-paratuberculosis reactor cattle, and ESAT-6/CFP-10 specific responses were measured in 8 of the remaining animals (Table 14).

TABLE 14 ex vivo 20 h-IFN in 39 cattle from a culture-confirmed *M. bovis* outbreak.

| | cult | PBS | esat6 | cfp 10 | Map 3199 | Map 1693c | Map 0586 | Map 4308 | Map 2677 | | esat6 | cfp10 | Map 3199 | Map 1693c | Map 0586 | Map 4308 | Map 2677 |
|---|---|---|---|---|---|---|---|---|---|---|---|---|---|---|---|---|---|
| 1 | − | 0.051 | 3.664 | 3.478 | | 0.058 | 0.079 | 0.062 | 0.074 | B | pos | pos | | neg | neg | neg | neg |
| 2 | + | 0.063 | 3.733 | 3.773 | | 0.075 | 0.100 | 0.064 | 0.114 | asp | pos | pos | | neg | neg | neg | neg |
| 3 | + | 0.123 | 3.760 | 3.656 | 0.128 | 0.138 | 0.159 | 0.139 | 0.144 | B | pos | pos | neg | neg | neg | neg | neg |
| 4 | − | *0.159* | 0.754 | 0.554 | 0.172 | 0.167 | 0.193 | 0.171 | 0.191 | NI | pos | pos | neg | neg | neg | neg | neg |
| 5 | + | 0.086 | 1.347 | 1.457 | | 0.106 | 0.110 | 0.103 | 0.086 | B | pos | pos | | neg | neg | neg | neg |
| 6 | − | 0.069 | 1.287 | 1.293 | | 0.066 | 0.073 | 0.073 | 0.076 | asp | pos | pos | | neg | neg | neg | neg |
| 7 | − | 0.067 | 0.556 | 0.467 | | 0.069 | 0.073 | 0.076 | 0.107 | B | pos | pos | | neg | neg | neg | neg |
| 8 | − | 0.057 | 0.893 | 0.885 | | 0.060 | 0.067 | 0.062 | 0.064 | asp | pos | pos | | neg | neg | neg | neg |
| 9 | − | 0.067 | 0.520 | 0.584 | | 0.063 | 0.089 | 0.080 | 0.083 | B | pos | pos | | neg | neg | neg | neg |
| 10 | + | 0.060 | 1.805 | 2.927 | | 0.064 | 0.093 | 0.078 | 0.088 | *asp* | pos | pos | | neg | neg | neg | neg |
| 11 | + | 0.049 | 0.840 | 1.145 | | 0.051 | 0.065 | 0.060 | 0.055 | B | pos | pos | | neg | neg | neg | neg |
| 12 | − | 0.111 | 3.604 | 3.503 | | 0.114 | 0.138 | 0.101 | 0.109 | asp | pos | pos | | neg | neg | neg | neg |
| 13 | + | 0.044 | 3.924 | 3.309 | 0.051 | 0.043 | 0.068 | 0.052 | 0.070 | asp | pos | pos | neg | neg | neg | neg | neg |
| 14 | + | 0.139 | 3.682 | 3.429 | 0.144 | 0.141 | 0.149 | 0.131 | 0.142 | B | pos | pos | neg | neg | neg | neg | neg |
| 15 | + | *0.299* | 1.351 | 1.298 | | 0.309 | 0.417 | 0.418 | 0.411 | NI | pos | pos | | neg | neg | neg | neg |
| 16 | + | 0.110 | 1.419 | 1.141 | | 0.120 | 0.127 | 0.122 | 0.132 | B | pos | pos | | neg | neg | neg | neg |
| 17 | − | 0.067 | 0.055 | 0.052 | 0.071 | 0.066 | 0.070 | 0.070 | 0.076 | | neg | neg | neg | neg | neg | neg | neg |
| 18 | + | 0.041 | 2.438 | 1.798 | 0.049 | 0.046 | 0.069 | 0.065 | 0.069 | B | pos | pos | neg | neg | neg | neg | neg |
| 19 | + | 0.049 | 2.871 | 3.426 | 0.075 | 0.053 | 0.099 | 0.076 | 0.092 | B | pos | pos | neg | neg | neg | neg | neg |
| 20 | + | 0.055 | 2.012 | 1.547 | 0.080 | 0.054 | 0.117 | 0.079 | 0.082 | B | pos | pos | neg | neg | neg | neg | neg |
| 21 | + | *0.232* | 1.143 | 1.540 | 0.108 | 0.138 | 0.171 | 0.156 | 0.160 | NI | pos | pos | neg | neg | neg | neg | neg |
| 22 | + | 0.048 | 1.048 | 1.174 | 0.054 | 0.053 | 0.093 | 0.060 | 0.065 | B | pos | pos | neg | neg | neg | neg | neg |
| 23 | + | *0.319* | 4 | 3.761 | 0.295 | 0.239 | 0.310 | 0.266 | 0.394 | NI | pos | pos | neg | neg | neg | neg | neg |
| 24 | + | 0.113 | 0.681 | 0.942 | 0.104 | 0.091 | 0.105 | 0.114 | 0.116 | B | pos | pos | neg | neg | neg | neg | neg |
| 25 | + | 0.060 | 4 | 4 | 0.071 | 0.066 | 0.107 | 0.080 | 0.095 | asp | pos | pos | neg | neg | neg | neg | neg |
| 26 | + | *0.258* | 3.040 | 2.223 | 0.398 | 0.277 | 0.536 | 0.428 | 0.437 | NI | pos | pos | neg | neg | pos | neg | neg |
| 27 | + | 0.048 | 2.129 | 2.390 | 0.059 | 0.054 | 0.062 | 0.046 | 0.056 | B | pos | pos | neg | neg | neg | neg | neg |
| 28 | + | 0.054 | 0.732 | 0.611 | 0.075 | 0.065 | 0.079 | 0.080 | 0.087 | B | pos | pos | neg | neg | neg | neg | neg |
| 29 | + | 0.053 | 0.260 | 0.251 | 0.066 | 0.058 | 0.080 | 0.064 | 0.074 | asp | pos | pos | neg | neg | neg | neg | neg |
| 30 | + | 0.102 | 0.118 | 0.115 | 0.130 | 0.172 | 0.179 | 0.096 | 0.141 | asp | neg | neg | neg | neg | neg | neg | neg |
| 31 | − | 0.067 | 0.057 | 0.053 | 0.857 | 0.062 | 1.543 | 0.960 | 1.291 | P | neg | neg | pos | neg | pos | pos | pos |
| 32 | − | 0.054 | 3.641 | 3.661 | 0.068 | 0.060 | 0.108 | 0.101 | 0.083 | B | pos | pos | neg | neg | neg | neg | neg |
| 33 | − | *0.217* | 0.380 | 1.522 | 0.225 | 0.064 | 0.085 | 0.079 | 0.319 | NI | neg | pos | neg | neg | neg | neg | neg |
| 34 | + | 0.075 | 0.328 | 0.450 | 0.301 | 0.098 | 0.089 | 0.085 | 0.096 | B | pos | pos | pos | neg | neg | neg | neg |
| 35 | + | 0.090 | 3.434 | 4 | 0.160 | 0.093 | 0.104 | 0.096 | 0.114 | B | pos | pos | neg | neg | neg | neg | neg |
| 36 | − | *0.525* | 3.232 | 2.313 | 0.452 | 0.533 | 0.510 | 0.573 | 0.507 | NI | pos | pos | neg | neg | neg | neg | neg |
| 37 | + | 0.049 | 2.245 | 1.901 | 0.039 | 0.042 | 0.042 | 0.045 | 0.044 | B | pos | pos | neg | neg | neg | neg | neg |
| 38 | − | 0.084 | 0.072 | 0.054 | 0.230 | 0.058 | 0.598 | 0.307 | 0.346 | P | neg | neg | pos | neg | pos | pos | pos |
| 39 | + | 0.073 | 3.155 | 2.698 | 0.195 | 0.092 | 0.185 | 0.637 | 0.181 | *asp* | pos | pos | pos | neg | neg | pos | neg |

Results shown are *M. bovis* isolation (+: successful; −: unsuccessful), OD readings in the IFNγ ELISA for the tested antigens and a PBS control, the standard PPD-based assay output (B = TB-positive; P = paratuberculosis positive; asp = non-specific mycobacterial sensitisation; NI = non interpretable; blank = negative), and all readings above the ELISA cutoff calculated following the supplier's specifications (neg = below; pos = above the cutoff).

1 The two paratuberculosis reactor cattle remained negative for M. bovis in culture and in the ESAT-6/CFP-10 based IFNγ assay.

The two paratuberculosis reactors detected the four antigens tested.

SEQ.ID.NO.2 (MAP2677C) remained undetected by any of the 37 non-paratuberculosis reactors. The remaining three antigens were however also detected by one animal out of the 37 non-paratuberculosis reactors, or two animals in the case of MAP3199, as shown in Table 14 and FIG. 11.

Assuming the two paratuberculosis reactors are truely MAP infected based on their recognition of the four antigens, and that none of the 27 remaining animals would be MAP infected, yields the single antigen specificities listed in the following Table (column "Calculated specificity").

Assuming all reactors would be false positives would yield the minimal specificities listed in the following Table 15 (column "Minimal Specificity"):

TABLE 15

| Antigen | Calculated Specificity | Minimal Specificity |
| --- | --- | --- |
| MAP0586C | 97.3% | 92.3% |
| MAP4308C | 97.3% | 92.3% |
| MAP2677C | 97.3% | 92.3% |
| MAP3199 | 92.6% | 85.2% |

Antigen Sensitivity:

A first group of five cattle kept in isolation from the age of 2 weeks, and either immunized with irradiated MAP (n=1), naturally infected at birth (n=2) or kept as controls (n=2), were tested twice at the age of 18 months, in the IFN-gamma assay.

All except the controls, showed consistent reactivity to avian PPD as shown in Table 16A.

TABLE 16A

Duplicate ex vivo 20 h-IFN readouts at 1 week interval, in 5 calves kept in isolation, including two presumed infected at birth (#3154 and 3702), one immunised with Map (#7), and 2 paratuberculosis free calves (#22 and 24). Antigens tested are a PBS negative control, avian and bovine PPDs, a staphylococcal enteroxin β (SEB) positive control, Johnin (PPDM), and the Map antigens.

| an # | PBS | PPDB | PPDA | SEB | PPDM | Map3199 | Map1693c | Map0586c | Map4308c | Map2677c |
| --- | --- | --- | --- | --- | --- | --- | --- | --- | --- | --- |
| 3154 | 0.231 | 2.255 | 3.255 | 2.247 | 2.242 | 0.123 | 0.206 | 0.331 | 0.257 | 0.346 |
| 3702 | 0.062 | 0.216 | 0.396 | 2.239 | 0.235 | 0.083 | 0.121 | 0.141 | 0.135 | 0.160 |
| 7 | 0.066 | 1.828 | 2.763 | 1.904 | 3.639 | 0.068 | 0.068 | 0.107 | 0.074 | 0.147 |
| 22 | 0.254 | 0.387 | 0.621 | 3.574 | 0.363 | 0.119 | 0.135 | 0.183 | 0.152 | 0.241 |
| 24 | 1.077 | 1.384 | 1.622 | 3.387 | 1.210 | 1.031 | 0.996 | 1.142 | 1.072 | 1.477 |
|  |  |  |  |  |  |  |  |  |  |  |
| 3154 | 0.238 | 2.261 | 3.310 | 3.200 | 2.527 | 0.201 | 0.153 | 0.352 | 0.221 |  |
| 3702 | 0.100 | 0.214 | 0.720 | 2.471 | 0.548 | 0.110 | 0.124 | 0.131 | 0.155 |  |
| 7 | 0.186 | 4.000 | 4.000 | 4.000 | 4.000 | 0.166 | 0.125 | 0.554 | 0.318 |  |
| 22 | 0.118 | 0.136 | 0.189 | 2.028 | 0.168 | 0.115 | 0.098 | 0.106 | 0.138 |  |
| 24 | 1.321 | 2.681 | 4.000 | 4.000 | 2.400 | 1.336 | 1.367 | 2.140 | 1.486 |  |

| an # | PPDB | PPDA | SEB | PPDM | Map3199 | Map1693c | Map0586c | Map4308c | Map2677c |
| --- | --- | --- | --- | --- | --- | --- | --- | --- | --- |
| 3154 | 9.8 | 14 | 9.7 | 9.7 | 0.5 | 0.9 | 1.4 | 1.1 | 1.5 |
| 3702 | 3.5 | 6.4 | 36 | 3.8 | 1.3 | 2.0 | 2.3 | 2.2 | 2.6 |
| 7 | 28 | 42 | 29 | 55 | 1.0 | 1.0 | 1.6 | 1.1 | 2.2 |
| 22 | 1.5 | 2.4 | 14 | 1.4 | 0.5 | 0.5 | 0.7 | 0.6 | 0.9 |
| 24 | 1.3 | 1.5 | 3.1 | 1.1 | 1.0 | 0.9 | 1.1 | 1.0 | 1.4 |
|  |  |  |  |  |  |  |  |  |  |
| 3154 | 9.5 | 14 | 13 | 11 | 0.8 | 0.6 | 1.5 | 0.9 |  |
| 3702 | 2.1 | 7.2 | 25 | 5.5 | 1.1 | 1.2 | 1.3 | 1.6 |  |
| 7 | 22 | 22 | 22 | 22 | 0.9 | 0.7 | 3.0 | 1.7 |  |
| 22 | 1.2 | 1.6 | 17.2 | 1.4 | 1.0 | 0.8 | 0.9 | 1.2 |  |
| 24 | 2.0 | 3.0 | 3.0 | 1.8 | 1.0 | 1.0 | 1.6 | 1.1 |  |

| an # | PPDB | PPDA | SEB | PPDM | Map3199 | Map1693c | Map0586c | Map4308c |
| --- | --- | --- | --- | --- | --- | --- | --- | --- |
| 3154 | pos | pos | pos | pos | neg | neg | neg | neg |
| 3702 | pos | pos | pos | pos | neg | neg | neg | neg |
| 7 | pos | pos | pos | pos | neg | neg | neg | neg |
| 22 | neg | pos | pos | neg | neg | neg | neg | neg |
| 24 | neg | neg | pos | neg | neg | neg | neg | neg |
|  |  |  |  |  |  |  |  |  |
| 3154 | pos | pos | pos | pos | neg | neg | neg | neg |
| 3702 | pos | pos | pos | pos | neg | neg | neg | neg |
| 7 | pos | pos | pos | pos | neg | neg | pos | neg |
| 22 | neg | neg | pos | neg | neg | neg | neg | neg |
| 24 | pos | pos | pos | neg | neg | neg | neg | neg |

Results shown in the left panel are OD readings, in the right panel are the readouts applying a stringent cutoff as per the supplier's specifications (neg = below; pos = above the cutoff), and in the central panel are colour-coded OD Indices (ODI = test antigen OD/PBS control OD) (grey = ODI < 2; bold = ODI > 2 and <4; shaded bold = ODI > 4).

Antigen-specific responses were weak and only detectable for SEQ.ID.NO.1 (MAP0586C) in the immunized animal applying standard cutoffs (Table16A, right panel). Adjusting the cutoff to less stringent conditions however resulted in three antigens being detected at one sampling point, by one calf born from an infected cow (Table16A, central panel). This shows the importance of optimising diagnostic cutoffs for optimal diagnostic performance.

In Vitro 6 Day Proliferation Assay

The same animals were simultaneously tested in the 6-day proliferation assay to assess memory T cell responses, as shown in Table 16B.

TABLE 16B

In vitro proliferative responses in 5 infected, immunised and control cattle, as described in Table 16A. Tritiated thymidine incorporation in whole blood cultures antigen-stimulated for 7 days in vitro.

| an# | PBS | PPDA | PPDB | SEB | Map3199 | Map1693c | Map0586c | Map4308c |
|---|---|---|---|---|---|---|---|---|
| 3154 | 12083 | 68714 | 44953 | 165098 | 2089 | 6162 | 1907 | 9368 |
| 3702 | 5178 | 4091 | 5729 | 71133 | 933 | 5808 | 2595 | 5934 |
| 7 | 698 | 127107 | 155933 | 130261 | 1357 | 1718 | 2407 | 22645 |
| 22 | 727 | 12755 | 1955 | 85501 | 648 | 1089 | 2925 | 1807 |
| 24 | 3777 | 5798 | 11264 | 120125 | 389 | 4607 | 1354 | 7243 |

| an# | PPDB | PPDA | SEB | Map3199 | Map1693c | Map0586c | Map4308c |
|---|---|---|---|---|---|---|---|
| 3154 | 5.7 | 3.7 | 14 | 0.2 | 0.5 | 0.2 | 0.8 |
| 3702 | 0.8 | 1.1 | 14 | 0.2 | 1.1 | 0.5 | 1.1 |
| 7 | 182 | 224 | 187 | 1.9 | 2.5 | 3.5 | 32 |
| 22 | 18 | 2.7 | 118 | 0.9 | 1.5 | 4.0 | 2.5 |
| 24 | 1.5 | 3.0 | 32 | 0.1 | 1.2 | 0.4 | 1.9 |

| an# | PPDB | PPDA | SEB | Map3199 | Map1693c | Map0586c | Map4308c |
|---|---|---|---|---|---|---|---|
| 3154 | neg | neg | pos | neg | neg | neg | neg |
| 3702 | neg | neg | pos | neg | neg | neg | neg |
| 7 | pos | pos | pos | neg | neg | neg | pos |
| 22 | pos | neg | pos | neg | neg | neg | neg |
| 24 | neg | neg | pos | neg | neg | neg | neg |

Results expressed as cpm (left panel), and stimulation indexes (SI; right panel) using a cutoff of SI = 10 (neg = below; pos = above the cutoff). (grey = SI < 10; shaded bold = SI > 10).

The detection of MAP4308C observed in the ex vivo IFN assay was confirmed in the immunized animal.

Thirty-six out of a second group of 41 calves originating from a known paratuberculosis herd were screened in a proliferation assay against 3 of the 5 MAP antigens: MAP4308C, MAP0586C and MAP2677C (FIG. 12). None of these 2-4 month old calves appeared positive in serology or by fecal culture. However, eight animals showed significant memory T cell responses against at least one antigen (SI≧18). Seven calves from this group were selected, based on their avian PPD vs bovine PPD bias and their antigen-specific reactivity, and resampled 3 weeks later for testing against the 5 Map antigens in the ex vivo IFN and proliferation assays.

20h-Ex Vivo IFN-Gamma Assay

An effector T cell response was detected in four calves out of seven against one or more of the MAP antigens (Table 17).

TABLE 17 ex vivo 20 h-IFN in seven 2 to 4-month old calves from a culture-confirmed Map herd.

| an # | PBS | PPDA | PPDB | SEB | Map3199 | Map1693c | Map0586c | Map4308c | Map2677c |
|---|---|---|---|---|---|---|---|---|---|
| 9 | 0.686 | 1.037 | 0.534 | 3.449 | 1.039 | 0.350 | 0.450 | 0.443 | 0.595 |
| 36 | 0.081 | 0.354 | 0.172 | 1.796 | 0.147 | 0.086 | 0.278 | 0.193 | 0.408 |
| 2 | 0.075 | 0.441 | 0.250 | 2.067 | 0.078 | 0.058 | 0.179 | 0.124 | 0.338 |
| 5 | 0.063 | 0.137 | 0.086 | 1.133 | 0.081 | 0.068 | 0.114 | 0.102 | 0.166 |
| 17 | 0.075 | 0.688 | 0.201 | 3.080 | 0.197 | 0.096 | 1.272 | 0.957 | 1.984 |
| 31 | 0.063 | 0.220 | 0.160 | 1.181 | 0.057 | 0.104 | 0.048 | 0.048 | 0.052 |
| 32 | 0.064 | 0.273 | 0.125 | 1.405 | 0.106 | 0.091 | 0.284 | 0.168 | 0.579 |

| an # | PPDA | PPDB | SEB | Map3199 | Map1693c | Map0586c | Map4308c | Map2677c |
|---|---|---|---|---|---|---|---|---|
| 9 | neg | neg | pos | neg | neg | neg | neg | neg |
| 36 | pos | neg | pos | neg | neg | pos | neg | pos |
| 2 | pos | pos | pos | neg | neg | neg | neg | pos |
| 5 | neg | neg | pos | neg | neg | neg | neg | neg |
| 17 | pos | neg | pos | neg | neg | pos | pos | pos |
| 31 | pos | neg | pos | neg | neg | neg | neg | neg |
| 32 | pos | neg | pos | neg | neg | pos | neg | pos |

Results shown are OD readings in the IFNγ ELISA with a PBS negative control, avian (PPDA) and bovine PPDs, a staphylococcal enteroxin β (SEB) positive control and the tested antigens, alongside IFNγ detection readout as per the supplier's specifications (neg = below; pos = above the cutoff).

As in the TB group, MAP1693C remained undetected by all animals, as well as MAP3199. MAP4308C, MAP0586C and MAP2677C were detected by 1, 3 and 4 calves respectively (FIG. 28, diamond symbols).

Proliferation Assay

Using a SI cutoff of 10, memory T cell responses to MAP1693C were detected, unlike effector responses, in 2 animals out of 7 (FIG. 13 & Table 18).

TABLE 18

In vitro proliferative responses of 7 animals selected from a paratuberculosis-infected herd. Tritiated thymidine incorporation in whole blood cultures antigen-stimulated for 7 days in vitro.

|    | PBS  | PPDA  | PPDB | SEB   | Map3199 | Map1693c | Map0586c | Map4308c | Map2677c |
|----|------|-------|------|-------|---------|----------|----------|----------|----------|
| 9  | 828  | 5164  | 1613 | 11721 | 949     | 2699     | 2870     | 2042     | 1890     |
| 36 | 642  | 2605  | 1014 | 15356 | 357     | 380      | 2217     | 470      | 1807     |
| 2  | 122  | 3438  | 2684 | 14872 | 214     | 222      | 1581     | 360      | 2714     |
| 5  | 308  | 6428  | 991  | 12379 | 373     | 3452     | 2670     | 5568     | 1577     |
| 17 | 646  | 11794 | 1389 | 19327 | 286     | 4848     | 3282     | 5609     | 2242     |
| 31 | 1164 | 2572  | 1066 | 14585 | 733     | 367      | 2602     | 657      | 3504     |
| 32 | 433  | 6903  | 1046 | 17153 | 510     | 5590     | 2398     | 7654     | 1423     |

|    | PPDA | PPDB | SEB | Map3199 | Map1693c | Map0586c | Map4308c |
|----|------|------|-----|---------|----------|----------|----------|
| 9  | neg  | neg  | pos | neg     | neg      | neg      | neg      |
| 36 | neg  | neg  | pos | neg     | neg      | neg      | neg      |
| 2  | pos  | pos  | pos | neg     | neg      | pos      | neg      |
| 5  | pos  | neg  | pos | neg     | pos      | neg      | pos      |
| 17 | pos  | neg  | pos | neg     | neg      | neg      | neg      |
| 31 | neg  | neg  | pos | neg     | neg      | neg      | neg      |
| 32 | pos  | neg  | pos | neg     | pos      | neg      | pos      |

Results expressed as cpm (left panel), and stimulation indexes (SI; right panel) using a cutoff of SI = 10 (neg = below; pos = above the cutoff).

Two animals similarily responded to MAP4308C, and only one to MAP0586C and MAP2677C each. When comparing the proportions of animals responding to single antigens in the effector T cell-based ex vivo IFN assay and in the memory T cell-based proliferation assay, the 5 antigens tested thus rank differently in terms of diagnostic potential (MAP2677c>MAP0586c>MAP4308c) versus immune memory potential (MAP4308c>MAP1693c>MAP0586c>MAP2677c) as illustrated in Table 19.

TABLE 19 summarized cellular diagnostic and vaccine potential, in cattle, of the 5 Map antigens tested.

|              | TB cattle | | | | | PTB cattle | | | | |
|--------------|---------|----------|----------|---------|----------|---------|----------|----------|----------|----------|
|              | Map3199 | Map1693c | Map0586c | Map4308 | Map2677c | Map3199 | Map1693c | Map0586c | Map4308c | Map2677c |
| IFN (diagn)  | ++      | −        | +        | −       | +        | −       | −        | ++       | +        | +++      |
| LTA (vacc)   |         |          |          |         |          | −       | ++       | +        | ++       | +        |

As a result, it appears from the cellular immune assays carried out in cattle that, whereas MAP2677c and MAP0586c show the best cellular diagnostic potential, MAP1693c and MAP4308c, with a lower diagnostic potential, present a better immunizing potential, for cattle.

Of course, the experimental results presented here are not limiting results and other candidate antigens listed in Tables 3 and 20 either alone or in combination with at least one, at least two, at least three, at least four, at least five, at least six, at least seven, at least eight, at least nine, or at least ten other candidate antigens listed in these Table 3 and 20 could also have an interesting potential both in diagnosis (serological and/or cellular) and/or in vaccination (and namely in DNA vaccination).

TABLE 20

| Nom | sequence |
|-----|----------|
| MAP0139c (SEQ. ID. NO. 8) | mwlydrpvslrdavlaallegessgydlakdfdasvanfwpatpqqlyre ldrlagqglirarvvhqqrrpnkrmfsltaagraairrftataprpsvir dellikvqaadagdmravrdairerrdwataklaryqrlrarlldgrsee dylaraerigpyltlirgisfeednirwaehalaviarrlpttdadsdag dsrlvgpatng |

TABLE 20-continued

| Nom | sequence |
|---|---|
| MAP0494 (SEQ. ID. NO. 9) | mmrplsrhwcrvmgplshhskeqlvrvlvtgasggigsavvkellaaghh viglarseasaatvsglgaeplrgdiadldvlqkaavdtdgvaylafshd fsdvgdaiadearaidalgaaladtgkplvlasgtparpgvsteddpfia dgplagrgrtgqavvalagrgvrsavvrlpravhdaggryglvgiliqla rqrgvssfagdgtqrwpavhrddaaalfrlaleqapagsvlhavgdegvp lraiaevigrrlgvpvesapadtfgplgqvfavdqpsssaltqrrfgwqp vgpglllddletgvype |
| MAP0586c (SEQ. ID. NO. 1) | msnrrtaplvaaavlvalagcspshpsaaprptatrtaapsapasrmlpa dadtpggaqprlasdpaqlgddlvaderalrdpgtsepaltaaahreqaa yraiarhpeweaaargrippelidvydrnvdarrqltalt pvrntlpawrieppapadellgyyhqaeaesgvgwnylaainfietrfgs ivgastagaggpmqflpstfagygqggdihsprdsilaagrylaangfaa drdhaiyaynhaseyvravdqyaalmaadpatfaayyrwdvycfttagdv llpigydasspipaadyvaahpq |
| MAP0740c (SEQ. ID. NO. 10) | mpsievnggnvvyeilgdsgdlialtpggrfsmqipglrpladalvaggy rvllwdrpncgasdvqfygpseshmraetlhklvtglgfercilaggsgg ardsmlttmlypemvtklvvwnivggiygtfvlgsfyiipsilavrgtgm dgvikvqewrerieenpankqrfldfdsgeflkvmlrwlnafvskpgqti pgvedemfdritvptliirggendmdhpkrtslevsclikgsklidppwp edawerasedraagrvqhfnmfdtwvqaapaileflgs |
| MAP0796c (SEQ. ID. NO. 11) | mtvtvilelrfkpdevaagrelmgralqdtrafdgnvrtdvlvdeddeah wlvyeiwetvehdqayrafragegkltqlppllaappvktryvtsdi |
| MAP0907 (SEQ. ID. NO. 6) | mskvptielndgaripqlgfgvyqikpdetaaavraaldigyrhidtaem ygnerevaqgirdagldrsevfvtsklnngfhepdaarrafdatlnalgs dyvdlflihwplptlyggdfvstwrvleefardgrarsigvsnfqvahle rlaaetdtvpavngvevhpyftnekvrgyarehglaieawspiaqggvlg davinriadglgrtaaqvvlrwhiqrgdivfpktvnpdrmksnfelfdfe lderameaisaldrgesgrrgpnpdtfdyipr |
| MAP1168c (SEQ. ID. NO. 12) | msagiilmahpdaanlvddviaqarrahefgvgqvwlaqqqsydaialaa lvgaavpglgvgtsvvpinprhplivaslaqtaqaaahgnfslglglgaa dlerrtfgtewpntitrlrehltilgsvfhsgavdfhgselsaapsfpvr vpggtpipvyvaamgpkalqvtgeladgtlpylagprtieefivpritka aaeagrpapriiaavpvllsddvegaraaaaqqlsfyetipsyrnviare glsnavelaaigpeesvlrqvrryfdagatdvvlspldrsasvdrealwr ltaal |
| MAP1438c (SEQ. ID. NO. 13) | mtsppldpdaaariasfgetapmrqrglpavraglesaprpatmpemasv tealvpsaaggipvriyrpttdsgvavlvylhggglvmgsnrsfeplare lasasasaatvvavdyrlapespppaqfddayaatewvsrkagelgvdadrl avigdsaggslaaavalaardrrgppicaqvllypgldrdmsvasiaamp daplllirddidymhalvdgdagpptdpylvpayaadlsglppaivvtagc dpirdwgeryadrlrdagvqttvtrypgmyhgflmrsdatargrlaiaei ggllrakfshplrfdvpitg rhstatr |
| MAP1562c (SEQ. ID. NO. 14) | mtkrasaaaiavgvafaptavahadnngiamaisdstghisiadgaasqg aaekaamdtcrksisdcrllasgqggcmalvlnaskskyfgawgptreea eaaalarvpggtvqeghdhcagegspq |
| MAP1693c (SEQ. ID. NO. 4) | mtavnsvrtfsaaafaacftaaaamlagagtagaadscptaappsggtpd wtltgttgsvavtgstdtaapvvnvtapfsvtqtqvhtlragdgpavpgt arvsvcymgvngrdgtvfdssyqrgapvdfplggvvpgfqkaiagqkvgs tvavamtsadgypdgqpsagirpgdtivfaikilgatt |
| MAP2411 (SEQ. ID. NO. 15) | mkpfsesergeflagthvavlsveatdgrppaavpiwydytpggdirimt gassrkarlieragkvtvvvqreeppyqyvvvvegtvvdatkpapsdvqla vairylgedggrafvqslegveevlftirpdrwlsadftgdl |
| MAP2677c (SEQ. ID. NO. 2) | mkfvstriitadvqrlvgfyemvtrvsavwanelfaeiptpaatlaigsd qtvplfgagsaepaanrsaivefivddvdaeyerlreqltevvteptttmp wgnrallfrdpdgnlvnlftpvtpearakfkv |
| MAP2746 (SEQ. ID. NO. 16) | mavvwagaappgaprvalvsgeaiaiaqgvsvtpapgwtlgnrgpnwval nnsdttaqlritvkpgagtdaaallqadvdqytggasailtdvnrlgppe ttplqgpnfqqqaslnytatvvhpqgsipvigtftellntstgrsafvdf rqdssattqaagegaamiaslq |
| MAP2770 (SEQ. ID. NO. 17) | mrylqpvtrparmstlaaalaltacltapgatadptpqqspfptgksgtt ihvteystatadvtlnsatwvssgcpggggcnvieltiagksdkpftysq asitaastpwrqdpyrdtqggssladyqqlnktpplrvgsvtngqtahgf iaydgairqgdvyiefndpdapaaptplagwkvht |

TABLE 20-continued

| Nom | sequence |
| --- | --- |
| MAP2963c (SEQ.ID. NO. 18) | mikkmgyrwrlrdlmadqqmfkttdliphlvergitlsreqvfrlvtqpp qrlsmdtivalcdilgctpndlivlevvnkpvrktagaggewcagghaqk nsrttawqvmtrphstapiahvreslvssvisavgsgmtrqraqqllvea kgwstanarhlheylgenpgaftapthecpaafprlltllaaaghadavs llgcakcgrtdlalrrnspegrccpwcvirtelrpcarcgedgyiiarra dgpvcrrcynkdpqflqvcagcgrkrppnarrddgtvlcqrcslpptqsc crcgnvrrvhaqtadgpicrtcyrsparkcgvcgeiaqiqaratdthpdt cvrcyrnigecvvcgrtraggkyrggslhcvtcwphhprhcdscekpgia catwplgtvcrdcyhrrrlhpqpcanchrtavmvgrnpdgqdicapccgv dldfscrtcgieglnyadgkctccvmtdrvnvllslddgtvvpqlqplad alsaanpesvqtwlqasssarllaqlvaerraishelldeldqdnatryi rqllvttgiltsrqeefaqlqiwasrkighlpphqsrvvrpfaewrvird arkraarrrytigsaandrqkisttiafltwlddqeipldsvtqlhldrw ldahptkhkyaafigwlekqrltqaelvvpqrrsqlpsrllsddeleqql krcltddtlpldvrvvgalirlyapplvriaelttdryhtdddgsyltig rhpvllpptlarliegliargpvntlllrngsadnpayllagrppsrpvnp rslqqrltkhglpviharntamitnaatlpppvvaelfgihpttayqwaq yaqsswaaylqacqstaqpglrc |
| MAP3199 (SEQ.ID. NO. 5) | mttletlllhdpemagvwnlvpdrsaitfriknmwglltvrgrftdftgdg qltgkgavfgrvdiraasldtgigrrdqhlrspdffdverfekisvvvtg lqptkgkiadlrtdftvkgvtaqlplpvtileldddgsiritgettldrar fdlgwnrfgmigrtataaadvifvrdsq |
| MAP3385 (SEQ.ID. NO. 19) | martdddtwdlatsvgatatmvaagraratrdgliddpfaeplvravgvd fftrwaageldaadvdvpgaawgmqrmtdmltartryidaffaeagaagi rqvvilasgldarayrlpwpagttvfeidqprvlefkaatiaqlgaepta pvravavdlrhdwpsalrqagfdvgrpaawaaegllgflppqaqdrildn vtalsadgsqlvaevfantgasgdalnaagekwrrhgldvalddlgfpge rndpasylqqlgwqpvrtpinqmlannglplqstepgapfaqnyyctavl nkag |
| MAP3486 (SEQ.ID. NO. 20) | mafaeyqnelydqslhgnqpqypirfeeleakasaamtpkvlgyvaggag dehtqranceafkrwglyprmgiapeqrdmsvelfgtrfpspifmapigv igvcdpdghgdlacvrasirtgvpffvgtlsadpmedladelgdtpaffq lytppdrkmaaslvhraeeaasfsgiavtldtwvtgwrprdlsggnypqvp sgclanytsdpvfraglsrgedpteaavrklpifggpfrwedlewlrsrt slplmakgichpddvrrakdigvdavycsnhggrqangglpcldclpgvv eaadglplfdsgvrsgadivkalalgatavgigrpyayglalggvdgiv hvlrsllaeadlimavdgypslkdltpdalrrvehvapqrys |
| MAP3547c (SEQ.ID. NO. 7) | mthestaawrellaalgeldrsflegdravsddrhiadgyrmlattlgva fdtylfpepdrpqfvavntpfrrdrrwggdntdayyficpvdpkrryris gnkgdsvyfsvtaynepslgawsdrvvaivrdsdldvdadgnfsfefppt pdaavlmtrdyqadpltgrpvtwriealdepapirhgdaetaarlravat wirtmfaivplavgnrvddqhalghetahaanafadpyqvpdanfgwsar dacysygsfvldddealvithrppscrfwnmvvwnqfmatygaaegpdar csinghsavansdgtvtivlsrdrtphpnsvttlgyprgnlafrwfladg vparpevelvkaadaptavr |
| MAP3680c (SEQ.ID. NO. 21) | meeepvakcvmvlypdpvdgyppkyardsipvinsypdgssltptpskidf tpgellgcvsgalglrkffedgghelvvtsdkdgpdseferelpdadivi sqpfwpayitkerfakarnlklaltagigsdhvdlaeaqargvtvaeetw snsisvaehtvmqilalvrnfvpshqwirdggwniadcvqrsydvegmdv gviaagrigravlermkpfgvnlhyfdvhrlspeyekqlgvtyhpdvesl arsvdvvsihspliaqthhmfneklllksmrrgsyivntaraeetdhkaiv aalesgqlagyagdvwfpqppppdhpwrtmpnhamtphisgssl saqary cagtreiledwfagrpirseylivegkfagtgaksyaq |
| MAP3731c (SEQ.ID. NO. 22) | miridgvrwqyagtdaavldgvdlhirrgetvllcgasgsgkssvlrlmn gliphfhqgsldgsvhidgtsvaelslervgrltgtvlqhprrqfftaav dtelaftlenfgtppegirnrvgsviteyglaeltghrlaelsggqqqqi acaaaathgpplllfdeptanlaadaierftatlarlrslgttiviaehr lhylreiadrivllrngriaaewsrkqfarlddaalnaeglrsnnspvrn hippacaygasvagtpsgtaapasspsevvlrgirccfrghrvldieear fpaatvtaitgpngagkstlarvlvglqrhdgevsfggsrisrsrrqrms aivmqdvqrqlftesvraelrlgappaaagvastllrdlgleefadrhpl slsggqqqrlvvaaarlsnrkimvfdepssgvdrrhlrsitnvmrdvaaq gvvvilishdqelltlaadqelrmrvadtlnarsrrkaagenacletlsd |
| MAP3804 (SEQ.ID. NO. 23) | mdrrsmmlmsgigmlgaamrlpgawatppapeappsagggpyifadefdg pagsppdpgkwtiqtwqddvfppvagiyrddrrnvfqdgnsnlvlcatqe mgtyysgklrgnfrsminqtweariklclfpglwpsfwgvnedplpdge vdifewygngqwppgttvhaasngktwegksipglvdgnwhtwrmhwgee gfefsrdgaeyfkvpnkpihvaggapddfrwpfnnpgywmtpmftlavgg vgagdpaagvfpssmlidyiriw |

TABLE 20-continued

| Nom | sequence |
|---|---|
| MAP4056c (SEQ.ID. NO. 24) | mlatigaaavaafalaapaqlsapaqadppptapyptprtpsppsdydap fkntvngfgiyqpqdqlawlgkitcdrldhgvdhdahqsatfiqrnlprg tsegqslqflgaavdhycpehidvvqaagr |
| MAP4096 (SEQ.ID. NO. 25) | meawdaicarrnvreyqpraiagedldriveagwrapsaknrqpwdfviv tdrtqlqelstvwrgaghiagapaaiaivvpeppderrvvtdnydvgqat mammiaatdlgigtghssvgdqdkarailgvpdghlvafllgvgypadrp ltpirkpnrrpftevvhrgrw |
| MAP4308c (SEQ.ID. NO. 3) | mpvramrkwessmsnqqqaermtsgkgfiaaldqsggstpkalrlygied sayssekemfdlihqmrsriitspaftgdrvlaailfeqtmdrdiegkps ttylwetkgvvpilkidkglaeasddvqlmkpipgldellqrayskgvfg tkersvigganpvgiaavvaqqfelahqvlshglvpiiepevtisiadka kaegilrdeitkqldsvpdgqrvmlklslpteanfyrpliehpkvmrvva lsggysreeanellaknagliasfsraltegltvdqsdeqfnatldkaiq siydasvag |

BIBLIOGRAPHICAL REFERENCES

1. Rosseels, V., Roupie, V., Zinniel, D., Barletta, R. G., and Huygen, K. (2006) Development of luminescent *Mycobacterium avium* subsp. *paratuberculosis* for rapid screening of vaccine candidates in mice. *Infect Immun* 74, 3684-3686
2. Noel-Georis, I., Bernard, A., Falmagne, P., and Wattiez, R. (2002) Database of bronchoalveolar lavage fluid proteins. *J Chromatogr B Analyt Technol Biomed Life Sci* 771, 221-236
3. Walravens, K., Marche, S., Rosseels, V., Wellemans, V., Boelaert, F., Huygen, K., and Godfroid, J. (2002) IFN-gamma diagnostic tests in the context of bovine mycobacterial infections in Belgium. *Vet Immunol Immunopathol* 87, 401-406
4. Rosseels, V., Marche, S., Roupie, V., Govaerts, M., Godfroid, J., Walravens, K., and Huygen, K. (2006) Members of the 30- to 32-kilodalton mycolyl transferase family (Ag85) from culture filtrate of *Mycobacterium avium* subsp. *paratuberculosis* are immunodominant Th1-type antigens recognized early upon infection in mice and cattle. *Infect Immun* 74, 202-212
5. Tanghe, A., Content, J., Van Vooren, J. P., Portaels, F., and Huygen, K. (2001) Protective efficacy of a DNA vaccine encoding antigen 85A from *Mycobacterium bovis* BCG against Buruli ulcer. *Infect Immun* 69, 5403-5411
6. Moss, M. T., E. P. Green, M. L. Tizard, Z. P. Malik, and J. Hermon-Taylor (1991) Specific detection of *Mycobacterium paratuberculosis* by DNA hybridisation with a fragment of the insertion element IS900. Gut 32:395-8
7. Vordermeier, H. M., Whelan, A., Cockle, P. J., Farrant, L., Palmer, N., and Hewinson, R. G. (2001) Use of synthetic peptides derived from the antigens ESAT-6 and CFP-10 for differential diagnosis of bovine tuberculosis in cattle. *Clin Diagn Lab Immunol* 8, 571-578
8. Magnusson, M., and M. W. Bentzon (1958) Preparation of purified tuberculin RT 23. Bull World Health Organ 19:829-43.
9. Sugden, E. A., Stilwell, K., and Michaelides, A. (1997) A comparison of lipoarabinomannan with other antigens used in absorbed enzyme immunoassays for the serological detection of cattle infected with *Mycobacterium paratuberculosis*. *J Vet Diagn Invest* 9, 413-417
10. Walravens, K., Wellemans, V., Weynants, V., Boelaert, F., deBergeyck, V., Letesson, J. J., Huygen, K., and Godfroid, J. (2002) Analysis of the antigen-specific IFN-gamma producing T-cell subsets in cattle experimentally infected with *Mycobacterium bovis*. Vet Immunol Immunopathol 84, 29-41

The invention claimed is:

1. An isolated antigen of *Mycobacterium avium* subsp. *paratuberculosis*, said antigen comprising the amino acid sequence SEQ.ID.NO.1.

2. An antigenic composition of *Mycobacterium avium* subsp. *paratuberculosis* comprising the isolated antigen according to claim 1 and at least an isolated antigen comprising the amino acid sequence SEQ.ID.NO.2.

3. The antigenic composition according to claim 2, further comprising an isolated antigen comprising the amino acid sequence SEQ.ID.NO.3.

4. The antigenic composition according to claim 2, further comprising an isolated antigen comprising the amino acid sequence SEQ.ID.NO.4.

5. The antigenic composition according to claim 2, further comprising an isolated antigen comprising the amino acid sequence SEQ.ID.NO.5.

6. The antigenic composition according to claim 2, further comprising at least an isolated antigen comprising the amino acid sequence SEQ.ID.NO.6.

7. The antigenic composition according to claim 2, further comprising an isolated antigen comprising the amino acid sequence SEQ.ID.NO.7.

8. An antigenic composition of *Mycobacterium avium* subsp. *paratuberculosis* comprising the isolated antigen according to claim 1 and at least one isolated antigen comprising the amino acid sequence SEQ.ID.NO.3 and an isolated antigen comprising the amino acid sequence SEQ.ID.NO.4.

9. An antigenic composition of *Mycobacterium avium* subsp. *paratuberculosis* comprising the isolated antigen according to claim 1 and an isolated antigen comprising the amino acid sequence SEQ.ID.NO.3.

10. An antigenic composition of *Mycobacterium avium* subsp. *paratuberculosis* comprising the isolated antigen according to claim 1 and an isolated antigen comprising the amino acid sequence SEQ.ID.NO.4.

11. An antigenic composition of *Mycobacterium avium* subsp. *paratuberculosis* comprising the isolated antigen according to claim 1 and at least one, at least two, at least three, at least four, at least five or at least six isolated antigen(s) comprising an amino acid sequence selected from the group consisting of SEQ.ID.NO.2, SEQ.ID.NO.3, SEQ.ID.NO.4, SEQ.ID.NO.5, SEQ.ID.NO.6 and SEQ.ID.NO.7.

12. The antigenic composition according to claim 11, further comprising at least one isolated antigen comprising an amino acid sequence selected from the group consisting of SEQ.ID.NO.8 to SEQ.ID.NO.25.

13. An isolated antibody or hypervariable fragment thereof directed against the amino acid sequence SEQ.ID.NO.1 of the antigen according to claim 1.

14. An isolated nucleotide sequence encoding the antigen according to claim 1.

15. A pharmaceutical composition comprising an adequate pharmaceutical carrier and the antigenic composition according to claim 2 or an isolated nucleotide sequence encoding the antigen of claim 2 comprising the amino acid sequence of SEQ.ID.NO.1 or SEQ.ID.NO.2.

16. A diagnostic kit for the cellular diagnosis of *Paratuberculosis* in mammals, comprising the antigenic composition according to the claim 2 or an isolated nucleotide sequence encoding the antigen of claim 2 comprising the amino acid sequence of SEQ.ID.NO.1 or SEQ.ID.NO.2.

17. A pharmaceutical composition comprising an adequate pharmaceutical carrier and the antigen according to claim 1 or an isolated nucleotide sequence encoding the antigen according to claim 1.

18. A diagnostic kit for the cellular diagnosis of *Paratuberculosis* in mammals, comprising the antigen according to the claim 1 or an isolated nucleotide sequence encoding the antigen according to claim 1.

19. A diagnostic it for diagnosis of *Paratuberculosis* in mammals, the kit comprising the isolated antibody of claim 13, or a hypervariable fragment thereof, and a reagent to detect binding of the antibody or hypervariable fragment to antigen.

20. A diagnostic kit for diagnosis of *Paratuberculosis* in mammals, comprising the isolated antibody, or a hypervariable fragment thereof, directed against the amino acid sequence SEQ.ID.NO.1 and an isolated antibody, or a hypervariable fragment thereof, directed against the amino acid sequence SEQ.ID.NO.2 of the antigen according to claim 2.

* * * * *

SEQUENCE LISTING

```
<160> NUMBER OF SEQ ID NOS: 60

<210> SEQ ID NO 1
<211> LENGTH: 313
<212> TYPE: PRT
<213> ORGANISM: Mycobacterium avium
<220> FEATURE:
<221> NAME/KEY: MISC_FEATURE
<223> OTHER INFORMATION: Mycobacterium avium subsp. Paratuberculosis
      bovis

<400> SEQUENCE: 1
```

Met Ser Asn Arg Arg Thr Ala Pro Leu Val Ala Ala Val Leu Val
1               5                   10                  15

Ala Leu Ala Gly Cys Ser Pro Ser His Pro Ser Ala Ala Pro Arg Pro
            20                  25                  30

Thr Ala Thr Arg Thr Ala Ala Pro Ser Ala Pro Ala Ser Arg Met Leu
        35                  40                  45

-continued

Pro Ala Asp Ala Asp Thr Pro Gly Ala Gln Pro Arg Leu Ala Ser
        50                  55                  60

Asp Pro Ala Gln Leu Gly Asp Leu Val Ala Asp Glu Arg Ala Leu
65                  70                  75                  80

Arg Asp Pro Gly Thr Ser Glu Pro Ala Leu Thr Ala Ala His Arg
                85                  90                  95

Glu Gln Ala Ala Tyr Arg Ala Ile Ala Arg His Pro Gly Trp Glu Ala
            100                 105                 110

Ala Ala Arg Gly Arg Ile Pro Pro Glu Leu Ile Asp Val Tyr Asp Arg
            115                 120                 125

Asn Val Asp Ala Arg Arg Gln Leu Thr Ala Leu Thr Pro Val Arg Asn
        130                 135                 140

Thr Leu Pro Ala Trp Arg Ile Glu Pro Ala Pro Ala Asp Glu Leu
145                 150                 155                 160

Leu Gly Tyr Tyr His Gln Ala Glu Ala Glu Ser Gly Val Gly Trp Asn
                165                 170                 175

Tyr Leu Ala Ala Ile Asn Phe Ile Glu Thr Arg Phe Gly Ser Ile Val
            180                 185                 190

Gly Ala Ser Thr Ala Gly Ala Gln Gly Pro Met Gln Phe Leu Pro Ser
        195                 200                 205

Thr Phe Ala Gly Tyr Gly Gln Gly Gly Asp Ile His Ser Pro Arg Asp
210                 215                 220

Ser Ile Leu Ala Ala Gly Arg Tyr Leu Ala Ala Asn Gly Phe Ala Ala
225                 230                 235                 240

Asp Arg Asp His Ala Ile Tyr Ala Tyr Asn His Ala Ser Glu Tyr Val
                245                 250                 255

Arg Ala Val Asp Gln Tyr Ala Ala Leu Met Ala Ala Asp Pro Ala Thr
            260                 265                 270

Phe Ala Ala Tyr Tyr Arg Trp Asp Val Tyr Cys Phe Thr Thr Ala Gly
        275                 280                 285

Asp Val Leu Leu Pro Ile Gly Tyr Asp Ala Ser Ser Pro Ile Pro Ala
290                 295                 300

Ala Asp Tyr Val Ala Ala His Pro Gln
305                 310

<210> SEQ ID NO 2
<211> LENGTH: 132
<212> TYPE: PRT
<213> ORGANISM: Mycobacterium avium
<220> FEATURE:
<221> NAME/KEY: MISC_FEATURE
<223> OTHER INFORMATION: Mycobacterium avium subsp. Paratuberculosis
      bovis

<400> SEQUENCE: 2

Met Lys Phe Val Ser Thr Arg Ile Ile Thr Ala Asp Val Gln Arg Leu
1               5                   10                  15

Val Gly Phe Tyr Glu Met Val Thr Arg Val Ser Ala Val Trp Ala Asn
                20                  25                  30

Glu Leu Phe Ala Glu Ile Pro Thr Pro Ala Ala Thr Leu Ala Ile Gly
            35                  40                  45

Ser Asp Gln Thr Val Pro Leu Phe Gly Ala Gly Ser Ala Glu Pro Ala
        50                  55                  60

Ala Asn Arg Ser Ala Ile Val Glu Phe Ile Val Asp Asp Val Asp Ala
65                  70                  75                  80

Glu Tyr Glu Arg Leu Arg Glu Gln Leu Thr Glu Val Val Thr Glu Pro

```
                    85                  90                  95
Thr Thr Met Pro Trp Gly Asn Arg Ala Leu Leu Phe Arg Asp Pro Asp
            100                 105                 110

Gly Asn Leu Val Asn Leu Phe Thr Pro Val Thr Pro Glu Ala Arg Ala
            115                 120                 125

Lys Phe Lys Val
            130

<210> SEQ ID NO 3
<211> LENGTH: 309
<212> TYPE: PRT
<213> ORGANISM: Mycobacterium avium
<220> FEATURE:
<221> NAME/KEY: MISC_FEATURE
<223> OTHER INFORMATION: Mycobacterium avium subsp. Paratuberculosis
      bovis

<400> SEQUENCE: 3

Met Pro Val Arg Ala Met Arg Lys Trp Glu Ser Ser Met Ser Asn Gln
1               5                   10                  15

Gln Gln Ala Glu Arg Met Thr Ser Gly Lys Gly Phe Ile Ala Ala Leu
            20                  25                  30

Asp Gln Ser Gly Gly Ser Thr Pro Lys Ala Leu Arg Leu Tyr Gly Ile
        35                  40                  45

Glu Asp Ser Ala Tyr Ser Ser Glu Lys Glu Met Phe Asp Leu Ile His
    50                  55                  60

Gln Met Arg Ser Arg Ile Ile Thr Ser Pro Ala Phe Thr Gly Asp Arg
65                  70                  75                  80

Val Leu Ala Ala Ile Leu Phe Glu Gln Thr Met Asp Arg Asp Ile Glu
                85                  90                  95

Gly Lys Pro Ser Thr Thr Tyr Leu Trp Glu Thr Lys Gly Val Val Pro
            100                 105                 110

Ile Leu Lys Ile Asp Lys Gly Leu Ala Glu Ala Ser Asp Val Gln
            115                 120                 125

Leu Met Lys Pro Ile Pro Gly Leu Asp Glu Leu Leu Gln Arg Ala Val
        130                 135                 140

Ser Lys Gly Val Phe Gly Thr Lys Glu Arg Ser Val Ile Gly Gly Ala
145                 150                 155                 160

Asn Pro Val Gly Ile Ala Ala Val Val Ala Gln Gln Phe Glu Leu Ala
                165                 170                 175

His Gln Val Leu Ser His Gly Leu Val Pro Ile Ile Glu Pro Glu Val
            180                 185                 190

Thr Ile Ser Ile Ala Asp Lys Ala Lys Ala Glu Gly Ile Leu Arg Asp
        195                 200                 205

Glu Ile Thr Lys Gln Leu Asp Ser Val Pro Asp Gly Gln Arg Val Met
    210                 215                 220

Leu Lys Leu Ser Leu Pro Thr Glu Ala Asn Phe Tyr Arg Pro Leu Ile
225                 230                 235                 240

Glu His Pro Lys Val Met Arg Val Val Ala Leu Ser Gly Gly Tyr Ser
                245                 250                 255

Arg Glu Glu Ala Asn Glu Leu Leu Ala Lys Asn Ala Gly Leu Ile Ala
            260                 265                 270

Ser Phe Ser Arg Ala Leu Thr Glu Gly Leu Thr Val Asp Gln Ser Asp
        275                 280                 285

Glu Gln Phe Asn Ala Thr Leu Asp Lys Ala Ile Gln Ser Ile Tyr Asp
    290                 295                 300
```

Ala Ser Val Ala Gly
305

<210> SEQ ID NO 4
<211> LENGTH: 188
<212> TYPE: PRT
<213> ORGANISM: Mycobacterium avium
<220> FEATURE:
<221> NAME/KEY: MISC_FEATURE
<223> OTHER INFORMATION: Mycobacterium avium subsp. Paratuberculosis
      bovis

<400> SEQUENCE: 4

Met Thr Ala Val Asn Ser Val Arg Thr Phe Ser Ala Ala Phe Ala
1               5                   10                  15

Ala Cys Phe Thr Ala Ala Ala Met Leu Ala Gly Ala Gly Thr Ala
                20                  25                  30

Gly Ala Ala Asp Ser Cys Pro Thr Ala Ala Pro Pro Ser Gly Gly Thr
            35                  40                  45

Pro Asp Trp Thr Leu Thr Gly Thr Thr Gly Ser Val Ala Val Thr Gly
    50                  55                  60

Ser Thr Asp Thr Ala Ala Pro Val Val Asn Val Thr Ala Pro Phe Ser
65                  70                  75                  80

Val Thr Gln Thr Gln Val His Thr Leu Arg Ala Gly Asp Gly Pro Ala
                85                  90                  95

Val Pro Gly Thr Ala Arg Val Ser Val Cys Tyr Met Gly Val Asn Gly
            100                 105                 110

Arg Asp Gly Thr Val Phe Asp Ser Ser Tyr Arg Gln Gly Ala Pro Val
        115                 120                 125

Asp Phe Pro Leu Gly Gly Val Val Pro Gly Phe Gln Lys Ala Ile Ala
    130                 135                 140

Gly Gln Lys Val Gly Ser Thr Val Ala Val Ala Met Thr Ser Ala Asp
145                 150                 155                 160

Gly Tyr Pro Asp Gly Gln Pro Ser Ala Gly Ile Arg Pro Gly Asp Thr
                165                 170                 175

Leu Val Phe Ala Ile Lys Ile Leu Gly Ala Thr Thr
            180                 185

<210> SEQ ID NO 5
<211> LENGTH: 178
<212> TYPE: PRT
<213> ORGANISM: Mycobacterium avium
<220> FEATURE:
<221> NAME/KEY: MISC_FEATURE
<223> OTHER INFORMATION: Mycobacterium avium subsp. Paratuberculosis
      bovis

<400> SEQUENCE: 5

Met Thr Thr Leu Glu Thr Leu Leu His Asp Pro Glu Met Ala Gly Val
1               5                   10                  15

Trp Asn Leu Val Pro Asp Arg Ser Ala Ile Thr Phe Arg Ile Lys Asn
                20                  25                  30

Met Trp Gly Leu Leu Thr Val Arg Gly Arg Phe Thr Asp Phe Thr Gly
            35                  40                  45

Asp Gly Gln Leu Thr Gly Lys Gly Ala Val Phe Gly Arg Val Asp Ile
    50                  55                  60

Arg Ala Ala Ser Leu Asp Thr Gly Ile Gly Arg Asp Gln His Leu
65                  70                  75                  80

Arg Ser Pro Asp Phe Phe Asp Val Glu Arg Phe Glu Lys Ile Ser Val
                85                  90                  95

```
Val Val Thr Gly Leu Gln Pro Thr Lys Gly Lys Ile Ala Asp Leu Arg
            100                 105                 110

Thr Asp Phe Thr Val Lys Gly Val Thr Ala Gln Leu Pro Leu Pro Val
            115                 120                 125

Thr Ile Leu Glu Leu Asp Asp Gly Ser Ile Arg Ile Thr Gly Glu Thr
            130                 135                 140

Thr Leu Asp Arg Ala Arg Phe Asp Leu Gly Trp Asn Arg Phe Gly Met
145                 150                 155                 160

Ile Gly Arg Thr Ala Thr Ala Ala Asp Val Ile Phe Val Arg Asp
            165                 170                 175

Ser Gln

<210> SEQ ID NO 6
<211> LENGTH: 282
<212> TYPE: PRT
<213> ORGANISM: Mycobacterium avium
<220> FEATURE:
<221> NAME/KEY: MISC_FEATURE
<223> OTHER INFORMATION: Mycobacterium avium subsp. Paratuberculosis
      bovis

<400> SEQUENCE: 6

Met Ser Lys Val Pro Thr Ile Glu Leu Asn Asp Gly Ala Arg Ile Pro
1               5                   10                  15

Gln Leu Gly Phe Gly Val Tyr Gln Ile Lys Pro Asp Glu Thr Ala Ala
            20                  25                  30

Ala Val Arg Ala Ala Leu Asp Ile Gly Tyr Arg His Ile Asp Thr Ala
            35                  40                  45

Glu Met Tyr Gly Asn Glu Arg Glu Val Ala Gln Gly Ile Arg Asp Ala
        50                  55                  60

Gly Leu Asp Arg Ser Glu Val Phe Val Thr Ser Lys Leu Asn Asn Gly
65                  70                  75                  80

Phe His Glu Pro Asp Ala Ala Arg Arg Ala Phe Asp Ala Thr Leu Asn
                85                  90                  95

Ala Leu Gly Ser Asp Tyr Val Asp Leu Phe Leu Ile His Trp Pro Leu
            100                 105                 110

Pro Thr Leu Tyr Gly Gly Asp Phe Val Ser Thr Trp Arg Val Leu Glu
            115                 120                 125

Glu Phe Ala Arg Asp Gly Arg Ala Arg Ser Ile Gly Val Ser Asn Phe
            130                 135                 140

Gln Val Ala His Leu Glu Arg Leu Ala Ala Glu Thr Asp Thr Val Pro
145                 150                 155                 160

Ala Val Asn Gln Val Glu Val His Pro Tyr Phe Thr Asn Glu Lys Val
                165                 170                 175

Arg Gly Tyr Ala Arg Glu His Gly Leu Ala Ile Glu Ala Trp Ser Pro
            180                 185                 190

Ile Ala Gln Gly Gly Val Leu Gly Asp Ala Val Ile Asn Arg Ile Ala
            195                 200                 205

Asp Gly Leu Gly Arg Thr Ala Ala Gln Val Val Leu Arg Trp His Ile
            210                 215                 220

Gln Arg Gly Asp Ile Val Phe Pro Lys Thr Val Asn Pro Asp Arg Met
225                 230                 235                 240

Lys Ser Asn Phe Glu Leu Phe Asp Phe Glu Leu Asp Glu Arg Ala Met
                245                 250                 255

Glu Ala Ile Ser Ala Leu Asp Arg Gly Glu Ser Gly Arg Arg Gly Pro
            260                 265                 270
```

Asn Pro Asp Thr Phe Asp Tyr Ile Pro Arg
        275                 280

<210> SEQ ID NO 7
<211> LENGTH: 370
<212> TYPE: PRT
<213> ORGANISM: Mycobacterium avium
<220> FEATURE:
<221> NAME/KEY: MISC_FEATURE
<223> OTHER INFORMATION: Mycobacterium avium subsp. Paratuberculosis
      bovis

<400> SEQUENCE: 7

Met Thr His Glu Ser Thr Ala Ala Trp Arg Glu Leu Leu Ala Ala Leu
1               5                   10                  15

Gly Glu Leu Asp Arg Ser Phe Leu Glu Gly Asp Arg Ala Val Ser Asp
            20                  25                  30

Asp Arg His Ile Ala Asp Gly Tyr Arg Met Leu Ala Thr Thr Leu Gly
        35                  40                  45

Val Ala Phe Asp Thr Tyr Leu Phe Pro Glu Pro Asp Arg Pro Gln Phe
    50                  55                  60

Val Ala Val Asn Thr Pro Phe Arg Arg Asp Arg Arg Trp Gly Gly Asp
65                  70                  75                  80

Asn Thr Asp Ala Tyr Tyr Phe Ile Cys Pro Val Asp Pro Lys Arg Arg
                85                  90                  95

Tyr Arg Ile Ser Gly Asn Lys Gly Asp Ser Val Tyr Phe Ser Val Thr
            100                 105                 110

Ala Tyr Asn Glu Pro Ser Leu Gly Ala Trp Ser Asp Arg Val Val Ala
        115                 120                 125

Ile Val Arg Asp Ser Asp Leu Asp Val Asp Ala Asp Gly Asn Phe Ser
    130                 135                 140

Phe Glu Phe Pro Pro Thr Pro Asp Ala Ala Val Leu Met Thr Arg Asp
145                 150                 155                 160

Tyr Gln Ala Asp Pro Leu Thr Gly Arg Pro Val Thr Trp Arg Ile Glu
                165                 170                 175

Ala Leu Asp Glu Pro Ala Pro Ile Arg His Gly Asp Ala Glu Thr Ala
            180                 185                 190

Ala Arg Leu Arg Ala Val Ala Thr Trp Leu Arg Thr Met Phe Ala Ile
        195                 200                 205

Val Pro Leu Ala Val Gly Asn Arg Val Asp Asp Gln His Ala Leu Gly
    210                 215                 220

His Glu Thr Ala His Ala Ala Asn Ala Phe Ala Asp Pro Tyr Gln Val
225                 230                 235                 240

Pro Asp Ala Asn Phe Gly Trp Ser Ala Arg Asp Ala Cys Tyr Ser Tyr
                245                 250                 255

Gly Ser Phe Val Leu Asp Asp Asp Glu Ala Leu Val Ile Thr His Arg
            260                 265                 270

Pro Pro Ser Cys Arg Phe Trp Asn Met Val Val Trp Asn Gln Phe Met
        275                 280                 285

Ala Thr Tyr Gly Ala Ala Glu Gly Pro Asp Ala Arg Cys Ser Ile Asn
    290                 295                 300

Gly His Ser Ala Val Ala Asn Ser Asp Gly Thr Val Thr Ile Val Leu
305                 310                 315                 320

Ser Arg Asp Arg Thr Pro His Pro Asn Ser Val Thr Thr Leu Gly Tyr
                325                 330                 335

Pro Arg Gly Asn Leu Ala Phe Arg Trp Phe Leu Ala Asp Gly Val Pro

```
                    340                 345                 350
Ala Arg Pro Glu Val Glu Leu Val Lys Ala Ala Asp Ala Pro Thr Ala
            355                 360                 365

Val Arg
    370

<210> SEQ ID NO 8
<211> LENGTH: 211
<212> TYPE: PRT
<213> ORGANISM: Mycobacterium avium
<220> FEATURE:
<221> NAME/KEY: MISC_FEATURE
<223> OTHER INFORMATION: Mycobacterium avium subsp. Paratuberculosis
      bovis

<400> SEQUENCE: 8

Met Trp Leu Tyr Asp Arg Pro Val Ser Leu Arg Asp Ala Val Leu Ala
1               5                   10                  15

Ala Leu Leu Glu Gly Glu Ser Ser Gly Tyr Asp Leu Ala Lys Asp Phe
            20                  25                  30

Asp Ala Ser Val Ala Asn Phe Trp Pro Ala Thr Pro Gln Gln Leu Tyr
        35                  40                  45

Arg Glu Leu Asp Arg Leu Ala Gly Gln Gly Leu Ile Arg Ala Arg Val
    50                  55                  60

Val His Gln Gln Arg Arg Pro Asn Lys Arg Met Phe Ser Leu Thr Ala
65                  70                  75                  80

Ala Gly Arg Ala Ala Ile Arg Arg Phe Thr Ala Thr Ala Pro Arg Pro
                85                  90                  95

Ser Val Ile Arg Asp Glu Leu Leu Ile Lys Val Gln Ala Ala Asp Ala
            100                 105                 110

Gly Asp Met Arg Ala Val Arg Asp Ala Ile Arg Glu Arg Arg Asp Trp
        115                 120                 125

Ala Thr Ala Lys Leu Ala Arg Tyr Gln Arg Leu Arg Ala Arg Leu Leu
    130                 135                 140

Asp Gly Arg Ser Glu Glu Asp Tyr Leu Ala Arg Ala Glu Arg Ile Gly
145                 150                 155                 160

Pro Tyr Leu Thr Leu Ile Arg Gly Ile Ser Phe Glu Glu Asp Asn Ile
                165                 170                 175

Arg Trp Ala Glu His Ala Leu Ala Val Ile Ala Arg Arg Leu Pro Thr
            180                 185                 190

Thr Asp Ala Asp Ser Asp Ala Gly Asp Ser Arg Leu Val Gly Pro Ala
        195                 200                 205

Thr Asn Gly
    210

<210> SEQ ID NO 9
<211> LENGTH: 316
<212> TYPE: PRT
<213> ORGANISM: Mycobacterium avium
<220> FEATURE:
<221> NAME/KEY: MISC_FEATURE
<223> OTHER INFORMATION: Mycobacterium avium subsp. Paratuberculosis
      bovis

<400> SEQUENCE: 9

Met Met Arg Pro Leu Ser Arg His Trp Cys Arg Val Met Gly Pro Leu
1               5                   10                  15

Ser His Ser Lys Glu Gln Leu Val Arg Val Leu Val Thr Gly Ala
            20                  25                  30
```

```
Ser Gly Gly Ile Gly Ser Ala Val Val Lys Glu Leu Leu Ala Ala Gly
        35                  40                  45

His His Val Ile Gly Leu Ala Arg Ser Glu Ala Ser Ala Ala Thr Val
 50                  55                  60

Ser Gly Leu Gly Ala Glu Pro Leu Arg Gly Asp Ile Ala Asp Leu Asp
 65                  70                  75                  80

Val Leu Gln Lys Ala Ala Val Asp Thr Asp Gly Val Ala Tyr Leu Ala
                 85                  90                  95

Phe Ser His Asp Phe Ser Asp Val Gly Asp Ala Ile Ala Asp Glu Ala
            100                 105                 110

Arg Ala Ile Asp Ala Leu Gly Ala Ala Leu Ala Asp Thr Gly Lys Pro
        115                 120                 125

Leu Val Leu Ala Ser Gly Thr Pro Ala Arg Pro Gly Val Ser Thr Glu
    130                 135                 140

Asp Pro Phe Ile Ala Asp Gly Pro Leu Ala Gly Arg Gly Arg Thr
145                 150                 155                 160

Gly Gln Ala Val Val Ala Leu Ala Gly Arg Gly Val Arg Ser Ala Val
                165                 170                 175

Val Arg Leu Pro Arg Ala Val His Asp Ala Gly Arg Tyr Gly Leu
            180                 185                 190

Val Gly Ile Leu Ile Gln Leu Ala Arg Gln Arg Gly Val Ser Ser Phe
        195                 200                 205

Ala Gly Asp Gly Thr Gln Arg Trp Pro Ala Val His Arg Asp Asp Ala
    210                 215                 220

Ala Ala Leu Phe Arg Leu Ala Leu Glu Gln Ala Pro Ala Gly Ser Val
225                 230                 235                 240

Leu His Ala Val Gly Asp Glu Gly Val Pro Leu Arg Ala Ile Ala Glu
                245                 250                 255

Val Ile Gly Arg Arg Leu Gly Val Pro Val Glu Ser Ala Pro Ala Asp
            260                 265                 270

Thr Phe Gly Pro Leu Gly Gln Val Phe Ala Val Asp Gln Pro Ser Ser
        275                 280                 285

Ser Ala Leu Thr Gln Arg Arg Phe Gly Trp Gln Pro Val Gly Pro Gly
    290                 295                 300

Leu Leu Asp Asp Leu Glu Thr Gly Val Tyr Pro Glu
305                 310                 315

<210> SEQ ID NO 10
<211> LENGTH: 288
<212> TYPE: PRT
<213> ORGANISM: Mycobacterium avium
<220> FEATURE:
<221> NAME/KEY: MISC_FEATURE
<223> OTHER INFORMATION: Mycobacterium avium subsp. Paratuberculosis
      bovis

<400> SEQUENCE: 10

Met Pro Ser Ile Glu Val Asn Gly Gly Asn Val Val Tyr Glu Ile Leu
1               5                   10                  15

Gly Asp Ser Gly Asp Leu Ile Ala Leu Thr Pro Gly Gly Arg Phe Ser
            20                  25                  30

Met Gln Ile Pro Gly Leu Arg Pro Leu Ala Asp Ala Leu Val Ala Gly
        35                  40                  45

Gly Tyr Arg Val Leu Leu Trp Asp Arg Pro Asn Cys Gly Ala Ser Asp
    50                  55                  60

Val Gln Phe Tyr Gly Gln Ser Glu Ser His Met Arg Ala Glu Thr Leu
65                  70                  75                  80
```

```
His Lys Leu Val Thr Gly Leu Gly Phe Glu Arg Cys Ile Leu Ala Gly
                85                  90                  95

Gly Ser Gly Gly Ala Arg Asp Ser Met Leu Thr Thr Met Leu Tyr Pro
            100                 105                 110

Glu Met Val Thr Lys Leu Val Val Trp Asn Ile Val Gly Gly Ile Tyr
        115                 120                 125

Gly Thr Phe Val Leu Gly Ser Phe Tyr Ile Ile Pro Ser Ile Leu Ala
    130                 135                 140

Val Arg Gly Thr Gly Met Asp Gly Val Ile Lys Val Gln Glu Trp Arg
145                 150                 155                 160

Glu Arg Ile Glu Glu Asn Pro Ala Asn Lys Gln Arg Phe Leu Asp Phe
                165                 170                 175

Asp Ser Gly Glu Phe Leu Lys Val Met Leu Arg Trp Leu Asn Ala Phe
            180                 185                 190

Val Ser Lys Pro Gly Gln Thr Ile Pro Gly Val Glu Asp Glu Met Phe
        195                 200                 205

Asp Arg Ile Thr Val Pro Thr Leu Ile Ile Arg Gly Gly Glu Asn Asp
    210                 215                 220

Met Asp His Pro Lys Arg Thr Ser Leu Glu Val Ser Cys Leu Ile Lys
225                 230                 235                 240

Gly Ser Lys Leu Ile Asp Pro Pro Trp Pro Glu Asp Ala Trp Glu Arg
                245                 250                 255

Ala Ser Glu Asp Arg Ala Ala Gly Arg Val Gln His Phe Asn Met Phe
            260                 265                 270

Asp Thr Trp Val Gln Ala Ala Pro Ala Ile Leu Glu Phe Leu Gly Ser
        275                 280                 285

<210> SEQ ID NO 11
<211> LENGTH: 97
<212> TYPE: PRT
<213> ORGANISM: Mycobacterium avium
<220> FEATURE:
<221> NAME/KEY: MISC_FEATURE
<223> OTHER INFORMATION: Mycobacterium avium subsp. Paratuberculosis
      bovis

<400> SEQUENCE: 11

Met Thr Val Thr Val Ile Leu Glu Leu Arg Phe Lys Pro Asp Glu Val
1               5                   10                  15

Ala Ala Gly Arg Glu Leu Met Gly Arg Ala Leu Gln Asp Thr Arg Ala
            20                  25                  30

Phe Asp Gly Asn Val Arg Thr Asp Val Leu Val Asp Glu Asp Asp Glu
        35                  40                  45

Ala His Trp Leu Val Tyr Glu Ile Trp Glu Thr Val Glu His Asp Gln
    50                  55                  60

Ala Tyr Arg Ala Phe Arg Ala Gly Glu Gly Lys Leu Thr Gln Leu Pro
65                  70                  75                  80

Pro Leu Leu Ala Ala Pro Pro Val Lys Thr Arg Tyr Val Thr Ser Asp
                85                  90                  95

Ile

<210> SEQ ID NO 12
<211> LENGTH: 305
<212> TYPE: PRT
<213> ORGANISM: Mycobacterium avium
<220> FEATURE:
<221> NAME/KEY: MISC_FEATURE
<223> OTHER INFORMATION: Mycobacterium avium subsp. Paratuberculosis
``` bovis

<400> SEQUENCE: 12

Met Ser Ala Gly Ile Ile Leu Met Ala His Pro Asp Ala Ala Asn Leu
1               5                   10                  15

Val Asp Asp Val Ile Ala Gln Ala Arg Arg Ala His Glu Phe Gly Val
            20                  25                  30

Gly Gln Val Trp Leu Ala Gln Gln Ser Tyr Asp Ala Ile Ala Leu
        35                  40                  45

Ala Ala Leu Val Gly Ala Ala Val Pro Gly Leu Gly Val Gly Thr Ser
    50                  55                  60

Val Val Pro Ile Asn Pro Arg His Pro Leu Ile Val Ala Ser Leu Ala
65                  70                  75                  80

Gln Thr Ala Gln Ala Ala His Gly Asn Phe Ser Leu Gly Leu Gly
                85                  90                  95

Leu Gly Ala Ala Asp Leu Glu Arg Arg Thr Phe Gly Thr Glu Trp Pro
            100                 105                 110

Asn Thr Ile Thr Arg Leu Arg Glu His Leu Thr Ile Leu Gly Ser Val
        115                 120                 125

Phe His Ser Gly Ala Val Asp Phe His Gly Ser Glu Leu Ser Ala Ala
130                 135                 140

Pro Ser Phe Pro Val Arg Val Pro Gly Gly Thr Pro Ile Pro Val Tyr
145                 150                 155                 160

Val Ala Ala Met Gly Pro Lys Ala Leu Gln Val Thr Gly Glu Leu Ala
                165                 170                 175

Asp Gly Thr Leu Pro Tyr Leu Ala Gly Pro Arg Thr Ile Glu Glu Phe
            180                 185                 190

Ile Val Pro Arg Ile Thr Lys Ala Ala Ala Glu Ala Gly Arg Pro Ala
        195                 200                 205

Pro Arg Ile Ile Ala Ala Val Pro Val Leu Leu Ser Asp Asp Val Glu
    210                 215                 220

Gly Ala Arg Ala Ala Ala Gln Gln Leu Ser Phe Tyr Glu Thr Ile
225                 230                 235                 240

Pro Ser Tyr Arg Asn Val Ile Ala Arg Glu Gly Leu Ser Asn Ala Val
                245                 250                 255

Glu Leu Ala Ala Ile Gly Pro Glu Glu Ser Val Leu Arg Gln Val Arg
            260                 265                 270

Arg Tyr Phe Asp Ala Gly Ala Thr Asp Val Val Leu Ser Pro Leu Asp
        275                 280                 285

Arg Ser Ala Ser Val Asp Arg Glu Ala Leu Trp Arg Leu Thr Ala Ala
    290                 295                 300

Leu
305

<210> SEQ ID NO 13
<211> LENGTH: 327
<212> TYPE: PRT
<213> ORGANISM: Mycobacterium avium
<220> FEATURE:
<221> NAME/KEY: MISC_FEATURE
<223> OTHER INFORMATION: Mycobacterium avium subsp. Paratuberculosis
      bovis

<400> SEQUENCE: 13

Met Thr Ser Pro Pro Leu Asp Pro Asp Ala Ala Arg Ile Ala Ser
1               5                   10                  15

Phe Gly Glu Thr Ala Pro Met Arg Gln Arg Gly Leu Pro Ala Val Arg

```
            20                  25                  30
Ala Gly Leu Glu Ser Ala Pro Arg Pro Ala Thr Met Pro Glu Met Ala
        35                  40                  45
Ser Val Thr Glu Ala Leu Val Pro Ser Ala Ala Gly Gly Ile Pro Val
    50                  55                  60
Arg Ile Tyr Arg Pro Thr Thr Asp Ser Gly Val Ala Val Leu Val Tyr
65                  70                  75                  80
Leu His Gly Gly Gly Leu Val Met Gly Ser Asn Arg Ser Phe Glu Pro
                85                  90                  95
Leu Ala Arg Glu Leu Ala Ser Ala Ala Thr Val Val Ala Val
            100                 105                 110
Asp Tyr Arg Leu Ala Pro Glu Ser Pro Pro Ala Gln Phe Asp Asp
        115                 120                 125
Ala Tyr Ala Ala Thr Glu Trp Val Ser Arg Lys Ala Gly Glu Leu Gly
    130                 135                 140
Val Asp Ala Asp Arg Leu Ala Val Ile Gly Asp Ser Ala Gly Gly Ser
145                 150                 155                 160
Leu Ala Ala Ala Val Ala Leu Ala Ala Arg Asp Arg Arg Gly Pro Pro
                165                 170                 175
Ile Cys Ala Gln Val Leu Leu Tyr Pro Gly Leu Asp Arg Asp Met Ser
            180                 185                 190
Val Ala Ser Ile Ala Ala Met Pro Asp Ala Pro Leu Leu Ile Arg Asp
        195                 200                 205
Asp Ile Asp Tyr Met His Ala Leu Val Asp Gly Asp Ala Gly Pro Pro
    210                 215                 220
Thr Asp Pro Tyr Leu Val Pro Ala Tyr Ala Ala Asp Leu Ser Gly Leu
225                 230                 235                 240
Pro Pro Ala Ile Val Val Thr Ala Gly Cys Asp Pro Ile Arg Asp Trp
                245                 250                 255
Gly Glu Arg Tyr Ala Asp Arg Leu Arg Asp Ala Gly Val Gln Thr Thr
            260                 265                 270
Val Thr Arg Tyr Pro Gly Met Tyr His Gly Phe Leu Met Arg Ser Asp
        275                 280                 285
Ala Thr Ala Arg Gly Arg Leu Ala Ile Ala Glu Ile Gly Gly Leu Leu
    290                 295                 300
Arg Ala Lys Phe Ser His Pro Leu Arg Phe Asp Val Pro Ile Thr Gly
305                 310                 315                 320
Arg His Ser Thr Ala Thr Arg
                325

<210> SEQ ID NO 14
<211> LENGTH: 127
<212> TYPE: PRT
<213> ORGANISM: Mycobacterium avium
<220> FEATURE:
<221> NAME/KEY: MISC_FEATURE
<223> OTHER INFORMATION: Mycobacterium avium subsp. Paratuberculosis
      bovis

<400> SEQUENCE: 14

Met Thr Lys Arg Ala Ser Ala Ala Ala Ile Ala Val Gly Val Ala Phe
1               5                   10                  15
Ala Pro Thr Ala Val Ala His Ala Asp Asn Asn Gly Ile Ala Met Ala
            20                  25                  30
Ile Ser Asp Ser Thr Gly His Ile Ser Ile Ala Asp Gly Ala Ala Ser
        35                  40                  45
```

```
Gln Gly Ala Ala Glu Lys Ala Met Asp Thr Cys Arg Lys Ser Ile
         50                  55                  60
Ser Asp Cys Arg Leu Leu Ala Ser Gly Gln Gly Gly Cys Met Ala Leu
 65                  70                  75                  80
Val Leu Asn Ala Ser Lys Ser Lys Tyr Phe Gly Ala Trp Gly Pro Thr
                 85                  90                  95
Arg Glu Glu Ala Glu Ala Ala Leu Ala Arg Val Pro Gly Gly Thr
             100                 105                 110
Val Gln Glu Gly His Asp His Cys Ala Gly Glu Gly Ser Pro Gln
             115                 120                 125
```

<210> SEQ ID NO 15
<211> LENGTH: 142
<212> TYPE: PRT
<213> ORGANISM: Mycobacterium avium
<220> FEATURE:
<221> NAME/KEY: MISC_FEATURE
<223> OTHER INFORMATION: Mycobacterium avium subsp. Paratuberculosis bovis

<400> SEQUENCE: 15

```
Met Lys Pro Phe Ser Glu Ser Glu Arg Gln Glu Phe Leu Ala Gly Thr
  1               5                  10                  15
His Val Ala Val Leu Ser Val Glu Ala Thr Asp Gly Arg Pro Pro Ala
                 20                  25                  30
Ala Val Pro Ile Trp Tyr Asp Tyr Thr Pro Gly Gly Asp Ile Arg Ile
                 35                  40                  45
Met Thr Gly Ala Ser Ser Arg Lys Ala Arg Leu Ile Glu Arg Ala Gly
         50                  55                  60
Lys Val Thr Val Val Gln Arg Glu Glu Pro Pro Tyr Gln Tyr Val
 65                  70                  75                  80
Val Val Glu Gly Thr Val Val Asp Ala Thr Lys Pro Ala Pro Ser Asp
                 85                  90                  95
Val Gln Leu Ala Val Ala Ile Arg Tyr Leu Gly Glu Asp Gly Gly Arg
                100                 105                 110
Ala Phe Val Gln Ser Leu Glu Gly Val Glu Glu Val Leu Phe Thr Ile
                115                 120                 125
Arg Pro Asp Arg Trp Leu Ser Ala Asp Phe Thr Gly Asp Leu
            130                 135                 140
```

<210> SEQ ID NO 16
<211> LENGTH: 172
<212> TYPE: PRT
<213> ORGANISM: Mycobacterium avium
<220> FEATURE:
<221> NAME/KEY: MISC_FEATURE
<223> OTHER INFORMATION: Mycobacterium avium subsp. Paratuberculosis bovis

<400> SEQUENCE: 16

```
Met Ala Val Val Trp Ala Gly Ala Ala Pro Gly Ala Pro Arg Val
  1               5                  10                  15
Ala Leu Val Ser Gly Glu Ala Ile Ala Ile Ala Gln Gly Val Ser Val
                 20                  25                  30
Thr Pro Ala Pro Gly Trp Thr Leu Gly Asn Arg Gly Pro Asn Trp Val
                 35                  40                  45
Ala Leu Asn Asn Ser Asp Thr Thr Ala Gln Leu Arg Ile Thr Val Lys
         50                  55                  60
Pro Gly Ala Gly Thr Asp Ala Ala Leu Leu Gln Ala Asp Val Asp
 65                  70                  75                  80
```

```
Gln Tyr Thr Gly Gly Ala Ser Ala Ile Leu Thr Asp Val Asn Arg Leu
                85                  90                  95

Gly Pro Pro Glu Thr Thr Pro Leu Gln Gly Pro Asn Phe Gln Gln Gln
            100                 105                 110

Ala Ser Leu Asn Tyr Thr Ala Thr Val Val His Pro Gln Gly Ser Ile
        115                 120                 125

Pro Val Ile Gly Thr Phe Thr Glu Leu Leu Asn Thr Ser Thr Gly Arg
    130                 135                 140

Ser Ala Phe Val Asp Phe Arg Gln Asp Ser Ser Ala Thr Thr Gln Ala
145                 150                 155                 160

Ala Gly Glu Gly Ala Ala Met Ile Ala Ser Leu Gln
                165                 170

<210> SEQ ID NO 17
<211> LENGTH: 185
<212> TYPE: PRT
<213> ORGANISM: Mycobacterium avium
<220> FEATURE:
<221> NAME/KEY: MISC_FEATURE
<223> OTHER INFORMATION: Mycobacterium avium subsp. Paratuberculosis
      bovis

<400> SEQUENCE: 17

Met Arg Tyr Leu Gln Pro Val Thr Arg Pro Ala Arg Met Ser Thr Leu
1               5                   10                  15

Ala Ala Ala Leu Ala Leu Thr Ala Cys Leu Thr Ala Pro Gly Ala Thr
            20                  25                  30

Ala Asp Pro Thr Pro Gln Gln Ser Pro Phe Pro Thr Gly Lys Ser Gly
        35                  40                  45

Thr Thr Ile His Val Thr Glu Tyr Ser Thr Ala Thr Ala Asp Val Thr
    50                  55                  60

Leu Asn Ser Ala Thr Trp Val Ser Ser Gly Cys Pro Gly Gly Gly Gly
65                  70                  75                  80

Cys Asn Val Ile Glu Leu Thr Ile Ala Gly Lys Ser Asp Lys Pro Phe
                85                  90                  95

Thr Tyr Ser Gln Ala Ser Ile Thr Ala Ala Ser Thr Pro Trp Arg Gln
            100                 105                 110

Asp Pro Tyr Arg Asp Thr Gln Gly Gly Ser Ser Leu Ala Asp Tyr Gln
        115                 120                 125

Gln Leu Asn Lys Thr Pro Pro Leu Arg Val Gly Ser Val Thr Asn Gly
    130                 135                 140

Gln Thr Ala His Gly Phe Ile Ala Tyr Asp Gly Ala Ile Arg Gln Gly
145                 150                 155                 160

Asp Val Tyr Ile Glu Phe Asn Asp Pro Asp Ala Pro Ala Pro Thr
                165                 170                 175

Pro Leu Ala Gly Trp Lys Val His Thr
            180                 185

<210> SEQ ID NO 18
<211> LENGTH: 873
<212> TYPE: PRT
<213> ORGANISM: Mycobacterium avium
<220> FEATURE:
<221> NAME/KEY: MISC_FEATURE
<223> OTHER INFORMATION: Mycobacterium avium subsp. Paratuberculosis
      bovis

<400> SEQUENCE: 18

Met Ile Lys Lys Met Gly Tyr Arg Trp Arg Leu Arg Asp Leu Met Ala
```

-continued

```
1               5               10              15

Asp Gln Gln Met Phe Lys Thr Thr Asp Leu Ile Pro His Leu Val Glu
            20                  25              30

Arg Gly Ile Thr Leu Ser Arg Glu Gln Val Phe Arg Leu Val Thr Gln
            35              40              45

Pro Pro Gln Arg Leu Ser Met Asp Thr Leu Val Ala Leu Cys Asp Ile
50              55              60

Leu Gly Cys Thr Pro Asn Asp Leu Ile Val Leu Glu Val Val Asn Lys
65              70              75              80

Pro Val Arg Lys Thr Ala Gly Ala Gly Gly Glu Trp Cys Ala Gly Gly
                85              90              95

His Ala Gln Lys Asn Ser Arg Thr Thr Ala Trp Gln Val Met Thr Arg
            100             105             110

Pro His Ser Thr Ala Pro Ile Ala His Val Arg Glu Ser Leu Val Ser
            115             120             125

Ser Val Ile Ser Ala Val Gly Ser Gly Met Thr Arg Gln Arg Ala Gln
            130             135             140

Gln Leu Leu Val Glu Ala Lys Gly Trp Ser Thr Ala Asn Ala Arg His
145             150             155             160

Leu His Glu Tyr Leu Gly Glu Asn Pro Gly Ala Phe Thr Ala Pro Thr
                165             170             175

His Glu Cys Pro Ala Ala Phe Pro Arg Leu Leu Thr Leu Leu Ala Ala
            180             185             190

Ala Gly His Ala Asp Ala Val Ser Leu Leu Gly Cys Ala Lys Cys Gly
            195             200             205

Arg Thr Asp Leu Ala Leu Arg Arg Asn Ser Pro Glu Gly Arg Cys Cys
210             215             220

Pro Trp Cys Val Ile Arg Thr Glu Leu Arg Pro Cys Ala Arg Cys Gly
225             230             235             240

Glu Asp Gly Tyr Ile Ile Ala Arg Arg Ala Asp Gly Pro Val Cys Arg
                245             250             255

Arg Cys Tyr Asn Lys Asp Pro Gln Phe Leu Gln Val Cys Ala Gly Cys
            260             265             270

Gly Arg Lys Arg Pro Pro Asn Ala Arg Arg Asp Asp Gly Thr Val Leu
            275             280             285

Cys Gln Arg Cys Ser Leu Pro Pro Thr Gln Ser Cys Arg Cys Gly
            290             295             300

Asn Val Arg Arg Val His Ala Gln Thr Ala Asp Gly Pro Ile Cys Arg
305             310             315             320

Thr Cys Tyr Arg Ser Pro Ala Arg Lys Cys Gly Val Cys Gly Glu Ile
                325             330             335

Ala Gln Ile Gln Ala Arg Ala Thr Asp Thr His Pro Asp Thr Cys Val
            340             345             350

Arg Cys Tyr Arg Asn Ile Gly Glu Cys Val Val Cys Gly Arg Thr Arg
            355             360             365

Ala Gly Gly Lys Tyr Arg Gly Gly Ser Leu His Cys Val Thr Cys Trp
            370             375             380

Pro His His Pro Arg His Cys Asp Ser Cys Glu Lys Pro Gly Ile Ala
385             390             395             400

Cys Ala Thr Trp Pro Leu Gly Thr Val Cys Arg Asp Cys Tyr His Arg
                405             410             415

Arg Arg Leu His Pro Gln Pro Cys Ala Asn Cys His Arg Thr Ala Val
            420             425             430
```

```
Met Val Gly Arg Asn Pro Asp Gly Gln Asp Ile Cys Ala Pro Cys Cys
        435                 440                 445

Gly Val Asp Leu Asp Phe Ser Cys Arg Thr Cys Gly Ile Glu Gly Leu
        450                 455                 460

Asn Tyr Ala Asp Gly Lys Cys Thr Cys Cys Val Met Thr Asp Arg Val
465                 470                 475                 480

Asn Val Leu Leu Ser Leu Asp Asp Gly Thr Val Val Pro Gln Leu Gln
                485                 490                 495

Pro Leu Ala Asp Ala Leu Ser Ala Ala Asn Pro Glu Ser Val Gln Thr
                500                 505                 510

Trp Leu Gln Ala Ser Ser Ala Arg Leu Leu Ala Gln Leu Val Ala
        515                 520                 525

Glu Arg Arg Ala Ile Ser His Glu Leu Leu Asp Glu Leu Asp Gln Asp
        530                 535                 540

Asn Ala Thr Arg Tyr Ile Arg Gln Leu Leu Val Thr Gly Ile Leu
545                 550                 555                 560

Thr Ser Arg Gln Glu Glu Phe Ala Gln Leu Gln Ile Trp Ala Ser Arg
                565                 570                 575

Lys Ile Gln His Leu Pro Pro His Gln Ser Arg Val Val Arg Pro Phe
                580                 585                 590

Ala Glu Trp Arg Val Ile Arg Asp Ala Arg Lys Arg Ala Ala Arg Arg
        595                 600                 605

Arg Tyr Thr Ile Gly Ser Ala Ala Asn Asp Arg Gln Lys Ile Ser Thr
        610                 615                 620

Thr Ile Ala Phe Leu Thr Trp Leu Asp Asp Gln Glu Ile Pro Leu Asp
625                 630                 635                 640

Ser Val Thr Gln Leu His Leu Asp Arg Trp Leu Asp Ala His Pro Thr
                645                 650                 655

Lys His Lys Tyr Ala Ala Phe Ile Gly Trp Leu Glu Lys Gln Arg Leu
                660                 665                 670

Thr Gln Ala Glu Leu Val Val Pro Gln Arg Arg Ser Gln Leu Pro Ser
        675                 680                 685

Arg Leu Leu Ser Asp Asp Glu Leu Glu Gln Gln Leu Lys Arg Cys Leu
        690                 695                 700

Thr Asp Asp Thr Leu Pro Leu Asp Val Arg Val Val Gly Ala Leu Ile
705                 710                 715                 720

Arg Leu Tyr Ala Pro Pro Leu Val Arg Ile Ala Glu Leu Thr Thr Asp
                725                 730                 735

Arg Tyr His Thr Asp Asp Asp Gly Ser Tyr Leu Thr Ile Gly Arg His
                740                 745                 750

Pro Val Leu Leu Pro Pro Thr Leu Ala Arg Leu Ile Glu Gln Leu Ile
        755                 760                 765

Ala Arg Gly Pro Val Asn Thr Leu Leu Arg Asn Gly Ser Ala Asp Asn
        770                 775                 780

Pro Ala Tyr Leu Leu Ala Gly Arg Pro Pro Ser Arg Pro Val Asn Pro
785                 790                 795                 800

Arg Ser Leu Gln Gln Arg Leu Thr Lys His Gly Leu Pro Val Ile His
                805                 810                 815

Ala Arg Asn Thr Ala Met Ile Thr Asn Ala Ala Thr Leu Pro Pro Pro
        820                 825                 830

Val Val Ala Glu Leu Phe Gly Ile His Pro Thr Thr Ala Tyr Gln Trp
        835                 840                 845

Ala Gln Tyr Ala Gln Ser Ser Trp Ala Ala Tyr Leu Gln Ala Cys Gln
        850                 855                 860
```

Ser Thr Ala Gln Pro Gly Leu Arg Cys
865                 870

<210> SEQ ID NO 19
<211> LENGTH: 304
<212> TYPE: PRT
<213> ORGANISM: Mycobacterium avium
<220> FEATURE:
<221> NAME/KEY: MISC_FEATURE
<223> OTHER INFORMATION: Mycobacterium avium subsp. Paratuberculosis
      bovis

<400> SEQUENCE: 19

Met Ala Arg Thr Asp Asp Thr Trp Asp Leu Ala Thr Ser Val Gly
1               5                   10                  15

Ala Thr Ala Thr Met Val Ala Ala Gly Arg Ala Arg Ala Thr Arg Asp
            20                  25                  30

Gly Leu Ile Asp Asp Pro Phe Ala Glu Pro Leu Val Arg Ala Val Gly
                35                  40                  45

Val Asp Phe Phe Thr Arg Trp Ala Ala Gly Glu Leu Asp Ala Ala Asp
50                  55                  60

Val Asp Val Pro Gly Ala Ala Trp Gly Met Gln Arg Met Thr Asp Met
65                  70                  75                  80

Leu Thr Ala Arg Thr Arg Tyr Ile Asp Ala Phe Phe Ala Glu Ala Gly
                85                  90                  95

Ala Ala Gly Ile Arg Gln Val Val Ile Leu Ala Ser Gly Leu Asp Ala
            100                 105                 110

Arg Ala Tyr Arg Leu Pro Trp Pro Ala Gly Thr Thr Val Phe Glu Ile
        115                 120                 125

Asp Gln Pro Arg Val Leu Glu Phe Lys Ala Ala Thr Ile Ala Gln Leu
    130                 135                 140

Gly Ala Glu Pro Thr Ala Pro Val Arg Ala Val Ala Val Asp Leu Arg
145                 150                 155                 160

His Asp Trp Pro Ser Ala Leu Arg Gln Ala Gly Phe Asp Val Gly Arg
                165                 170                 175

Pro Ala Ala Trp Ala Ala Glu Gly Leu Leu Gly Phe Leu Pro Pro Gln
            180                 185                 190

Ala Gln Asp Arg Leu Leu Asp Asn Val Thr Ala Leu Ser Ala Asp Gly
        195                 200                 205

Ser Gln Leu Val Ala Glu Val Phe Ala Asn Thr Gly Ala Ser Gly Asp
    210                 215                 220

Ala Leu Asn Ala Ala Gly Glu Lys Trp Arg Arg His Gly Leu Asp Val
225                 230                 235                 240

Ala Leu Asp Asp Leu Gly Phe Pro Gly Glu Arg Asn Asp Pro Ala Ser
                245                 250                 255

Tyr Leu Gln Gln Leu Gly Trp Gln Pro Val Arg Thr Pro Leu Asn Gln
            260                 265                 270

Met Leu Ala Asn Asn Gly Leu Pro Leu Gln Ser Thr Glu Pro Gly Ala
        275                 280                 285

Pro Phe Ala Gln Asn Tyr Tyr Cys Thr Ala Val Leu Asn Lys Ala Gly
    290                 295                 300

<210> SEQ ID NO 20
<211> LENGTH: 392
<212> TYPE: PRT
<213> ORGANISM: Mycobacterium avium
<220> FEATURE:
<221> NAME/KEY: MISC_FEATURE
<223> OTHER INFORMATION: Mycobacterium avium subsp. Paratuberculosis bovis

<400> SEQUENCE: 20

```
Met Ala Phe Ala Glu Tyr Gln Asn Glu Leu Tyr Asp Gln Ser Leu His
1               5                   10                  15

Gly Asn Gln Pro Gln Tyr Pro Ile Arg Phe Glu Glu Leu Glu Ala Lys
            20                  25                  30

Ala Ser Ala Ala Met Thr Pro Lys Val Leu Gly Tyr Val Ala Gly Gly
        35                  40                  45

Ala Gly Asp Glu His Thr Gln Arg Ala Asn Cys Glu Ala Phe Lys Arg
    50                  55                  60

Trp Gly Leu Tyr Pro Arg Met Gly Ile Ala Pro Glu Gln Arg Asp Met
65                  70                  75                  80

Ser Val Glu Leu Phe Gly Thr Arg Phe Pro Ser Pro Ile Phe Met Ala
                85                  90                  95

Pro Ile Gly Val Ile Gly Val Cys Asp Pro Asp Gly His Gly Asp Leu
            100                 105                 110

Ala Cys Val Arg Ala Ser Ile Arg Thr Gly Val Pro Phe Phe Val Gly
        115                 120                 125

Thr Leu Ser Ala Asp Pro Met Glu Asp Leu Ala Asp Glu Leu Gly Asp
130                 135                 140

Thr Pro Ala Phe Phe Gln Leu Tyr Thr Pro Pro Asp Arg Lys Met Ala
145                 150                 155                 160

Ala Ser Leu Val His Arg Ala Glu Ala Ala Ser Phe Ser Gly Ile Ala
                165                 170                 175

Val Thr Leu Asp Thr Trp Val Thr Gly Trp Arg Pro Arg Asp Leu Ser
            180                 185                 190

Gly Gly Asn Tyr Pro Gln Val Pro Ser Gly Cys Leu Ala Asn Tyr Thr
        195                 200                 205

Ser Asp Pro Val Phe Arg Ala Gly Leu Ser Arg Gly Glu Asp Pro Thr
    210                 215                 220

Glu Ala Ala Val Arg Lys Leu Pro Ile Phe Gly Gly Pro Phe Arg Trp
225                 230                 235                 240

Glu Asp Leu Glu Trp Leu Arg Ser Arg Thr Ser Leu Pro Leu Met Ala
                245                 250                 255

Lys Gly Ile Cys His Pro Asp Asp Val Arg Arg Ala Lys Asp Ile Gly
            260                 265                 270

Val Asp Ala Val Tyr Cys Ser Asn His Gly Gly Arg Gln Ala Asn Gly
        275                 280                 285

Gly Leu Pro Cys Leu Asp Cys Leu Pro Gly Val Val Glu Ala Ala Asp
    290                 295                 300

Gly Leu Pro Val Leu Phe Asp Ser Gly Val Arg Ser Gly Ala Asp Ile
305                 310                 315                 320

Val Lys Ala Leu Ala Leu Gly Ala Thr Ala Val Gly Ile Gly Arg Pro
                325                 330                 335

Tyr Ala Tyr Gly Leu Ala Leu Gly Gly Val Asp Gly Ile Val His Val
            340                 345                 350

Leu Arg Ser Leu Leu Ala Glu Ala Asp Leu Ile Met Ala Val Asp Gly
        355                 360                 365

Tyr Pro Ser Leu Lys Asp Leu Thr Pro Asp Ala Leu Arg Arg Val Glu
    370                 375                 380

His Val Ala Pro Gln Arg Tyr Ser
385                 390
```

<210> SEQ ID NO 21
<211> LENGTH: 389
<212> TYPE: PRT
<213> ORGANISM: Mycobacterium avium
<220> FEATURE:
<221> NAME/KEY: MISC_FEATURE
<223> OTHER INFORMATION: Mycobacterium avium subsp. Paratuberculosis bovis

<400> SEQUENCE: 21

Met Glu Glu Pro Val Ala Lys Cys Val Met Val Leu Tyr Pro Asp
1               5                   10                  15

Pro Val Asp Gly Tyr Pro Pro Lys Tyr Ala Arg Asp Ser Ile Pro Val
                20                  25                  30

Ile Asn Ser Tyr Pro Asp Gly Ser Ser Leu Pro Thr Pro Ser Lys Ile
        35                  40                  45

Asp Phe Thr Pro Gly Glu Leu Leu Gly Cys Val Ser Gly Ala Leu Gly
    50                  55                  60

Leu Arg Lys Phe Phe Glu Asp Gly Gly His Glu Leu Val Val Thr Ser
65                  70                  75                  80

Asp Lys Asp Gly Pro Asp Ser Glu Phe Glu Arg Glu Leu Pro Asp Ala
                85                  90                  95

Asp Ile Val Ile Ser Gln Pro Phe Trp Pro Ala Tyr Ile Thr Lys Glu
            100                 105                 110

Arg Phe Ala Lys Ala Arg Asn Leu Lys Leu Ala Leu Thr Ala Gly Ile
        115                 120                 125

Gly Ser Asp His Val Asp Leu Ala Glu Ala Gln Ala Arg Gly Val Thr
    130                 135                 140

Val Ala Glu Glu Thr Trp Ser Asn Ser Ile Ser Val Ala Glu His Thr
145                 150                 155                 160

Val Met Gln Ile Leu Ala Leu Val Arg Asn Phe Val Pro Ser His Gln
                165                 170                 175

Trp Ile Arg Asp Gly Gly Trp Asn Ile Ala Asp Cys Val Gln Arg Ser
            180                 185                 190

Tyr Asp Val Glu Gly Met Asp Val Gly Val Ile Ala Ala Gly Arg Ile
        195                 200                 205

Gly Arg Ala Val Leu Glu Arg Met Lys Pro Phe Gly Val Asn Leu His
    210                 215                 220

Tyr Phe Asp Val His Arg Leu Ser Pro Glu Tyr Glu Lys Gln Leu Gly
225                 230                 235                 240

Val Thr Tyr His Pro Asp Val Glu Ser Leu Ala Arg Ser Val Asp Val
                245                 250                 255

Val Ser Ile His Ser Pro Leu Ile Ala Gln Thr His His Met Phe Asn
            260                 265                 270

Glu Lys Leu Leu Lys Ser Met Arg Arg Gly Ser Tyr Ile Val Asn Thr
        275                 280                 285

Ala Arg Ala Glu Glu Thr Asp His Lys Ala Ile Val Ala Ala Leu Glu
    290                 295                 300

Ser Gly Gln Leu Ala Gly Tyr Ala Gly Asp Val Trp Phe Pro Gln Pro
305                 310                 315                 320

Pro Pro Pro Asp His Pro Trp Arg Thr Met Pro Asn His Ala Met Thr
                325                 330                 335

Pro His Ile Ser Gly Ser Ser Leu Ser Ala Gln Ala Arg Tyr Cys Ala
            340                 345                 350

Gly Thr Arg Glu Ile Leu Glu Asp Trp Phe Ala Gly Arg Pro Ile Arg
        355                 360                 365

-continued

Ser Glu Tyr Leu Ile Val Glu Gly Gly Lys Phe Ala Gly Thr Gly Ala
    370                 375                 380

Lys Ser Tyr Ala Gln
385

<210> SEQ ID NO 22
<211> LENGTH: 500
<212> TYPE: PRT
<213> ORGANISM: Mycobacterium avium
<220> FEATURE:
<221> NAME/KEY: MISC_FEATURE
<223> OTHER INFORMATION: Mycobacterium avium subsp. Paratuberculosis
      bovis

<400> SEQUENCE: 22

Met Ile Arg Ile Asp Gly Val Arg Trp Gln Tyr Ala Gly Thr Asp Ala
1               5                   10                  15

Ala Val Leu Asp Gly Val Asp Leu His Ile Arg Arg Gly Glu Thr Val
                20                  25                  30

Leu Leu Cys Gly Ala Ser Gly Ser Gly Lys Ser Ser Val Leu Arg Leu
            35                  40                  45

Met Asn Gly Leu Ile Pro His Phe His Gln Gly Ser Leu Asp Gly Ser
        50                  55                  60

Val His Ile Asp Gly Thr Ser Val Ala Glu Leu Ser Leu Glu Arg Val
65                  70                  75                  80

Gly Arg Leu Thr Gly Thr Val Leu Gln His Pro Arg Arg Gln Phe Phe
                85                  90                  95

Thr Ala Ala Val Asp Thr Glu Leu Ala Phe Thr Leu Glu Asn Phe Gly
            100                 105                 110

Thr Pro Pro Glu Gln Ile Arg Asn Arg Val Gly Ser Val Ile Thr Glu
        115                 120                 125

Tyr Gly Leu Ala Glu Leu Thr Gly His Arg Leu Ala Glu Leu Ser Gly
    130                 135                 140

Gly Gln Gln Gln Gln Ile Ala Cys Ala Ala Ala Thr His Gly Pro
145                 150                 155                 160

Pro Leu Leu Leu Phe Asp Glu Pro Thr Ala Asn Leu Ala Ala Asp Ala
                165                 170                 175

Ile Glu Arg Phe Thr Ala Thr Leu Ala Arg Leu Arg Ser Leu Gly Thr
            180                 185                 190

Thr Ile Val Ile Ala Glu His Arg Leu His Tyr Leu Arg Glu Ile Ala
        195                 200                 205

Asp Arg Ile Val Leu Leu Arg Asn Gly Arg Ile Ala Ala Glu Trp Ser
    210                 215                 220

Arg Lys Gln Phe Ala Arg Leu Asp Asp Ala Ala Leu Asn Ala Glu Gly
225                 230                 235                 240

Leu Arg Ser Asn Asn Ser Pro Val Arg Asn His Ile Pro Pro Ala Cys
                245                 250                 255

Ala Tyr Gly Ala Ser Val Ala Gly Thr Pro Ser Gly Thr Ala Ala Pro
            260                 265                 270

Ala Ser Ser Pro Ser Glu Val Val Leu Arg Gly Ile Arg Cys Cys Phe
        275                 280                 285

Arg Gly His Arg Val Leu Asp Ile Glu Glu Ala Arg Phe Pro Ala Ala
    290                 295                 300

Thr Val Thr Ala Ile Thr Gly Pro Asn Gly Ala Gly Lys Ser Thr Leu
305                 310                 315                 320

Ala Arg Val Leu Val Gly Leu Gln Arg His Asp Gly Glu Val Ser Phe

```
                    325                 330                 335
Gly Gly Ser Arg Ile Ser Arg Ser Arg Gln Arg Met Ser Ala Ile
                340                 345                 350
Val Met Gln Asp Val Gln Arg Gln Leu Phe Thr Glu Ser Val Arg Ala
                355                 360                 365
Glu Leu Arg Leu Gly Ala Pro Pro Ala Ala Gly Val Ala Ser Thr
                370                 375                 380
Leu Leu Arg Asp Leu Gly Leu Glu Glu Phe Ala Asp Arg His Pro Leu
385                 390                 395                 400
Ser Leu Ser Gly Gly Gln Gln Gln Arg Leu Val Val Ala Ala Arg
                405                 410                 415
Leu Ser Asn Arg Lys Ile Met Val Phe Asp Glu Pro Ser Ser Gly Val
                420                 425                 430
Asp Arg Arg His Leu Arg Ser Ile Thr Asn Val Met Arg Asp Val Ala
                435                 440                 445
Ala Gln Gly Val Val Val Ile Leu Ile Ser His Asp Gln Glu Leu Leu
                450                 455                 460
Thr Leu Ala Ala Asp Gln Glu Leu Arg Met Arg Val Ala Asp Thr Leu
465                 470                 475                 480
Asn Ala Arg Ser Arg Arg Lys Ala Ala Gly Glu Asn Ala Cys Leu Glu
                485                 490                 495
Thr Leu Ser Asp
            500

<210> SEQ ID NO 23
<211> LENGTH: 273
<212> TYPE: PRT
<213> ORGANISM: Mycobacterium avium
<220> FEATURE:
<221> NAME/KEY: MISC_FEATURE
<223> OTHER INFORMATION: Mycobacterium avium subsp. Paratuberculosis
      bovis

<400> SEQUENCE: 23

Met Asp Arg Arg Ser Met Met Leu Met Ser Gly Ile Gly Met Leu Gly
1               5                   10                  15
Ala Ala Met Arg Leu Pro Gly Ala Trp Ala Thr Pro Ala Pro Glu
                20                  25                  30
Ala Pro Pro Ser Ala Gly Gly Pro Tyr Ile Phe Ala Asp Glu Phe
                35                  40                  45
Asp Gly Pro Ala Gly Ser Pro Pro Asp Pro Gly Lys Trp Thr Ile Gln
50                  55                  60
Thr Trp Gln Asp Asp Val Phe Pro Pro Val Ala Gly Ile Tyr Arg Asp
65                  70                  75                  80
Asp Arg Arg Asn Val Phe Gln Asp Gly Asn Ser Asn Leu Val Leu Cys
                85                  90                  95
Ala Thr Gln Glu Met Gly Thr Tyr Tyr Ser Gly Lys Leu Arg Gly Asn
                100                 105                 110
Phe Arg Ser Met Ile Asn Gln Thr Trp Glu Ala Arg Ile Lys Leu Asp
                115                 120                 125
Cys Leu Phe Pro Gly Leu Trp Pro Ser Phe Trp Gly Val Asn Glu Asp
                130                 135                 140
Pro Leu Pro Asp Gly Glu Val Asp Ile Phe Glu Trp Tyr Gly Asn Gly
145                 150                 155                 160
Gln Trp Pro Pro Gly Thr Thr Val His Ala Ala Ser Asn Gly Lys Thr
                165                 170                 175
```

Trp Glu Gly Lys Ser Ile Pro Gly Leu Val Asp Gly Asn Trp His Thr
            180                 185                 190

Trp Arg Met His Trp Gly Glu Gly Phe Glu Phe Ser Arg Asp Gly
            195                 200                 205

Ala Glu Tyr Phe Lys Val Pro Asn Lys Pro Ile His Val Ala Gly Gly
210                 215                 220

Ala Pro Asp Asp Phe Arg Trp Pro Phe Asn Asn Pro Gly Tyr Trp Met
225                 230                 235                 240

Thr Pro Met Phe Thr Leu Ala Val Gly Gly Val Gly Ala Gly Asp Pro
                245                 250                 255

Ala Ala Gly Val Phe Pro Ser Ser Met Leu Ile Asp Tyr Ile Arg Ile
                260                 265                 270

Trp

<210> SEQ ID NO 24
<211> LENGTH: 130
<212> TYPE: PRT
<213> ORGANISM: Mycobacterium avium
<220> FEATURE:
<221> NAME/KEY: MISC_FEATURE
<223> OTHER INFORMATION: Mycobacterium avium subsp. Paratuberculosis
      bovis

<400> SEQUENCE: 24

Met Leu Ala Thr Ile Gly Ala Ala Val Ala Ala Phe Ala Leu Ala
1               5                   10                  15

Ala Pro Ala Gln Leu Ser Ala Pro Ala Gln Ala Asp Pro Pro Thr
            20                  25                  30

Ala Pro Tyr Pro Thr Pro Arg Thr Pro Ser Pro Pro Ser Asp Tyr Asp
            35                  40                  45

Ala Pro Phe Lys Asn Thr Val Asn Gly Phe Gly Ile Tyr Gln Pro Gln
50                  55                  60

Asp Gln Leu Ala Trp Leu Gly Lys Ile Thr Cys Asp Arg Leu Asp His
65                  70                  75                  80

Gly Val Asp His Asp Ala His Gln Ser Ala Thr Phe Ile Gln Arg Asn
                85                  90                  95

Leu Pro Arg Gly Thr Ser Glu Gly Gln Ser Leu Gln Phe Leu Gly Ala
            100                 105                 110

Ala Val Asp His Tyr Cys Pro Glu His Ile Asp Val Val Gln Ala Ala
            115                 120                 125

Gly Arg
    130

<210> SEQ ID NO 25
<211> LENGTH: 171
<212> TYPE: PRT
<213> ORGANISM: Mycobacterium avium
<220> FEATURE:
<221> NAME/KEY: MISC_FEATURE
<223> OTHER INFORMATION: Mycobacterium avium subsp. Paratuberculosis
      bovis

<400> SEQUENCE: 25

Met Glu Ala Trp Asp Ala Ile Cys Ala Arg Arg Asn Val Arg Glu Tyr
1               5                   10                  15

Gln Pro Arg Ala Ile Ala Gly Glu Asp Leu Asp Arg Ile Val Glu Ala
            20                  25                  30

Gly Trp Arg Ala Pro Ser Ala Lys Asn Arg Gln Pro Trp Asp Phe Val
            35                  40                  45

```
Ile Val Thr Asp Arg Thr Gln Leu Gln Glu Leu Ser Thr Val Trp Arg
 50                  55                  60

Gly Ala Gly His Ile Ala Gly Ala Pro Ala Ala Ile Ala Ile Val Val
 65                  70                  75                  80

Pro Glu Pro Pro Asp Glu Arg Arg Val Val Thr Asp Asn Tyr Asp Val
                 85                  90                  95

Gly Gln Ala Thr Met Ala Met Met Ile Ala Thr Asp Leu Gly Ile
                100                 105                 110

Gly Thr Gly His Ser Ser Val Gly Asp Gln Asp Lys Ala Arg Ala Ile
                115                 120                 125

Leu Gly Val Pro Asp Gly His Leu Val Ala Phe Leu Leu Gly Val Gly
    130                 135                 140

Tyr Pro Ala Asp Arg Pro Leu Thr Pro Ile Arg Lys Pro Asn Arg Arg
145                 150                 155                 160

Pro Phe Thr Glu Val Val His Arg Gly Arg Trp
                165                 170

<210> SEQ ID NO 26
<211> LENGTH: 28
<212> TYPE: DNA
<213> ORGANISM: Artificial Sequence
<220> FEATURE:
<223> OTHER INFORMATION: Primer

<400> SEQUENCE: 26
tataggatcc tgcggtgtgc ccgtgagg                                   28

<210> SEQ ID NO 27
<211> LENGTH: 32
<212> TYPE: DNA
<213> ORGANISM: Artificial Sequence
<220> FEATURE:
<223> OTHER INFORMATION: Primer

<400> SEQUENCE: 27
tataagcttc agccggcgac cgaggcgtcg ta                              32

<210> SEQ ID NO 28
<211> LENGTH: 27
<212> TYPE: DNA
<213> ORGANISM: Artificial Sequence
<220> FEATURE:
<223> OTHER INFORMATION: Primer

<400> SEQUENCE: 28
ggaagatctt gcttgggcga caccaca                                    27

<210> SEQ ID NO 29
<211> LENGTH: 30
<212> TYPE: DNA
<213> ORGANISM: Artificial Sequence
<220> FEATURE:
<223> OTHER INFORMATION: Primer

<400> SEQUENCE: 29
tataaagctt ttatactttg aacttggccc                                 30

<210> SEQ ID NO 30
<211> LENGTH: 34
<212> TYPE: DNA
<213> ORGANISM: Artificial Sequence
<220> FEATURE:
<223> OTHER INFORMATION: Primer
```

```
<400> SEQUENCE: 30
tatatagatc tgtgacggct gtgaactccg tccg                          34

<210> SEQ ID NO 31
<211> LENGTH: 29
<212> TYPE: DNA
<213> ORGANISM: Artificial Sequence
<220> FEATURE:
<223> OTHER INFORMATION: Primer

<400> SEQUENCE: 31
tatatagatc tgccgactcc tgcccgacc                                29

<210> SEQ ID NO 32
<211> LENGTH: 31
<212> TYPE: DNA
<213> ORGANISM: Artificial Sequence
<220> FEATURE:
<223> OTHER INFORMATION: Primer

<400> SEQUENCE: 32
tataaagctt ctaggtcgtg gcgccgagga t                             31

<210> SEQ ID NO 33
<211> LENGTH: 30
<212> TYPE: DNA
<213> ORGANISM: Artificial Sequence
<220> FEATURE:
<223> OTHER INFORMATION: Primer

<400> SEQUENCE: 33
ggaagatctg tgagcaatcg gcgcaccgca                               30

<210> SEQ ID NO 34
<211> LENGTH: 37
<212> TYPE: DNA
<213> ORGANISM: Artificial Sequence
<220> FEATURE:
<223> OTHER INFORMATION: Primer

<400> SEQUENCE: 34
tataagcttc actgcgggtg cgccgccacg tagtcgg                       37

<210> SEQ ID NO 35
<211> LENGTH: 24
<212> TYPE: DNA
<213> ORGANISM: Artificial Sequence
<220> FEATURE:
<223> OTHER INFORMATION: Primer

<400> SEQUENCE: 35
ggaagatctg tgcccgcatc accc                                     24

<210> SEQ ID NO 36
<211> LENGTH: 30
<212> TYPE: DNA
<213> ORGANISM: Artificial Sequence
<220> FEATURE:
<223> OTHER INFORMATION: Primer

<400> SEQUENCE: 36
tataagcttc agattcgcca cgacagttgg                               30

<210> SEQ ID NO 37
<211> LENGTH: 34
<212> TYPE: DNA
```

<213> ORGANISM: Artificial Sequence
<220> FEATURE:
<223> OTHER INFORMATION: Primer

<400> SEQUENCE: 37
atatggatcc gtgagcaagg ttccgacgat cgaa        34

<210> SEQ ID NO 38
<211> LENGTH: 38
<212> TYPE: DNA
<213> ORGANISM: Artificial Sequence
<220> FEATURE:
<223> OTHER INFORMATION: Primer

<400> SEQUENCE: 38
atataagctt tcagcgcggt atgtagtcga aggtgtcc        38

<210> SEQ ID NO 39
<211> LENGTH: 35
<212> TYPE: DNA
<213> ORGANISM: Artificial Sequence
<220> FEATURE:
<223> OTHER INFORMATION: Primer

<400> SEQUENCE: 39
atatggatcc gtgtccgccg gaatcatcct catgg        35

<210> SEQ ID NO 40
<211> LENGTH: 35
<212> TYPE: DNA
<213> ORGANISM: Artificial Sequence
<220> FEATURE:
<223> OTHER INFORMATION: Primer

<400> SEQUENCE: 40
atataagctt tcacagcgcg gcggtgagcc gccac        35

<210> SEQ ID NO 41
<211> LENGTH: 40
<212> TYPE: DNA
<213> ORGANISM: Artificial Sequence
<220> FEATURE:
<223> OTHER INFORMATION: Primer

<400> SEQUENCE: 41
atatagatct gtgacgcacg aatcgaccgc cgcatggcgg        40

<210> SEQ ID NO 42
<211> LENGTH: 37
<212> TYPE: DNA
<213> ORGANISM: Artificial Sequence
<220> FEATURE:
<223> OTHER INFORMATION: Primer

<400> SEQUENCE: 42
atataagctt tcagcgcacc gccgtcgggg cgtcggc        37

<210> SEQ ID NO 43
<211> LENGTH: 30
<212> TYPE: DNA
<213> ORGANISM: Artificial Sequence
<220> FEATURE:
<223> OTHER INFORMATION: Primer

<400> SEQUENCE: 43
ggaagatctt gtgcggtgtg cccgtgaggg        30

```
<210> SEQ ID NO 44
<211> LENGTH: 30
<212> TYPE: DNA
<213> ORGANISM: Artificial Sequence
<220> FEATURE:
<223> OTHER INFORMATION: Primer

<400> SEQUENCE: 44
atagaattcg ccggcgaccg aggcgtcgta                                    30

<210> SEQ ID NO 45
<211> LENGTH: 26
<212> TYPE: DNA
<213> ORGANISM: Artificial Sequence
<220> FEATURE:
<223> OTHER INFORMATION: Primer

<400> SEQUENCE: 45
ggaagatctg cttgggcgac accaca                                        26

<210> SEQ ID NO 46
<211> LENGTH: 29
<212> TYPE: DNA
<213> ORGANISM: Artificial Sequence
<220> FEATURE:
<223> OTHER INFORMATION: Primer

<400> SEQUENCE: 46
tatagaattc tactttgaac ttggcccgc                                     29

<210> SEQ ID NO 47
<211> LENGTH: 30
<212> TYPE: DNA
<213> ORGANISM: Artificial Sequence
<220> FEATURE:
<223> OTHER INFORMATION: Primer

<400> SEQUENCE: 47
tatatagatc ttgacggctg tgaactccgt                                    30

<210> SEQ ID NO 48
<211> LENGTH: 28
<212> TYPE: DNA
<213> ORGANISM: Artificial Sequence
<220> FEATURE:
<223> OTHER INFORMATION: Primer

<400> SEQUENCE: 48
tatagaattc ggtcgtggcg ccgaggat                                      28

<210> SEQ ID NO 49
<211> LENGTH: 31
<212> TYPE: DNA
<213> ORGANISM: Artificial Sequence
<220> FEATURE:
<223> OTHER INFORMATION: Primer

<400> SEQUENCE: 49
tatatagatc ttggccgact cctgcccgac c                                  31

<210> SEQ ID NO 50
<211> LENGTH: 29
<212> TYPE: DNA
<213> ORGANISM: Artificial Sequence
<220> FEATURE:
<223> OTHER INFORMATION: Primer
```

```
<400> SEQUENCE: 50
ggaagatctt ggtgagcaat cggcgcacc                                        29

<210> SEQ ID NO 51
<211> LENGTH: 36
<212> TYPE: DNA
<213> ORGANISM: Artificial Sequence
<220> FEATURE:
<223> OTHER INFORMATION: Primer

<400> SEQUENCE: 51
tatagaattc ctgcgggtgc gccgccacgt agtcgg                                36

<210> SEQ ID NO 52
<211> LENGTH: 30
<212> TYPE: DNA
<213> ORGANISM: Artificial Sequence
<220> FEATURE:
<223> OTHER INFORMATION: Primer

<400> SEQUENCE: 52
ggaagatctt ggtgcccgca tcacccgttc                                       30

<210> SEQ ID NO 53
<211> LENGTH: 30
<212> TYPE: DNA
<213> ORGANISM: Artificial Sequence
<220> FEATURE:
<223> OTHER INFORMATION: Primer

<400> SEQUENCE: 53
tatagaattc gattcgccac gacagttggg                                       30

<210> SEQ ID NO 54
<211> LENGTH: 15
<212> TYPE: PRT
<213> ORGANISM: Mycobacterium avium
<220> FEATURE:
<221> NAME/KEY: MISC_FEATURE
<223> OTHER INFORMATION: Mycobacterium avium subsp. Paratuberculosis
      bovis

<400> SEQUENCE: 54

Leu Val Pro Ile Ile Glu Pro Glu Val Thr Ile Ser Ile Ala Asp
1               5                   10                  15

<210> SEQ ID NO 55
<211> LENGTH: 15
<212> TYPE: PRT
<213> ORGANISM: Mycobacterium avium
<220> FEATURE:
<221> NAME/KEY: MISC_FEATURE
<223> OTHER INFORMATION: Mycobacterium avium subsp. Paratuberculosis
      bovis

<400> SEQUENCE: 55

Pro Leu Ile Glu His Pro Lys Val Met Arg Val Val Ala Leu Ser
1               5                   10                  15

<210> SEQ ID NO 56
<211> LENGTH: 15
<212> TYPE: PRT
<213> ORGANISM: Mycobacterium avium
<220> FEATURE:
<221> NAME/KEY: MISC_FEATURE
<223> OTHER INFORMATION: Mycobacterium avium subsp. Paratuberculosis
      bovis
```

```
<400> SEQUENCE: 56

Lys Val Met Arg Val Val Ala Leu Ser Gly Gly Tyr Ser Arg Glu
1               5                   10                  15

<210> SEQ ID NO 57
<211> LENGTH: 20
<212> TYPE: PRT
<213> ORGANISM: Mycobacterium avium
<220> FEATURE:
<221> NAME/KEY: MISC_FEATURE
<223> OTHER INFORMATION: Mycobacterium avium subsp. Paratuberculosis
      bovis

<400> SEQUENCE: 57

Leu Leu Pro Ile Gly Tyr Asp Ala Ser Ser Pro Ile Pro Ala Ala Asp
1               5                   10                  15

Tyr Val Ala Ala
            20

<210> SEQ ID NO 58
<211> LENGTH: 20
<212> TYPE: PRT
<213> ORGANISM: Mycobacterium avium
<220> FEATURE:
<221> NAME/KEY: MISC_FEATURE
<223> OTHER INFORMATION: Mycobacterium avium subsp. Paratuberculosis
      bovis

<400> SEQUENCE: 58

Ile Gly Tyr Asp Ala Ser Ser Pro Ile Pro Ala Ala Asp Tyr Val Ala
1               5                   10                  15

Ala His Pro Gln
            20

<210> SEQ ID NO 59
<211> LENGTH: 20
<212> TYPE: PRT
<213> ORGANISM: Mycobacterium avium
<220> FEATURE:
<221> NAME/KEY: MISC_FEATURE
<223> OTHER INFORMATION: Mycobacterium avium subsp. Paratuberculosis
      bovis

<400> SEQUENCE: 59

Glu Leu Ile Asp Val Tyr Asp Arg Asn Val Asp Ala Arg Arg Gln Leu
1               5                   10                  15

Thr Ala Leu Thr
            20

<210> SEQ ID NO 60
<211> LENGTH: 20
<212> TYPE: PRT
<213> ORGANISM: Mycobacterium avium
<220> FEATURE:
<221> NAME/KEY: MISC_FEATURE
<223> OTHER INFORMATION: Mycobacterium avium subsp. Paratuberculosis
      bovis

<400> SEQUENCE: 60

Ser Gly Val Gly Trp Asn Tyr Leu Ala Ala Ile Asn Phe Ile Glu Thr
1               5                   10                  15

Arg Phe Gly Ser
            20
```